US010450576B2

(12) United States Patent
Li

(10) Patent No.: US 10,450,576 B2
(45) Date of Patent: Oct. 22, 2019

(54) SOYBEAN U6 SMALL NUCLEAR RNA GENE PROMOTERS AND THEIR USE IN CONSTITUTIVE EXPRESSION OF SMALL RNA GENES IN PLANTS

(71) Applicant: E. I. DU PONT DE NEMOURS AND COMPANY, Wilmington, DE (US)

(72) Inventor: Zhongsen Li, Hockessin, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 15/558,296

(22) PCT Filed: Mar. 21, 2016

(86) PCT No.: PCT/US2016/023374
§ 371 (c)(1),
(2) Date: Sep. 14, 2017

(87) PCT Pub. No.: WO2016/160389
PCT Pub. Date: Oct. 6, 2016

(65) Prior Publication Data
US 2018/0057832 A1    Mar. 1, 2018

Related U.S. Application Data

(60) Provisional application No. 62/139,075, filed on Mar. 27, 2015.

(51) Int. Cl.
C12N 15/82    (2006.01)

(52) U.S. Cl.
CPC ..... C12N 15/8216 (2013.01); C12N 15/8213 (2013.01)

(58) Field of Classification Search
None
See application file for complete search history.

(56) References Cited

U.S. PATENT DOCUMENTS

| | | | |
|---|---|---|---|
| 5,036,006 A | 7/1991 | Sanford | |
| 5,959,177 A | 9/1999 | Hein | |
| 7,292,055 B2 | 8/2007 | Choo | |
| 8,586,361 B2 | 11/2013 | Tao | |
| 8,697,359 B1 | 4/2014 | Zhang | |
| 8,771,945 B1 | 7/2014 | Zhang | |
| 8,795,965 B2 | 8/2014 | Zhang | |
| 8,865,406 B2 | 10/2014 | Zhang | |
| 8,871,445 B2 | 10/2014 | Cong | |
| 8,889,356 B2 | 11/2014 | Zhang | |
| 8,889,418 B2 | 11/2014 | Broad | |
| 8,895,308 B1 | 11/2014 | Zhang | |
| 8,906,616 B2 | 12/2014 | Zhang | |
| 8,932,814 B2 | 1/2015 | Cong | |
| 8,945,839 B2 | 2/2015 | Zhang | |
| 8,993,233 B2 | 3/2015 | Broad | |
| 8,999,641 B2 | 4/2015 | Broad | |
| 9,163,284 B2 | 10/2015 | Liu | |
| 9,493,782 B2 | 11/2016 | Cigan | |
| 9,840,713 B2 | 12/2017 | Zhang | |
| 9,885,033 B2 | 11/2018 | Joung | |
| 2004/0231016 A1 | 11/2004 | Wang | |
| 2007/0083945 A1 | 4/2007 | Byrum | |
| 2007/0178593 A1 | 8/2007 | Miller | |
| 2007/0199095 A1 | 8/2007 | Allen | |
| 2009/0104700 A1 | 4/2009 | Samuel et al. | |
| 2009/0133152 A1 | 5/2009 | Lyznik | |
| 2010/0076057 A1 | 3/2010 | Sontheimer | |
| 2010/0159598 A1 | 6/2010 | Jayakumar et al. | |
| 2010/0311168 A1 | 12/2010 | Samuel et al. | |
| 2010/0313293 A1 | 12/2010 | Albertsen | |
| 2011/0035836 A1 | 2/2011 | Eudes et al. | |
| 2011/0247100 A1 | 10/2011 | Samboju et al. | |
| 2012/0023619 A1 | 1/2012 | Samboju et al. | |
| 2012/0023620 A1 | 1/2012 | Yau et al. | |
| 2012/0244569 A1 | 9/2012 | Samuel et al. | |
| 2013/0198888 A1 | 8/2013 | Falco | |
| 2013/0263324 A1 | 10/2013 | Lassner | |
| 2014/0020131 A1 | 1/2014 | Bidney | |
| 2014/0068797 A1 | 3/2014 | Doudna | |
| 2014/0096284 A1 | 4/2014 | Martin-Ortigosa et al. | |
| 2014/0179006 A1 | 6/2014 | Zhang | |

(Continued)

FOREIGN PATENT DOCUMENTS

| | | |
|---|---|---|
| DE | 102015006335 | 11/2016 |
| WO | 2005049842 | 6/2005 |

(Continued)

OTHER PUBLICATIONS

Li, et al.; "Varied transcriptional efficiencies of multiple *Arabidopsis* U6 small nuclear RNA genes", J Integrative Plant Biol (2007) 49(2):222-229.

Kim, et al.; "Isolation and characterization of Medicago truncatula U6 promoters for the construction of small hairpin RNA-mediated gene silencing vectors", Plant Mol Biol Reporter (2013) 31(3):581-593.

International Search Report for PCT/US16/23374 dated Oct. 6, 2016.

Vladimir Nekrasov et al., Targeted mutagenesis in the model plant Nicotiana benthamiana using Cas9 RNA-guided endonuclease, Nature Biotechnology, pp. 691-693, vol. 31, No. 8, Aug. 2013.

(Continued)

*Primary Examiner* — Jason Deveau Rosen

(57) ABSTRACT

The invention relates to gene expression regulatory sequences from soybean, specifically to promoters of U6 small nuclear RNA genes, and fragments thereof, and their use in promoting the expression of one or more heterologous nucleic acid fragments in a constitutive manner in plants. The invention further discloses compositions, polynucleotide constructs, transformed host cells, transgenic plants and seeds containing the recombinant construct with the promoter, and methods for preparing and using the same.

15 Claims, 6 Drawing Sheets

Figure 1:
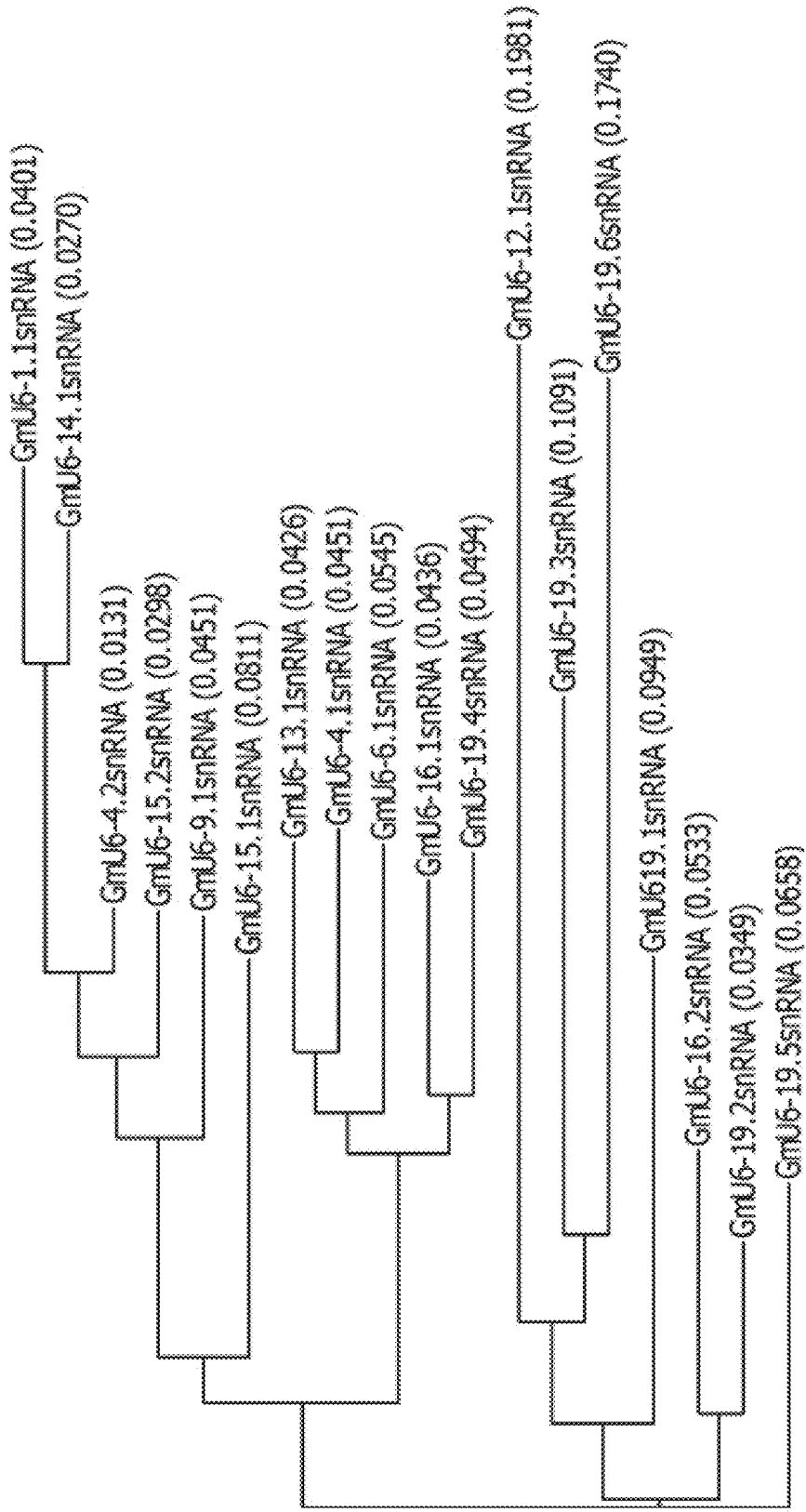

Specification includes a Sequence Listing.

(56) References Cited

U.S. PATENT DOCUMENTS

| | | |
|---|---|---|
| 2014/0179770 A1 | 6/2014 | Zhang |
| 2014/0182012 A1 | 6/2014 | Eudes et al. |
| 2014/0186843 A1 | 7/2014 | Zhang |
| 2014/0186919 A1 | 7/2014 | Zhang |
| 2014/0186958 A1 | 7/2014 | Zhang |
| 2014/0189896 A1 | 7/2014 | Zhang |
| 2014/0227787 A1 | 8/2014 | Zhang |
| 2014/0234972 A1 | 8/2014 | Zhang |
| 2014/0242664 A1 | 8/2014 | Zhang |
| 2014/0242699 A1 | 8/2014 | Zhang |
| 2014/0242700 A1 | 8/2014 | Zhang |
| 2014/0242702 A1 | 8/2014 | Chen |
| 2014/0242703 A1 | 8/2014 | Samuel et al. |
| 2014/0248702 A1 | 9/2014 | Zhang |
| 2014/0256046 A1 | 9/2014 | Zhang |
| 2014/0273234 A1 | 9/2014 | Zhang |
| 2014/0273235 A1 | 9/2014 | Voytas |
| 2014/0310830 A1 | 10/2014 | Zhang |
| 2014/0335620 A1 | 11/2014 | Zhang |
| 2014/0342456 A1 | 11/2014 | Mali |
| 2014/0357530 A1 | 12/2014 | Zhang |
| 2014/0370558 A1 | 12/2014 | Mathis |
| 2015/0044191 A1 | 2/2015 | Liu |
| 2015/0044772 A1 | 2/2015 | Zhao |
| 2015/0059010 A1 | 2/2015 | Cigan |
| 2015/0067922 A1 | 3/2015 | Yang |
| 2015/0079681 A1 | 3/2015 | Zhang |
| 2015/0082478 A1 | 3/2015 | Cigan et al. |
| 2015/0167000 A1 | 6/2015 | Voytas |
| 2015/0167009 A1 | 6/2015 | D'Halluin |
| 2015/0284727 A1 | 10/2015 | Kim et al. |
| 2015/0291967 A1 | 10/2015 | Mathis |
| 2016/0024524 A1 | 1/2016 | Joung |
| 2016/0201072 A1 | 7/2016 | Pioneer |
| 2016/0208271 A1 | 7/2016 | Cigan et al. |
| 2016/0208272 A1 | 7/2016 | Cigan et al. |
| 2016/0251667 A1 | 9/2016 | Cigan et al. |
| 2017/0022521 A1 | 1/2017 | Samuel et al. |
| 2017/0166912 A1 * | 6/2017 | Brower-Toland ............... C12N 15/8213 |
| 2018/0002715 A1 | 1/2018 | Cigan et al. |
| 2018/0057832 A1 | 3/2018 | Li |
| 2018/0142263 A1 | 5/2018 | May et al. |
| 2018/0163203 A1 | 6/2018 | Bennett et al. |
| 2018/0230476 A1 | 8/2018 | Cigan et al. |
| 2018/0258417 A1 | 9/2018 | Cigan et al. |
| 2018/0273960 A1 | 9/2018 | Cigan et al. |
| 2018/0282763 A1 | 10/2018 | Cigan et al. |
| 2018/0327785 A1 | 11/2018 | Cigan et al. |
| 2018/0346895 A1 | 12/2018 | Cigan et al. |
| 2018/0371479 A1 | 12/2018 | Cigan et al. |
| 2019/0040405 A1 | 2/2019 | Cigan et al. |
| 2019/0100745 A1 | 4/2019 | Cigan et al. |
| 2019/0100762 A1 | 4/2019 | Cigan et al. |
| 2019/0136248 A1 | 5/2019 | Cigan et al. |

FOREIGN PATENT DOCUMENTS

| | | | | |
|---|---|---|---|---|
| WO | 2007025097 | 3/2007 | | |
| WO | 2009042164 | 4/2009 | | |
| WO | 2010011961 | 1/2010 | | |
| WO | 2010077319 | 7/2010 | | |
| WO | 2011143124 | 11/2011 | | |
| WO | 2012129373 | 9/2012 | | |
| WO | 2013066423 | 5/2013 | | |
| WO | 2013068845 | 5/2013 | | |
| WO | 2013098244 | 7/2013 | | |
| WO | 2013112686 | 8/2013 | | |
| WO | 2013141680 | 9/2013 | | |
| WO | 2013142578 | 9/2013 | | |
| WO | 2013173535 | 11/2013 | | |
| WO | 2013176772 | 11/2013 | | |
| WO | 2014018423 | 1/2014 | | |
| WO | 2014065596 | 5/2014 | | |
| WO | 2014071006 | 5/2014 | | |
| WO | 2014093479 | 6/2014 | | |
| WO | 2014093635 | 6/2014 | | |
| WO | 2014093694 | 6/2014 | | |
| WO | 2014093712 | 6/2014 | | |
| WO | 2014093768 | 6/2014 | | |
| WO | 2014144155 | 9/2014 | | |
| WO | 2014144761 | 9/2014 | | |
| WO | 2014150624 | 9/2014 | | |
| WO | 2014186686 | 11/2014 | | |
| WO | 2014194190 | 12/2014 | | |
| WO | 2015006294 | 1/2015 | | |
| WO | 2015026883 | 2/2015 | | |
| WO | 2015026885 | 2/2015 | | |
| WO | 2015026886 | 2/2015 | | |
| WO | 2015026887 | 2/2015 | | |
| WO | 2015071474 | 5/2015 | | |
| WO | 2015112896 | 7/2015 | | |
| WO | 2015131101 | 9/2015 | | |
| WO | WO-2015131101 A1 * | 9/2015 | ......... | C12N 15/8213 |
| WO | 2015189693 | 12/2015 | | |
| WO | 2016007347 | 1/2016 | | |
| WO | 2016033298 | 3/2016 | | |
| WO | 2016186946 | 11/2016 | | |
| WO | 2017034971 | 3/2017 | | |
| WO | 2017062855 | 4/2017 | | |
| WO | 2017155714 | 9/2017 | | |
| WO | 2017155715 | 9/2017 | | |
| WO | 2017218185 | 12/2017 | | |

OTHER PUBLICATIONS

J.-H. Oh et al: "CRISPR-Cas9-assisted recombineering in Lactobacillus reuteri", Nucleic Acids Research, vol. 42 No. 17, Sep. 29, 2014, p. e131 (and Supplemental).

Peng et al, "A Synthetic arabinose-inducible promoter confers high levels of recombinant protein expression in hyperthermophilic Archaeon sulfolobus islandicus", Appl Environ Microbiol, Aug. 2012,pp. 5630-5637, vol. 78 No. 16.

Phillips, "The challenge of gene therapy and DNA delivery", Pharm Pharmacology, 2001, 1169-1174 vol. 53.

Nancy Podevin et al., Site-directed nucleases: a paradigm shift in predictable, knowledge-based plant breeding, Trends in Biotechnology, Jun. 2013, pp. 375-383, vol. 31, No. 6.

Lei S. Qi et al., Repurposing CRISPR as an RNA-Guided Platform for Sequence-Specific Control of Gene Expression, Cell, Feb. 28, 2013, pp. 1173-1183, vol. 152(5).

Qiudeng Que et al: "Maize transformation technology development for commercial event generation", Frontiers in Plant Science, vol. 5, Aug. 5, 2014, pp. 12-15.

Ramakrishna et al: "Gene disruption by cell-penetrating peptide-mediated delivery of Cas9 protein and guide RNA", Genome Res 24:1020-27 (Apr. 2014).

Sivaprakash Ramalingam et al., A CRISPR way to engineer the human genome, Genome Biology, 2013, 4 pages, vol. 14 (Feb. 26, 2013).

Reeks et al., "CRISPR interference: a structural perspective.", 2013, Biochem J, pp. 155-166, vol. 453.

Relic et al., Interaction of the DNA modifying proteins VirD1 and VirD2 of Agrobacterium tumefaciens: Analysis by subcellular localization in mammalian cells, Proc Natl Acad Sci, 2008, 95:9105-9110.

Retallack et al, "A single base pair mutation changes the specificities of both a transcription activation protein and its binding site", PNAS,Oct. 1993, pp. 9562-9565, vol. 90.

Paul D. Sadowski, Site-specific genetic recombination: hops, flips, and flops, FASEB, 1993, pp. 760-767, vol. 7.

Neville E. Sanjana et al., A Transcription Activator-Like Effector (TALE) Toolbox for Genome Engineering, Nat. Protoc, 2012, pp. 171-192, vol. 7(1).

Rosemary Sanozky-Dawes et al: "Occurrence and activity of a type II CRISPR-Cas system in Lactobacillus gasseri", Microbiology, vol. 161, No. 9, Sep. 1, 2015, pp. 1752-1761.

(56) References Cited

OTHER PUBLICATIONS

Rimantas Sapranauskas et al., The *Streptococcus thermophilus* CRISPR/Cas system provides immunity in *Escherichia coli* Nucleic Acids Research, Aug. 2011, pp. 9275-9282, vol. 39, No. 21.

Brian Sauer, Site-specific recombination: developments and applications, Current Opinion in Biotechnology, 1994, pp. 521-527, vol. 5.

Shiraz A Shah et al: "Protospacer recognition motifs", RNA Biology, May 1, 2013, pp. 1547-6286, vol. 10 No. 5.

Qiwei Shan et al., Targeted genome modification of crop plants using a CRISPR-Cas system, Nature Biotechnology, Aug. 2013, pp. 686-688, vol. 31, No. 8.

Bin Shen et al., Generation of gene-modified mice via Cas9/RNA-mediated gene targeting, Cell Research, May 2013, pp. 720-723, vol. 23, No. 5.

Vipula K Shukla et al: Precise genome modificaiton in the crop species *Zea mays* using zinc-finger nucleases, Nature, Apr. 29, 2009, p. 437, vol. 459, No. 7245 (and supplemental).

Sinkunas Tomas et al: "Cas3 is a single-stranded DNA nuclease and ATP-dependent helicase in the CRISPR/Cas immune system", EMBO, vol. 30 No. 7, Apr. 2011, pp. 1335-1342.

Strauss, "Zinc Fingers, TAL Effectors, or Cas9-Based DNA Binding Proteins: What's Best for Targeting Desired Genome Loci?", MolecularPlant, Sep. 2013, vol. 6 No. 5 pp. 1384-1387.

Sun Zhihong et al: "Expanding the biotechnology potential of lactobacilli through comparative genomics of 213 strains and associated genera", Nature Communications, Nature Publishing Group, UK, vol. 6, 29 Sep. 2015, p. 7.

Sergei Svitashev et al: "Targeted mutagenesis, precise gene editing, and site-specific gene insertion in maize using Cas9 and guide RNA", Plant Physiology, vol. 169, No. 2, Aug. 12, 2015, pp. 931-945.

Bruno Tinland et al., The T-DNA-linked VirD2 protein contains two distinct functional nuclear localization signals, Proc. Natl. Acad. Sci, Aug. 1992, pp. 7442-7446, vol. 89.

Ui-Tei et al, "Functional dissection of siRNA sequence by systematic DNA substitution: modified siRNA with a DNA seed arm is a powerful tool for mammalian gene silencing with significantly reduced off-target effect" Nucleic Acid Res. 2008, pp. 2146-2151, vol. 36 No. 7.

John Van Der Oost, New Tool for Genome Surgery, Science, Feb. 15, 2013, pp. 768-770, vol. 339.

Daniel F. Voytas, Plant Genome Engineering with Sequence-Specific Nucleases, Annual Review of Plant Biology, pp. 327-350, vol. 64, Mar. 1, 2013.

Ming-Bo Wang et al., Hairpin RNAs derived from RNA polymerase II and polymerase III promoter-directed transgenes are processed differently in plants, RNA, May 2008, pp. 903-913, vol. 14 No. 5.

Jianbin Wang et al., Targeted gene addition to a predetermined site in the human genome using a ZFN-based nicking enzyme, Genome Research, 2012, pp. 1316-1326.

Haoyi Wang et al., One-Step Generation of Mice Carrying Mutations in Multiple Genes by CRISPR/Cas-Mediated Genome Engineering, Cell, May 9, 2013, pp. 910-918, vol. 153(4).

Westra et al: "CRISPR immunity relies on the consecutive binding and degradation of negatively supercoiled invader DNA by Cascade and Cas3", Mol Cell, Apr. 19, 2012,pp. 595-605, vol. 46 No. 5.

Blake Wiedenheft et al., RNA-guided genetic silencing systems in bacteria and archaea, Nature, Feb. 16, 2012, pp. 331-338, vol. 482.

Wierzbicki et al: "Noncoding Transcription by RNA Polymerase Pol IVb/Pol V Mediates Transcriptional Silencing of Overlapping and Adjacent Genes", Cell, 2008, vol. 135, pp. 635-648.

Je Wook Woo et al: "DNA-free genome editing in plants with preassembled CRISPR-Cas9 ribonucleoproteins", Nature Biotechnology, vol. 33 No. 11, Oct. 19, 2015, pp. 1162-1164, XP055290196.

Wu, "Tn5 transposase-assisted transformation of indica rice", Plant J, 2015, pp. 186-200, vol. 68.

Kabin Xie et al., RNA-Guided Genome Editing in Plants Using a CRISPR-Cas System, Nov. 2013, Molecular Plant, pp. 1975-1983, vol. 6, No. 6.

Xing e al., "A CRISPR/Cas9 toolkit for multiplex genome editing in plants", BMC Plant Biol, 2014, vol. 14 No. 1, pp. 327-338.

Kun Xu et al: Efficient genome engineering in eukaryotes using Cas9 from *Streptococcus thermophilus*, Cellular and Molecular Life Sciences, vol. 72 No. 2, Jul. 20, 2014, pp. 383-399 (and supplemental).

Chaoyou Xue et al: "CRISPR interference and priming varies with individual spacer sequences", Nucleic Acids Research, vol. 43 No. 22, Nov. 19, 2015, pp. 10831-10847.

Bernd Zetsche et al: "Cpf1 is a single RNA-guide endonuclease of a Class 2 CRISPR-Cas system", Cell, vol. 163 No. 3, Oct. 1, 2015, pp. 759-771, XP055267511.

Zhang, "Transcription Activator-Like Effector Nucleases Enable Efficient Plant Genome Engineering",Plant Physiology, 2013, vol. 161, pp. 20-27.

Zhang et al., "The CRISPR/Cas9 system produces specific and homozygous targeted gene editing in rice in one generation", Plant Biotech J, 2014, vol. 12 No. 6, pp. 797-807.

Liang Zhen et al: "Targeted mutagenesis in *Zea mays* using TALENs and the CRISPR/Cas system", Journal of Genetics and Genomics, Dec. 14, 2013, pp. 63-68, vol. 41, No. 2.

Alicja Ziemienowicz, Import of Agrobacterium T-DNA into plant nuclei: two distinct functions of VirD2 and VirE2 proteins, The Plant Cell, 2001, 13:369-383.

John A Zuris, et al: "Cationic lipid-mediated delivery of proteins enables efficient protein-based genome editing in vitro and in vivo", Nature Biotech, vol. 33 No. 1, Oct. 30, 2014, pp. 73-80.

William Ainley et al: "Trait stacking via targeted genome editing", Plant Biotechnology Journal, Aug. 19, 2013, pp. 1126-1134, vol. 11, No. 9.

Rodolphe Barrangou et al., CRISPR Provides Acquired Resistance Against Viruses in Prokaryotes, Science, 2007, pp. 1709-1712, vol. 315.

Rodolphe Barrangou et al., RNA-mediated programmable DNA cleavage, Nature Biotechnology, Sep. 2012, pp. 836-838, vol. 30, No. 9.

Rodolphe Barrangou et al., CRISPR-Cas sytems and RNA-guided interference, WIREs RNA, 2013, pp. 267-278, vol. 4.

Barrangou & Marraffini, "CRISPR-Cas systems: prokaryotes upgrade to adaptive immunity", Mol Cell 54:234-44 (Apr. 2014).

Peter R. Beetham, A tool for functional plant genomics: Chimeric RNA/DNA oligonucleotides cause in vivo gene-specific mutations, Proc. Natl., Acad. Sci USA, Plant Biology, Jul. 1999, pp. 8774-8778, vol. 96.

Khaoula Belhaj et al., Plant genome editing made easy: targeted mutagenesis in model and crop plants using the CRISPR/Cas system, Plant Methods, 2013, pp. 39-48, vol. 9.

Beurdeley et al: "Compact designer TALENs for efficient genome engineering", Nat Commun, Apr. 23, 2013, pp. 1-8, vol. 4, No. 1762.

Joseph Bondy-Denomy et al: "To acquire or resist: the complex biological effects of CRISPR-Cas systems", Trends in Microbiology, vol. 22 No. 4, Feb. 26, 2014, pp. 218-225.

Luisa Bortesi et al: "The CRISPR/Cas9 system for plant genome editing and beyond", Biotechnology Advances, vol. 33 No. 1, Jan. 1, 2015, pp. 41-52, XP055217852.

Briner Alexandra E et al.: "Guide RNA functional modules direct Cas9 activity and orthogonality", Molecular Cell, vol. 56 No. 2, Oct. 16, 2014, pp. 333-339 (and Supplemental).

Nannan Chang et al., Genome editing with RNA-guided Cas9 nuclease in Zebrafish embryos, Cell Research, 2013, pp. 465-472, vol. 23.

Cheng et al: "Multiplexed activation of endogenous genes by CRISPR-on, an RNA-guided transcriptional activator system", Cell Research, 2013, pp. 1163-1171, vol. 23.

Seung Woo Cho et al., Targeted genome engineering in human cells with the Cas9 RNA-guided endonuclease, Nature Biotechnology, Mar. 2013, pp. 230-232, vol. 31, No. 3.

Krzysztof Chylinski et al., The tracrRNA and Cas9 families of type II CRISPR-Cas immunity systems, Rna Biology, May 2013, pp. 726-737, vol. 10, No. 10.

Claesson M J et al: "Multireplicon genome architecture of Lactobacillus salivarius", PNAS, Apr. 1, 2006, pp. 6718-6723, vol. 103 No. 17.

(56) References Cited

OTHER PUBLICATIONS

Le Cong et al., Multiplex Genome Engineering Using CRISPR/Cas Systems, Sciencexpress Reports, Jan. 3, 2013, pp. 1-7, vol. 1.
Database "cas9-CRISPR-associated endonuclease CAs9—Bacillus cereus VD131—cas9 gene & protein", UniProt database entry: R8LDU5, 2013.
Database hypothetical protein [Lactobacillus reuteri]: NCBI Reference Sequence WP_019251774.1, 2013.
Database "CRISPR-associated endonuclease Cas9, Lactobacillus salivarius (strain UCC118): Q1WVK1_LACS1", UniProt, 2006.
Database "Lactobacillus reuteri TD1, complete genome, NCBI Reference Sequence: NC_021872.1", 2018.
Database RefSEQ NCBI, database accession WP_010710291.1, "Type II CRISPR-RNA-guided endonuclease Cas9 [Enterococcus faecalis]", 2002.
Database RefSEQ NCBI, database accession WP_023519017, "Type II CRISPR-RNA-guided endonuclease Cas9 [Enterococcus mundtii]", 2002.
Database RefSEQ NCBI, database accession WP_031455829, "Type II CRISPR-RNA-guided endonuclease Cas9 [Flavobacterium chungangense]", 2002.
Database RefSEQ NCBI, database accession WP_048395223, "Type II CRISPR-RNA-guided endonuclease Cas9 [Pseudomonas lini]", 2002.
Database UniProt "RecName: Full-CRISPR-associated endonuclease Cas9" retrieved from EBI accession No. UNIPROT:A0A0F4LLE0, 2015.
Eitza Deltcheva et al., CRISPR RNA maturation by trans-encoded small RNA and host factor RNase III, Nature, Mar. 31, 2011, pp. 602-607, vol. 471.
Kathleen D'Halluin et al., Targeted molecular trait stacking in cotton through targeted double-strand break induction, Plant Biotechnology Journal, pp. 933-941, vol. 11, Jun. 18, 2013.
James E. Dicarlo et al., Genome engineering in *Saccharomyces cerevisiae* using CRISPR-Cas systems, Nucleic Acids Research, Mar. 4, 2013, pp. 4336-4343, vol. 41, No. 7.
Vesna Djukanovic et al: "Male-sterile maize plants produced by targeted mutagenesis of the cytochrome P450-like gene (MS26) using a re-designed I-CreI homing endonuclease", The Plant Journal, Nov. 5, 2013, pp. 888-899, vol. 76, No. 5.
Doudna & Charpentier, "The new frontier of genome engineering with CRISPR-Cas9", Sci 346(6213):1258096 (2014).
Lukas E Dow et al: "Inducible in vivo genome editing with CRISPR-Cas9", Nature Biotechnology, vol. 33, No. 4, Feb. 18, 2015, pp. 390-394.
Kirsten M Ellegaard et al: "Extensive intra-phylotype diversity in lactobacilli and bifidobacteria from the honeybee gut", MBC Genomics, vol. 16, No. 1, Apr. 11, 2015 p. 284, p. 14, table 3.
Kevin M Esvelt et al: "Orthogonal Cas9 proteins for RNA-guided gene regulation and editing", Nature Methods, Sep. 29, 2013, pp. 1116-1121, vol. 10 No. 11.
Robert D. Fagerlund et al: "The Cpf1 CRISPR-Cas protein expands genome-editing tools", Genome Biology, vol. 523, No. 1, Dec. 17, 2015, p. 481.
Zhengyan Feng et al., Efficient genome editing in plants using a CRISPR/Cas system, Cell Research, 2013, pp. 1229-1232, vol. 23.
Fichtner et al: "Precision genetic modifications: a new era in molecular biology and crop improvement", Planta 239:921-39 (2014).
Yanfang Fu et al., Improving CRISPR-Cas nuclease specificity using truncated guide RNAs, Nature Biotechnology, Mar. 2014, vol. 32, No. 3.
Fujita et al.,"The point mutation in the promoter region and the single nucleotide polymorphism in exon 1 of the cytokeratin 19 gene in human lung cancer cell lines" Lung Cancer, Dec. 2001, vol. 34 No. 3 pp. 387-394.
Todd Funke et al., Structural Basis of Glyphosate Resistance Resulting from the Double Mutation Thr 97 Ile and Pro101 Ser in 5-Enolpyruvylshikimate-e-phosphate synthase from *Escherichia coli*. J Biol Chem vol. 284 No. 15 pp. 9854-9860, Apr. 10, 2009.

Thomas Gaj et al., ZFN, TALEN and CRISPR/Cas-based methods for genome engineering, Trends Biotechnology, Jul. 2013, pp. 397-405, vol. 31(7).
Martin W. Ganal et al: "A large maize (*Zea mays* L.) SNP genotyping array: development and germplasm genotyping, and genetic mapping to compare with B73 reference genome", PLOS One, vol. 6, No. 12, Dec. 8, 2011, p. e28334.
Gardlik et al., "Vectors and delivery systems in gene therapy", Med Sci Monit, 2005, RA110-121, vol. 11 No. 14.
Josiane E. Garneau et al., The CRISPR/Cas bacterial immune system cleaves bacteriophase and plasmid DNA, Nature, 2010, pp. 67-71, vol. 468.
Siedrius Gasiunas et al., Cas9-crRNA ribonucleoprotein complex mediates specific DNA cleavage for adaptive immunity in bacteria, PNAS, Sep. 4, 2012, e2579-2586.
Luke A Gilbert et al., CRISPR-Mediated Modular RNA-Guided Regulation of Transcription in Eukaryotes, Cell, Jul. 18, 2013, pp. 442-451, vol. 154(2).
Scott J. Gratz et al., Genome Engineering of *Drosophila* with the CRISPR RNA-Guided Cas9 Nuclease, Aug. 2013, Genetics, pp. 1029-1035, vol. 194.
Grissa I et al: "CRISPRFinder: a web tool to identify clustered regularly interspaced short palindromic repeats", Nucleic Acids Research, Information Retrieval Ltd, GB, May 31, 2007, pp. W52-W57, vol. 35.
Suillinger Etl Al.: "Fusion of catalytically inactive Cas9 to FokI nuclease improves the specificity of genome modification", Nat Biotech 32(6):577-83 (2014).
Daniel H. Haft et al., A Guild of 45 CRISPR-Associated (Cas) Protein Families and Multiple CRISPR/Cas Subtypes Exist in Prokaryotic Genomes, PLoS Computational Biol, Nov. 11, 2005.
Caryn R. Hale et al., RNA-Guided RNA Cleavage by a CRISPR RNA-Cas Protein Complex, Cell, Nov. 25, 2009, pp. 945-956, vol. 139.
Rachel E. Haurwitz et al., Sequence- and Structure-Specific RNA Processing by a CRISPR Endonuclease, Science, Sep. 10, 2010, pp. 1355-1358, vol. 329.
Heler, "Cas9 specifies functional viral targets during CRISPR-Cas adaptation", Nature, 2015, vol. 519, p. 199.
Philippe Horvath et al., Diversity, Activity, and Evolution of CRISPR Loci in *Streptococcus thermophilus*, Journal of Bacteriology, Feb. 2008, pp. 1401-1412, vol. 190, No. 4.
Philippe Horvath et al., CRISPR/Cas, the Immune System of Bacteria and Archaea, Science, Jan. 8, 2010, pp. 167-170, vol. 327.
Houdebine, "The methods to generate transgenic animals and to control transgene expression", J Biotech, 2002,145-160, vol. 98.
Zhonggang Hou et al., Efficient genome engineering in human pluripotent stem cells using Cas9 from Neisseria meningitides, PNAS, Sep. 24, 2013, pp. 15644-15649, vol. 110, No. 39.
Patrick D. Hsu et al., DNA targeting specificity of RNA-guided Cas9 nucleases, Nature Biotechnology, Sep. 2013, pp. 827-834, vol. 31, No. 9.
Woong Y. Hwang et al., Efficient In Vivo Genome Editing Using RNA-Guided Nucleases, Nature Biotech, Mar. 2013, pp. 227-229, vol. 31, No. 3.
Hyun et al., "Site-directed mutagenesis in *Arabisopsis thaliana* using divided tissue-targeted RGEN of the CRISPR/Cas system to generate heritable null alleles", Planta, Jan. 2015, vol. 241 No. 1, pp. 271-284.
Steve Lin et al: "Enhanced homology-directed human genome engineering by controlled timing of CRISPR/Cas9 delivery", eLIFE, 3:e04766, Dec. 15, 2014.
Jacobs et al, "Targeted genome modifications in soybean with CRISPR/Cas9", BMC Biotechnology, Mar. 2015, vol. 15 No. 1, 10 pages.
Kyle Jacoby et al., Expanding LAGLIDADG endonuclease scaffold diversity by rapidly surveying evolutionary sequence space, Nucleic Acids Research, Feb. 2012, pp. 4954-4964, vol. 40, No. 11.
W. Jiang et al., "Demonstration of CRISPR/Cas9/sgRNA-mediated targeted gene modificaiton in *Arabidopsis*, tobacco, sorghum and rice", Nucleic Acids Research, Sep. 2, 2013, pp. e188-e188, XP055219328, vol. 41 No. 20.

(56) References Cited

OTHER PUBLICATIONS

Wenyan Jiang et al., RNA-guided editing of bacterial genomes using CRISPR-Cas systems, Nature Biotechnology, Mar. 2013, pp. 233, vol. 31, No. 3.
Wenzhi Jiang et al., "Efficient CRISPR/Cas9-mediated gene edigin in *Arabidopsis thalian* and inheritance of modified genes in the T2 and T3 generations", PLOS ONE, vol. 9 No. 6, Jun. 11, 2014, p. e99225, XP055219594.
Wenyan Jiang et al: "CRISPR-Cas: New tools for genetic manipulations of bacterial immunity systems", Annual Review of Microbiology, vol. 69, No. 1, Jul. 22, 2015, pp. 209-228.
Martin Jinek et al., A Programmable Dual-RNA-Guided DNA Endonuclease in Adaptive Bacterial Immunity, Science, Aug. 17, 2012, pp. 816-821, vol. 337.
Martin Jinek et al., RNA-programmed genome editing in human cells, eLife, 2013, e00471, pp. 1-9.
Ross A. Johnson et al., A rapid assay to quantify the cleavage efficiency of custom-designed nucleases in planta, Plant Mol Biol, 2013, pp. 207-221, vol. 82.
Kanchiswamy C N et al: "Non-GMO genetically edited crop plants", Trends in Biotechnology, vol. 33 No. 9, Sep. 1, 2015, XP002765281.
Tautvydas Karvelis et al: "Rapid characterization of CRISPR-Cas9 protospacer adjacent motif sequence elements", Genome Biology, vol. 30 No. 1, Nov. 19, 2015, p. 1335.
Kim Goon-Bo et al: "Isolation and characterization of Medicago truncatula U6 promoters for construction of small hairpin RNA-mediated gene silencing vevctors", Plant Molecular Biology Reporter, vol. 31 No. 3, Jun. 2014, pp. 581-593.
Sojung Kim et al: Highly efficient RNA-guided genome editing in human cells via delivery of purified Cas9 ribonucleoproteins, Genome Res, vol. 24, Apr. 2, 2014, pp. 1012-1019.
Hyeran Kim et al: "Targeted genome editing for crop improvement", Plant Breeding and Biotechnology, vol. 3, No. 4, Dec. 30, 2015, pp. 283-290.
Eugene V. Koonin et al., CRISPR-Cas Evolution of an RNA-based adaptive immunity system in prokaryotes, RNA Biology, May 2013, pp. 679-686, vol. 10:5.
Vinay Kumar et al: "The CRISPR Cas system for plant genome editing: advances and opportunities", Journal of Experimental Botany, vol. 66, No. 1, Nov. 4, 2014, pp. 47-57.
MT Leonard et al: "Complete genome sequences of Lactobacillus johnsonii Strain N6.2 and Lacctobacillus reuteri Strain TD1", Genome Announcements, vol. 2 No. 3, May 8, 2014.
Li Xia et al: "Varied transcriptional efficiencies of multiple *Arabidopsis* U6 small nuclear RNA genes", Journal of Integrative Plant Biology,Feb. 2007, pp. 222-229, vol. 49 No. 2.
Li et al., "In vivo genome editing restores hemostasis in a mouse model of hemophilia", Nature, 2011, pp. 217-221, vol. 475 No. 7355.
Li et al. High-efficiency TALEN-based gene editing produces disease-resistant rice. Nat Biotechnol. May 7, 2012, pp. 390-392, vol. 30 No. 5.
Jian-Feng Li et al., Multiplex and homologous recombination—mediated genome editing in *Arabidopsis* and Nicotiana benthamiana using guide RNA and Cas9, Nature Biotechnology, Aug. 2013, pp. 688-691, vol. 31, No. 8 (and supplemental).
Li, "Comparative Analysis of the Base Compositions of the Pre-mRNA 3' Cleaved-Off Region and the mRNA 3' Untranslated Region Relative to the Genomic Base Composition in Animals and Plants" PLOS One, Jun. 2014, vol. 9 Issue 6, e99928.
Li Zhongsen et al: "Cas9-guide RNA directed genome editing in soybean", Plant Physiology, vol. 169 No. 2, Oct. 2015, pp. 960-970, XP002765282.
Michael R. Lieber et al., The Mechanism of Double-Strand DNA Break Repair by the Nonhomologous DNA End Joining Pathway, Annu Rev Biochem, 2010, pp. 181-211, vol. 79.
Song Luo, et al: "Non-transgenic plant genome editing using purified sequence-specific nucleases", Mol Plant, vol. 8, Jun. 11, 2015, 1425-1427.
Ming Ma et al., A Guide RNA Sequence Design Platform for the CRISPR/Cas9 System for Model Organism Genomes, BioMed Research International, 2013, 4 pages, Article ID 270805.
Morgan L. Maeder et al., CRISPR RNA-guided activation of endogenous human genes, Nature Methods, Oct. 2013, pp. 977-979, vol. 10, No. 10.
Kira S. Makarova et al., Evolution and classification of the CRISPR-Cas systems, Nat Rev Microbiol, Jun. 2011, pp. 467-477, vol. 9(6).
Prashant Mali et al., RNA-Guided Human Genome Engineering via Cas9, Sciencexpress, Feb. 15, 2013, pp. 823-826, vol. 15, 339(6121).
Prashant Mali et al., CAS9 transcriptional activators for target specificity screening and paired nickases for cooperative genome engineering, Nat. Biotechnol., Sep. 2013, pp. 833-838, vol. 31(9).
Zhiyong Mao et al., Comparison of nonhomologous end joining and homologous recombination in human cells, DNA Repair, 2008, 7:1765-1771.
Yanfei Mao et al., Application of the CRISPR-Cas System for Efficient Genome Engineering in Plants, Molecular Plant, Nov. 2013, pp. 2008-2011, vol. 6, No. 6.
Luciano A. Marraffini et al., CRISPR Interference Limits Horizontal Gene Transfer in Staphylococci by Targeting DNA, Science, Dec. 19, 2008, pp. 1843-1845, vol. 322(5909).
Luciano A. Marraffini et al., CRISPR interference: RNA-directed adaptive immunity in bacteria and archaea, Nat Rev Genet, Mar. 2010, pp. 181-190, vol. 11(3).
Susana Martin-Ortigosa et al: "Mesoporous silica nanoparticle-mediated intracellular Cre protein delivery for maize genome editing via IoxP sigte excision", Plant Physio, vol. 164, Issue 2, Feb. 2014, pp. 537-547.
Susana Martin-Ortigosa et al: "Proteolistics: a biolistic method for intracellular delivery of proteins", Transgenic Res, vol. 23, Aug. 5, 2014, pp. 743-756.
Jin Miao et al., Targeted mutagenesis in rice using CRISPR-Cas System, Cell Research, 2013, pp. 1233-1236, vol. 23.
Jeffrey C. Miller et al., A TALE nuclease architecture for efficient genome editing, Nature Biotechnology, Feb. 2011, pp. 143-148, vol. 29.
F. J. Mojica et al., Biological significance of a family of regularly spaced repeats in the genomes of Archaea, Bacteria and mitochondria, Molecular Microbiology, May 2000, pp. 244-246, vol. 36.

\* cited by examiner

FIG. 2

QC795A, 3365 bp

QC819A, 1131 bp

GM-U6-13.1D43

GM-U6-9.1D43

GM-U6-16.1D43

GM-U6-16.2D43

QC799A, 6611 bp

RTW831A, 5719 bp

FIG. 6

```
                       DD43CR1 target site
                                          ↓
DD43CR1_Target   AGCCTTACAACTCACAAGTCCCTTGTACTTGTACGTA|CGG|AGGGTATTCTAGAAAAGAGG
3475_12_1c       AGCCTTACAACTCACAAGTCCCTTGTACTTGTACGTA-----TACGGAGGGTATTCTAGAAAAGAGG
3475_5_6c        AGCCTTACAACTCACAAGTCCCTTGTACTTGTAC-----TACGGAGGGTATTCTAGAAAAGAGG
3475_5_3a        AGCCTTACAACTCACAAGTCCCTTGTACTTGTA-----GTACGGAGGGTATTCTAGAAAAGAGG
3475_12_4c       AGCCTTACAACTCACAAGTCCCTTGTACTTGT-----GTACGGAGGGTATTCTAGAAAAGAGG
3475_1_20b       AGCCTTACAACTCACAAGTCCCTTGTACTTG---CGTACGGAGGGTATTCTAGAAAAGAGG
3478_5_1a        AGCCTTACAACTCACAAGTCCCTTGTACTTG-----GTACGGAGGGTATTCTAGAAAAGAGG
3475_5_1a        AGCCTTACAACTCACAAGTCCCTTGTACTT-----TACGGAGGGTATTCTAGAAAAGAGG
3478_12_4b       AGCCTTACAACTCACAAGTCCCTTGTACTT-----GTACGGAGGGTATTCTAGAAAAGAGG
3475_5_11b       AGCCTTACAACTCACAAGTCCCTTGTACT-----TACGGAGGGTATTCTAGAAAAGAGG
3475_5_4a        AGCCTTACAACTCACAAGTCCCCTTGTA-----GTACGGAGGGTATTCTAGAAAAGAGG
3475_12_2a       AGCCTTACAACTCACAAGTCCCTTGTA-----TACGGAGGGTATTCTAGAAAAGAGG
3475_5_14a       AGCCTTACAACTCACAAGTCCCTTGT-----GTACGGAGGGTATTCTAGAAAAGAGG
3475_1_17a       AGCCTTACAACTCACAAGTCCCTTG-----TACGGAGGGTATTCTAGAAAAGAGG
3475_5_16c       AGCCTTACAACTCACAAGTCCCTT-----TACGGAGGGTATTCTAGAAAAGAGG
3478_8_1a        AGCCTTACAACTCACAAGTCCCT-----TACGGAGGGTATTCTAGAAAAGAGG
3475_5_5c        AGCCTTACAACTCACAAGTCCC-----GGAGGGTATTCTAGAAAAGAGG
3475_5_1b        AGCCTTACAACTCACAAGTCCCCTTGTACTTGTA-----AGAAAAGAGG
3478_6_7c        AGCCTTACAACTCACAAGTCC-----TAAATTAA^AGGTTATTCTAGAAAAGAGG Insertion starts at ^ with the insert size indicated.

3475_1_10a       AGCCTTACAACTCACAAGTCCCTTGTACTTGTAC^167GTACGG|AGGGTATTCTAGAAAAGAGG
3475_1_10c       AGCCTTACAACTCACAAGTCCCTTGTACTTGTA^38-----GTACGGAGGGTATTCTAGAAAAGAGG
3475_5_16a       AGCCTTACAACTCACAAGTCCCTTGTA^130-----GTACGGAGGGTATTCTAGAAAAGAGG
3475_5_3b        AGCCTTACAACTCACAAGTCCCTTGTACTTGTAC^171GTACGGAGGGTATTCTAGAAAAGAGG
3475_1_11a       AGCCTTACAACTCACAAGTCCCTTGTACTTGTAC^220GTACGGAGGGTATTCTAGAAAAGAGG
3478_1_9b        AGCCTTACAACTCACAAGTCCCTTGTACTTGTAC^190GTACGGAGGGTATTCTAGAAAAGAGG
3478_1_9a        AGCCTTACAACTCACAAGTCCCTT^110-----GTACGGAGGGTATTCTAGAAAAGAGG
3478_5_4b        AGCCTTACAACTCACAAGTCCCTTGTACTTGTAC^125GTACGGAGGGTATTCTAGAAAAGAGG
3478_9_1c        AGCCTTACAACTCACAAGTCCCTTGTACTTGTAC^154GTACGGAGGGTATTCTAGAAAAGAGG
3478_9_1a        AGCCTTACAACTCACAAGTCCCTTGTACTTGTA^177-----GAGGGTATTCTAGAAAAGAGG
```

SOYBEAN U6 SMALL NUCLEAR RNA GENE PROMOTERS AND THEIR USE IN CONSTITUTIVE EXPRESSION OF SMALL RNA GENES IN PLANTS

CROSS-REFERENCE

This application claims the benefit of PCT Application Serial Number PCT/US16/23374, filed Mar. 21, 2016, which claims benefit of U.S. Provisional Application Ser. No. 62/139,075, filed Mar. 27, 2015, both of which are incorporated herein in their entirety by reference.

FIELD

This disclosure relates to a plant U6 small nuclear RNA (snRNA) gene promoters and fragments thereof and their use in altering expression of at least one heterologous nucleotide sequence in plants in a tissue-independent or constitutive manner.

REFERENCE TO SEQUENCE LISTING SUBMITTED ELECTRONICALLY

The official copy of the sequence listing is submitted electronically via EFS-Web as an ASCII formatted sequence listing with a file named BB2332USPCT_—SequenceListing.txt created on 22 Aug. 2017 and having a size of 69,295 bytes and is filed concurrently with the specification. The sequence listing contained in this ASCII formatted document is part of the specification and is herein incorporated by reference in its entirety.

BACKGROUND

Recent advances in plant genetic engineering have opened new doors to engineer plants to have improved characteristics or traits, such as plant disease resistance, insect resistance, herbicidal resistance, yield improvement, improvement of the nutritional quality of the edible portions of the plant, and enhanced stability or shelf-life of the ultimate consumer product obtained from the plants. Recombinant DNA technology has made it possible to insert DNA sequences at targeted genomic locations and/or modify (edit) specific endogenous chromosomal sequences, thus altering the organism's phenotype. Site-specific integration techniques, which employ site-specific recombination systems, as well as other types of recombination technologies, have been used to generate targeted insertions of genes of interest in a variety of organism. It is important that appropriate regulatory signals must be present in proper configurations in order to obtain the expression of the desired nucleotide sequences in the plant cell. These regulatory signals typically include a promoter region, a 5' non-translated leader sequence and a 3' transcription termination/polyadenylation sequence.

A promoter is a non-coding genomic DNA sequence, usually upstream (5') to the relevant coding sequence, to which RNA polymerase binds before initiating transcription. This binding aligns the RNA polymerase so that transcription will initiate at a specific transcription initiation site. A promoter includes a nucleic acid fragment capable of controlling transcription of another nucleic acid fragment. A promoter is capable of controlling the expression of a coding sequence or functional RNA. Functional RNA includes, but is not limited to, crRNA, tracerRNA, transfer RNA (tRNA) and ribosomal RNA (rRNA). It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters" if the promoters direct RNA synthesis preferably in certain tissues but also in other tissues at reduced levels. Since patterns of expression of a chimeric gene (or genes) introduced into a plant are controlled using promoters, there is an ongoing interest in the isolation of novel promoters which are capable of controlling the expression of a chimeric gene or (genes) at certain levels in specific tissue types or at specific plant developmental stages.

Certain promoters are able to direct RNA synthesis at relatively similar levels across all tissues of a plant. These are called "constitutive promoters" or "tissue-independent" promoters. Constitutive promoters can be divided into strong, moderate and weak according to their effectiveness to direct RNA synthesis. Since it is necessary in many cases to simultaneously express a chimeric gene (or genes) in different tissues of a plant to get the desired functions of the gene (or genes), constitutive promoters are especially useful in this consideration.

Though many constitutive promoters have been discovered from plants and plant viruses and characterized, there is still an ongoing interest in the isolation of more novel constitutive promoters, especially promoters which are capable of controlling the expression functional RNA molecules.

SUMMARY

This disclosure concerns a recombinant DNA construct comprising at least one heterologous nucleotide sequence operably linked to a promoter wherein said promoter comprises the nucleotide sequence set forth in SEQ ID NOS: 1, 2, 3, 4, 6, 8, 10, 12, 14, 16, 18, 20, 22, 24, 26, 28, 30, 32, 34, 35, 38, 40, or said promoter comprises a functional fragment of the nucleotide sequence set forth in SEQ ID NOS: 1, 2, 3, 4, 6, 8, 10, 12, 14, 16, 18, 20, 22, 24, 26, 28, 30, 32, 34, 35, 38, 40, or wherein said promoter comprises a nucleotide sequence having at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity, based on the Clustal V method of alignment with pairwise alignment default parameters (KTUPLE=2, GAP PENALTY=5, WINDOW=4 and DIAGONALS SAVED=4), when compared to the nucleotide sequence of SEQ ID NOs: 1, 2, 3, 4, 6, 8, 10, 12, 14, 16, 18, 20, 22, 24, 26, 28, 30, 32, 34, 35, 38, 40.

In one embodiment, this disclosure concerns a recombinant DNA construct comprising a nucleotide sequence comprising any of the sequences set forth in SEQ ID NOs: 1, 2, 3, 4, 6, 8, 10, 12, 14, 16, 18, 20, 22, 24, 26, 28, 30, 32, 34, 35, 38, 40, or a functional fragment thereof, operably linked to at least one heterologous sequence, wherein said nucleotide sequence is a constitutive promoter.

In one embodiment, this disclosure concerns a recombinant DNA construct comprising a nucleotide sequence having at least 95% identity, based on the Clustal V method of alignment with pairwise alignment default parameters (KTUPLE=2, GAP PENALTY=5, WINDOW=4 and DIAGONALS SAVED=4), when compared to the sequence set forth in SEQ ID NOs: 1, 2, 3, 4, 6, 8, 10, 12, 14, 16, 18, 20, 22, 24, 26, 28, 30, 32, 34, 35, 38, 40, In one embodiment, this disclosure concerns a recombinant DNA construct comprising at least one heterologous nucleotide sequence operably linked to the promoter of the disclosure.

In one embodiment, this disclosure concerns a cell, plant, or seed comprising a recombinant DNA construct of the present disclosure.

In one embodiment, this disclosure concerns plants comprising this recombinant DNA construct and seeds obtained from such plants.

In one embodiment, this disclosure concerns a recombinant DNA construct

BRIEF DESCRIPTION OF THE DRAWINGS AND SEQUENCE LISTINGS

The disclosure can be more fully understood from the following detailed description and the accompanying drawings and Sequence Listing that form a part of this application.

FIG. 1 is the phylogenetic tree of eighteen U6 snRNA genes found in soybean based on their sequences similarity (genes are indicated by GM-U6-1.1, GM-U6-4.1, GM-U6-4.2, GM-U6-6.1, GM-U6-9.1, GM-U6-12.1, GM-U6-13.1, GM-U6-14.1, GM-U6-15.1, GM-U6-15.2, GM-U6-16.1, GM-U6-16.2, GM-U6-19.1, GM-U6-19.2, GM-U6-19.3, GM-U6-19.4, GM-U6-19.5 and GM-U6-19.6). The first number indicates the chromosome the gene is located and the second number indicates the numbers of U6 snRNA on the chromosome. For example, GmU6-9.1 means first U6 snRNA on chromosome 9.

Figure 2:
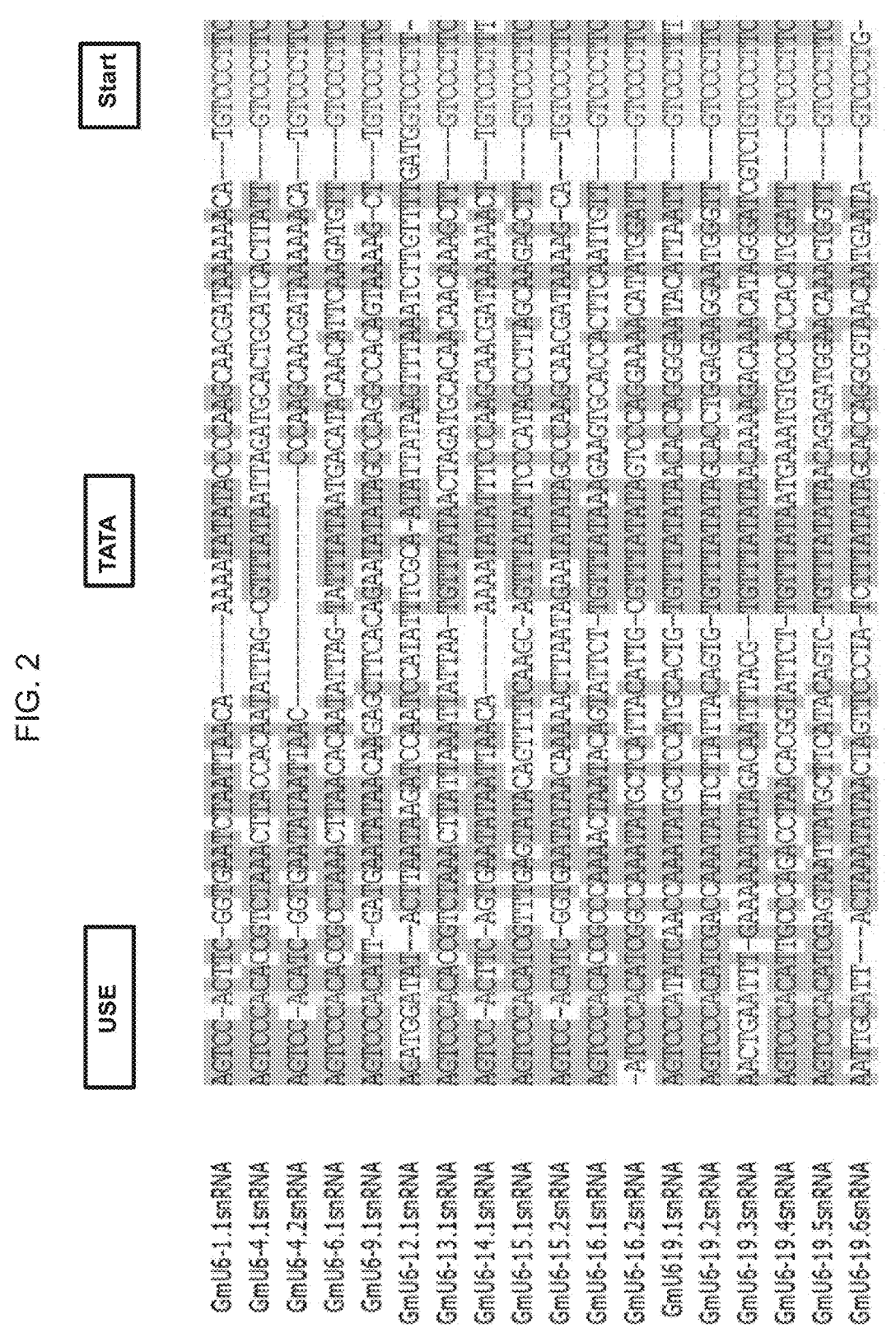

FIG. 2 is the alignment of the proximate promoter regions of eighteen soybean U6 snRNA genes (GM-U6-1.1 snRNA, SEQ ID NO: 6; GM-U6-4.1 snRNA, SEQ ID NO: 8; GM-U6-4.2 snRNA, SEQ ID NO: 10; GM-U6-6.1 snRNA, SEQ ID NO: 12; GM-U6-9.1 snRNA, SEQ ID NO: 14; GM-U6-12.1 snRNA, SEQ ID NO: 16; GM-U6-13.1 snRNA, SEQ ID NO: 18; GM-U6-14.1 snRNA, SEQ ID NO: 20; GM-U6-15.1 snRNA, SEQ ID NO: 22; GM-U6-15.2 snRNA, SEQ ID NO: 24; GM-U6-16.1 snRNA, SEQ ID NO: 26; GM-U6-16.2 snRNA, SEQ ID NO: 28; GM-U6-19.1 snRNA, SEQ ID NO: 30; GM-U6-19.2 snRNA, SEQ ID NO: 32; GM-U6-19.3 snRNA, SEQ ID NO: 34; GM-U6-19.4 snRNA, SEQ ID NO: 36; GM-U6-19.5 snRNA, SEQ ID NO: 38; GM-U6-19.6 snRNA, SEQ ID NO: 40). The conserved upstream sequence elements (USE), TATA boxes, and snRNA start regions are boxed.

Figure 3A:
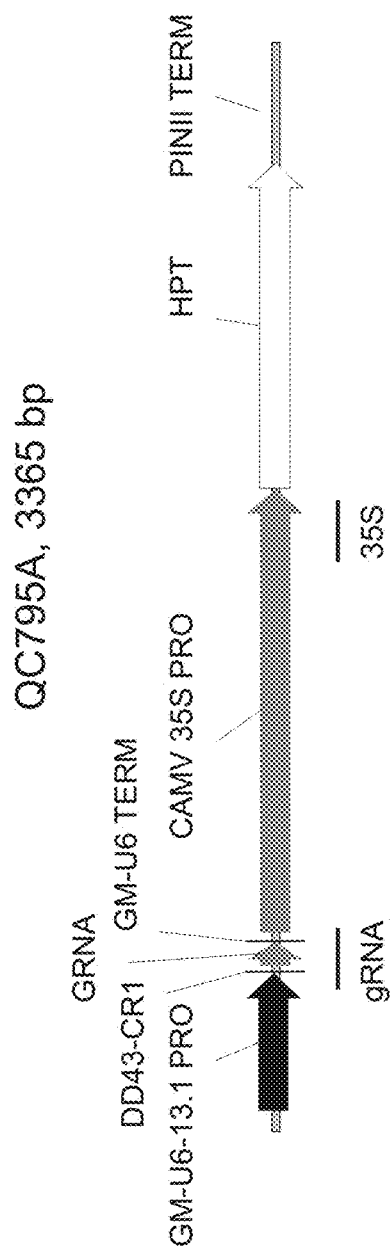
Figure 3B:
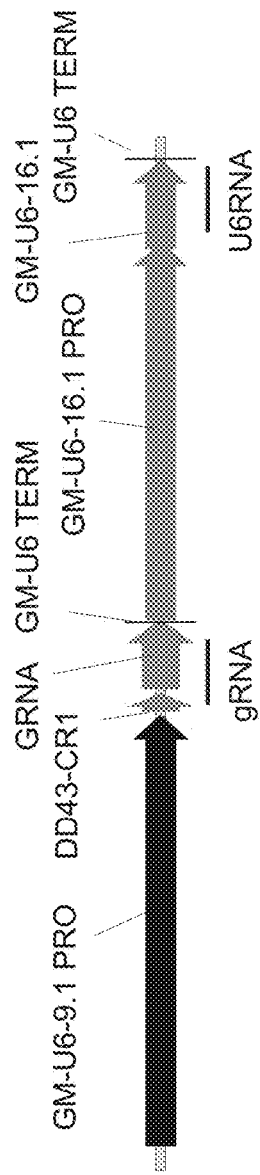

FIG. 3A-3B shows the fragment maps of plasmids QC795, and QC819. FIG. 3A shows the fragment map of QC795 that contains two expression cassettes. The GM-U6-13.1 PRO:DD43CR1 GRNA:GM-U6 RNA TERM cassette is used to test GM-U6-13.1 promoter expressing DD43CR1 GRNA that can be quantified by GRNA specific qRT-PCR. The CAMV 35S PRO:HPT:PINII TERM cassette is used for expressing a selectable marker and event selection. FIG. 3B shows the fragment map of QC819 (a control plasmid) containing GRNA and U6RNA PCR amplicon sequences to be used as controls in qRT-PCR analysis.

Figure 4A:
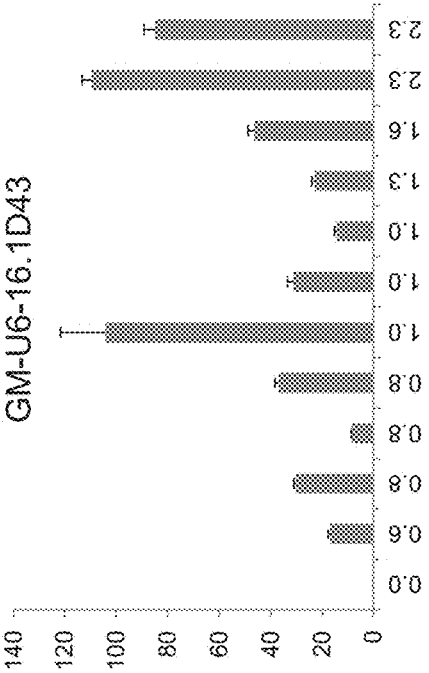
Figure 4C:
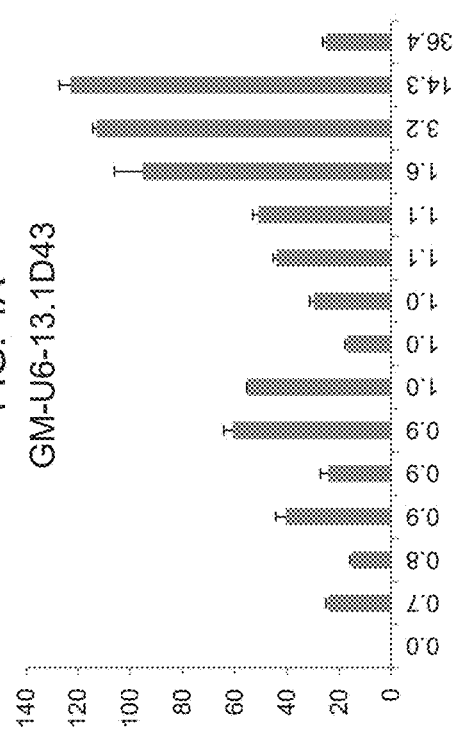
Figure 4B:
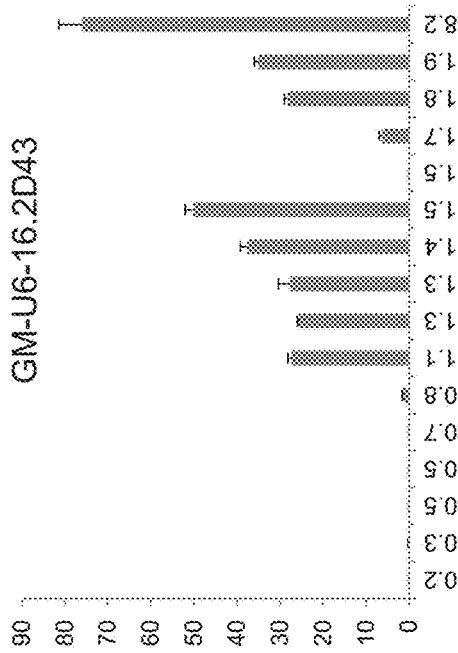
Figure 4D:
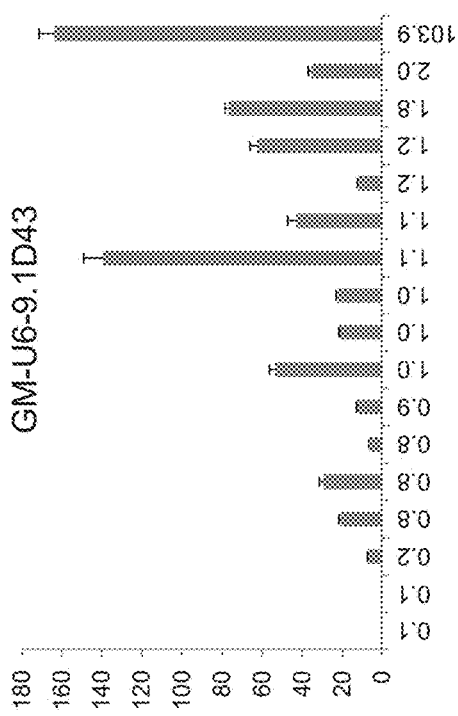

FIG. 4A-4D shows relative expression levels of DD43CR1 guide RNA (D43) expressed by four different soybean U6 gene promoters, GM-U6-13.1 (FIG. 4A), GM-U6-16.1 (FIG. 4B), GM-U6-9.1 (FIG. 4c) and GM-U6-16.2 (FIG. 4D). All the samples were normalized to an endogenous control gene ATP sulfurylase (ATPS) and expressions were compared to a single control. Each column represents an independent event with the qPCR determined copy number of transgenic DD43CR1 GRNA cassette indicated.

Figure 5A:
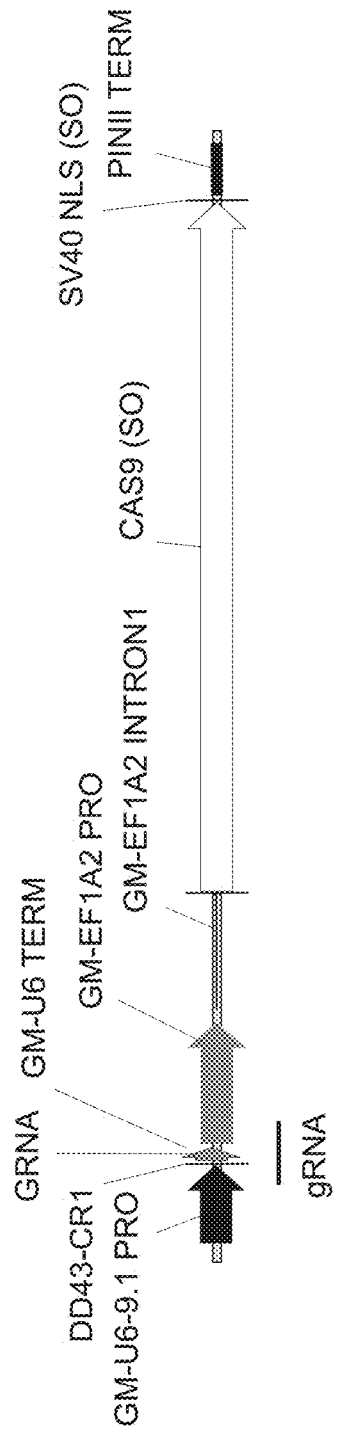
Figure 5B:
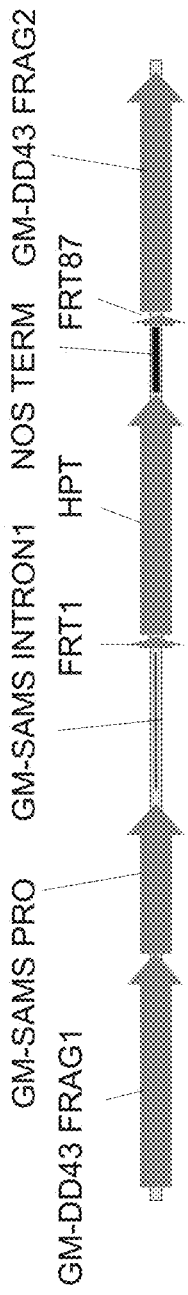

FIG. 5A-5B shows the fragment maps of plasmids QC799, and RTW831. FIG. 5A shows the fragment map of QC799 that contains two expression cassettes. The GM-U6-9.1 PRO:DD43CR1 GRNA:GM-U6 RNA TERM cassette is used to express DD43CR1 guide RNA (GRNA) that will recognize the corresponding DD43 target site in the soybean genome. The GM-EF1A2 PRO:CAS9 (SO):PINII TERM is used to express soybean codon optimized CAS9 protein to cleave a DD43 genomic target site. FIG. 5B shows the fragment map of RTW831 containing the GM-SAMS PRO:HPT:NOS TERM expression cassette for transgenic events selection. Two DNA fragments GM-DD43 FRAG1 and GM-DD43 FRAG2 are homologous to the genomic DNA sequences flanking DD43 site to facilitate homologous recombination.

FIG. 6 is the alignment of DD43CR1 sequences retrieved from independent transgenic events transformed with QC799 and RTW831 to show small sequence deletion and insertions as results of DD43 GRNA/CAS9 mediated DNA repair through non-homologous end joining (NHEJ). The 20 bp DD43 site is in bold followed by the PAM sequence CGG in a box. Small sequence deletions are indicated by "-" while insertions are indicated by "^" followed by a number stating the size of the insertion. (SEQ ID NO:76=3475_12_1c; SEQ ID NO:77=3475_5_6c; SEQ ID NO:78=3475_5_3; SEQ ID NO:79=3475_12_4c; SEQ ID NO:80=3475_1_20b; SEQ ID NO:81=3478_5_1a; SEQ ID NO:82=3475_5_1a; SEQ ID NO:83=3478_12_4b; SEQ ID NO:84=3475_5_11b; SEQ ID NO:85=3475_5_4a; SEQ ID NO:86=33475_12_2a; SEQ ID NO:87=3475_5_14a; SEQ ID NO:88=3475_1_17a; SEQ ID NO:89=3475_5_16c; SEQ ID NO:90=3478_8_1a; SEQ ID NO:91=3475_5_5c; SEQ ID NO:92=3478_5_1b; SEQ ID NO:93=3478_6_7c; SEQ ID NO:94=3475_1_10a; SEQ ID NO:95=3475_1_10c; SEQ ID NO:96=3475_5_16a; SEQ ID NO:97=3475_5_3b; SEQ ID NO:98=3475_1_11a; SEQ ID NO:99=3478_1_9b; SEQ ID NO:100=3478_1_9; SEQ ID NO:101=3478_5_4b; SEQ ID NO:102=3478_9_1c; SEQ ID NO:103=3478_9_1a).

The sequence descriptions summarize the Sequence Listing attached hereto. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219 (2):345-373 (1984).

SEQ ID NO:1 is the GM-U6-9.1 snRNA gene promoter fragment flanked by Xma1 (cccggg) and HindIII (aagctt) restriction sites.

SEQ ID NO:2 is the GM-U6-13.1 snRNA gene promoter fragment flanked by Xma1 (cccggg) and HindIII (aagctt) restriction sites.

SEQ ID NO:3 is the GM-U6-16.1 snRNA gene promoter fragment start with Xma1 (cccggg) restriction site.

SEQ ID NO:4 is the GM-U6-16.2 snRNA gene promoter fragment start with Xma1 (cccggg) restriction site.

SEQ ID NO:5 is the predicted transcript sequence of the U6 snRNA gene GM-U6-1.1.

SEQ ID NO:6 is the predicted promoter sequence of the U6 snRNA gene GM-U6-1.1.

SEQ ID NO:7 is the predicted transcript sequence of the U6 snRNA gene GM-U6-4.1.

SEQ ID NO:8 is the predicted promoter sequence of the U6 snRNA gene GM-U6-4.1.

SEQ ID NO:9 is the predicted transcript sequence of the U6 snRNA gene GM-U6-4.2.

SEQ ID NO:10 is the predicted promoter sequence of the U6 snRNA gene GM-U6-4.2.

SEQ ID NO:11 is the predicted transcript sequence of the U6 snRNA gene GM-U6-6.1.

SEQ ID NO:12 is the predicted promoter sequence of the U6 snRNA gene GM-U6-6.1.

SEQ ID NO:13 is the predicted transcript sequence of the U6 snRNA gene GM-U6-9.1.

SEQ ID NO:14 is the predicted promoter sequence of the U6 snRNA gene GM-U6-9.1.

SEQ ID NO:15 is the predicted transcript sequence of the U6 snRNA gene GM-U6-12.1.

SEQ ID NO:16 is the predicted promoter sequence of the U6 snRNA gene GM-U6-12.1.

SEQ ID NO:17 is the predicted transcript sequence of the U6 snRNA gene GM-U6-13.1.

SEQ ID NO:18 is the predicted promoter sequence of the U6 snRNA gene GM-U6-13.1.

SEQ ID NO:19 is the predicted transcript sequence of the U6 snRNA gene GM-U6-14.1.

SEQ ID NO:20 is the predicted promoter sequence of the U6 snRNA gene GM-U6-14.1.

SEQ ID NO:21 is the predicted transcript sequence of the U6 snRNA gene GM-U6-15.1.

SEQ ID NO:22 is the predicted promoter sequence of the U6 snRNA gene GM-U6-15.1.

SEQ ID NO:23 is the predicted transcript sequence of the U6 snRNA gene GM-U6-15.2.

SEQ ID NO:24 is the predicted promoter sequence of the U6 snRNA gene GM-U6-15.2.

SEQ ID NO:25 is the predicted transcript sequence of the U6 snRNA gene GM-U6-16.1.

SEQ ID NO:26 is the predicted promoter sequence of the U6 snRNA gene GM-U6-16.1.

SEQ ID NO:27 is the predicted transcript sequence of the U6 snRNA gene GM-U6-16.2.

SEQ ID NO:28 is the predicted promoter sequence of the U6 snRNA gene GM-U6-16.2.

SEQ ID NO:29 is the predicted transcript sequence of the U6 snRNA gene GM-U6-19.1.

SEQ ID NO:30 is the predicted promoter sequence of the U6 snRNA gene GM-U6-19.1.

SEQ ID NO:31 is the predicted transcript sequence of the U6 snRNA gene GM-U6-19.2.

SEQ ID NO:32 is the predicted promoter sequence of the U6 snRNA gene GM-U6-19.2.

SEQ ID NO:33 is the predicted transcript sequence of the U6 snRNA gene GM-U6-19.3.

SEQ ID NO:34 is the predicted promoter sequence of the U6 snRNA gene GM-U6-19.3.

SEQ ID NO:35 is the predicted transcript sequence of the U6 snRNA gene GM-U6-19.4.

SEQ ID NO:36 is the predicted promoter sequence of the U6 snRNA gene GM-U6-19.4.

SEQ ID NO:37 is the predicted transcript sequence of the U6 snRNA gene GM-U6-10.5.

SEQ ID NO:38 is the predicted promoter sequence of the U6 snRNA gene GM-U6-19.5.

SEQ ID NO:39 is the predicted transcript sequence of the U6 snRNA gene GM-U6-19.6.

SEQ ID NO:40 is the predicted promoter sequence of the U6 snRNA gene GM-U6-19.6.

SEQ ID NO:41 is the sequence of a genomic site DD43-CR1 that can be recognized through base paring by a specific gRNA and Cas9 complex.

SEQ ID NO:42 is a sense primer used in quantitative PCR analysis of gRNA transgene copy numbers and in quantitative RT-PCR analysis of gRNA transgene expression.

SEQ ID NO:43 is a FAM labeled fluorescent DNA oligo probe used in quantitative PCR analysis of gRNA transgene copy numbers and in quantitative RT-PCR analysis of gRNA transgene expression.

SEQ ID NO:44 is an antisense primer used in quantitative PCR analysis of gRNA transgene copy numbers and in quantitative RT-PCR analysis of gRNA transgene expression.

SEQ ID NO:45 is a sense primer used in quantitative PCR analysis of 35S:HPT transgene copy numbers.

SEQ ID NO:46 is a FAM labeled fluorescent DNA oligo probe used in quantitative PCR analysis of 35S:HPT transgene copy numbers.

SEQ ID NO:47 is an antisense primer used in quantitative PCR analysis of 35S:HPT transgene copy numbers.

SEQ ID NO:48 is a sense primer used in quantitative PCR analysis of HSP, a soybean heat shock protein gene, as an endogenous control.

SEQ ID NO:49 is a VIC labeled fluorescent DNA oligo probe used in quantitative PCR analysis of HSP endogenous control.

SEQ ID NO:50 is an antisense primer used in quantitative PCR analysis of HSP endogenous control.

SEQ ID NO:51 is a sense primer used in quantitative RT-PCR analysis of U6 transgene expression.

SEQ ID NO:52 is a FAM labeled fluorescent DNA oligo probe used in quantitative RT-PCR analysis of U6 transgene expression.

SEQ ID NO:53 is an antisense primer used in quantitative RT-PCR analysis of U6 transgene expression.

SEQ ID NO:54 is a sense primer used in quantitative PCR and RT-PCR analysis of ATPS, a soybean ATP sulfurylase gene, as an endogenous control.

SEQ ID NO:55 is a VIC labeled fluorescent DNA oligo probe used in quantitative PCR and RT-PCR analysis of ATPS as an endogenous control.

SEQ ID NO:56 is an antisense primer used in quantitative PCR and RT-PCR analysis of ATPS as an endogenous control.

SEQ ID NO:57 is the 3365 bp sequence of a plasmid DNA fragment QC795A.

SEQ ID NO:58 is the 1131 bp sequence of a plasmid DNA fragment QC819A.

SEQ ID NO:59 is the 6611 bp sequence of a plasmid DNA fragment QC799A.

SEQ ID NO:60 is the 5719 bp sequence of a plasmid DNA fragment RTW831A.

SEQ ID NO:61 is a sense primer used in quantitative PCR analysis of SAMS:HPT transgene copy numbers.

SEQ ID NO:62 is a FAM labeled fluorescent DNA oligo probe used in quantitative PCR analysis of SAMS:HPT transgene copy numbers.

SEQ ID NO:63 is an antisense primer used in quantitative PCR analysis of SAMS:HPT transgene copy numbers.

SEQ ID NO:64 is a sense primer used in quantitative PCR analysis of Cas9 transgene copy numbers.

SEQ ID NO:65 is a FAM labeled fluorescent DNA oligo probe used in quantitative PCR analysis of Cas9 transgene copy numbers.

SEQ ID NO:66 is an antisense primer used in quantitative PCR analysis of Cas9 transgene copy numbers.

SEQ ID NO:67 is a sense primer used in quantitative PCR analysis of DD43-CR1 copy numbers.

SEQ ID NO:68 is a FAM labeled fluorescent DNA oligo probe used in quantitative PCR analysis of DD43-CR1 copy numbers.

SEQ ID NO:69 is an antisense primer used in quantitative PCR analysis of DD43-CR1 copy numbers.

SEQ ID NO:70 is a sense primer used in the amplification of DD43-CR1 genomic region by PCR.

SEQ ID NO:71 is an antisense primer used in the amplification of DD43-CR1 genomic region by PCR.

SEQ ID NO:72 is a sense primer used to sequence the PCR amplified DD43-CR1 genomic region.

SEQ ID NO:73 is an antisense primer used to sequence the PCR amplified DD43-CR1 genomic region.

SEQ ID NO:74 is the full length sequence of the PCR amplified DD43-CR1 genomic region from a wild type soybean genome.

SEQ ID NO:75 is a partial sequence of the PCR amplified DD43-CR1 genomic region from a wild type soybean genome.

SEQ ID NO:76 is a partial sequence of the PCR amplified DD43-CR1 genomic region that has been modified from a transgenic soybean event.

SEQ ID NO:77 is a partial sequence of the PCR amplified DD43-CR1 genomic region that has been modified from a transgenic soybean event.

SEQ ID NO:78 is a partial sequence of the PCR amplified DD43-CR1 genomic region that has been modified from a transgenic soybean event.

SEQ ID NO:79 is a partial sequence of the PCR amplified DD43-CR1 genomic region that has been modified from a transgenic soybean event.

SEQ ID NO:80 is a partial sequence of the PCR amplified DD43-CR1 genomic region that has been modified from a transgenic soybean event.

SEQ ID NO:81 is a partial sequence of the PCR amplified DD43-CR1 genomic region that has been modified from a transgenic soybean event.

SEQ ID NO:82 is a partial sequence of the PCR amplified DD43-CR1 genomic region that has been modified from a transgenic soybean event.

SEQ ID NO:83 is a partial sequence of the PCR amplified DD43-CR1 genomic region that has been modified from a transgenic soybean event.

SEQ ID NO:84 is a partial sequence of the PCR amplified DD43-CR1 genomic region that has been modified from a transgenic soybean event.

SEQ ID NO:85 is a partial sequence of the PCR amplified DD43-CR1 genomic region that has been modified from a transgenic soybean event.

SEQ ID NO:86 is a partial sequence of the PCR amplified DD43-CR1 genomic region that has been modified from a transgenic soybean event.

SEQ ID NO:87 is a partial sequence of the PCR amplified DD43-CR1 genomic region that has been modified from a transgenic soybean event.

SEQ ID NO:88 is a partial sequence of the PCR amplified DD43-CR1 genomic region that has been modified from a transgenic soybean event.

SEQ ID NO:89 is a partial sequence of the PCR amplified DD43-CR1 genomic region that has been modified from a transgenic soybean event.

SEQ ID NO:90 is a partial sequence of the PCR amplified DD43-CR1 genomic region that has been modified from a transgenic soybean event.

SEQ ID NO:91 is a partial sequence of the PCR amplified DD43-CR1 genomic region that has been modified from a transgenic soybean event.

SEQ ID NO:92 is a partial sequence of the PCR amplified DD43-CR1 genomic region that has been modified from a transgenic soybean event.

SEQ ID NO:93 is a partial sequence of the PCR amplified DD43-CR1 genomic region that has been modified from a transgenic soybean event.

SEQ ID NO:94 is a partial sequence of the PCR amplified DD43-CR1 genomic region that has been modified from a transgenic soybean event.

SEQ ID NO:95 is a partial sequence of the PCR amplified DD43-CR1 genomic region that has been modified from a transgenic soybean event.

SEQ ID NO:96 is a partial sequence of the PCR amplified DD43-CR1 genomic region that has been modified from a transgenic soybean event.

SEQ ID NO:97 is a partial sequence of the PCR amplified DD43-CR1 genomic region that has been modified from a transgenic soybean event.

SEQ ID NO:98 is a partial sequence of the PCR amplified DD43-CR1 genomic region that has been modified from a transgenic soybean event.

SEQ ID NO:99 is a partial sequence of the PCR amplified DD43-CR1 genomic region that has been modified from a transgenic soybean event.

SEQ ID NO:100 is a partial sequence of the PCR amplified DD43-CR1 genomic region that has been modified from a transgenic soybean event.

SEQ ID NO:101 is a partial sequence of the PCR amplified DD43-CR1 genomic region that has been modified from a transgenic soybean event.

SEQ ID NO:102 is a partial sequence of the PCR amplified DD43-CR1 genomic region that has been modified from a transgenic soybean event.

SEQ ID NO:103 is a partial sequence of the PCR amplified DD43-CR1 genomic region that has been modified from a transgenic soybean event.

DETAILED DESCRIPTION

The disclosure of all patents, patent applications, and publications cited herein are incorporated by reference in their entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

In the context of this disclosure, a number of terms shall be utilized.

An "isolated polynucleotide" refers to a polymer of ribonucleotides (RNA) or deoxyribonucleotides (DNA) that is single- or double-stranded, optionally containing synthetic, non-natural or altered nucleotide bases. An isolated polynucleotide in the form of DNA may be comprised of one or more segments of cDNA, genomic DNA or synthetic DNA.

The terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases.

A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

CRISPR loci (Clustered Regularly Interspaced Short Palindromic Repeats) (also known as SPIDRs—SPacer Interspersed Direct Repeats) constitute a family of DNA loci. CRISPR loci consist of short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 by depending on the CRISPR locus (WO2007/025097, published Mar. 1, 2007). Bacteria and archaea have evolved adaptive immune defenses termed clustered regularly interspaced short palindromic repeats (CRISPR)/CRISPR-associated (Cas) systems that use short RNA to direct degradation of foreign nucleic acids (WO2007/025097, published Mar. 1, 2007). The type II CRISPR/Cas system from bacteria employs a crRNA (CRISPR RNA) and tracrRNA (trans-activating CRISPR RNA) to guide the Cas endonuclease to its DNA target.

The crRNA contains a region complementary to one strand of the double strand DNA target and a region that base pairs with the tracrRNA (trans-activating CRISPR RNA) forming a RNA duplex that directs the Cas endonuclease to cleave the DNA target.

Cas gene includes a gene that is generally coupled, associated or close to or in the vicinity of flanking CRISPR loci. The terms "Cas gene", "CRISPR-associated (Cas) gene" are used interchangeably herein. A comprehensive review of the Cas protein family is presented in Haft, et al., (2005) Computational Biology, PLoS Comput Biol 1(6): e60. doi:10.1371/journal.pcbi.0010060. As described therein, 41 CRISPR-associated (Cas) gene families are described, in addition to the four previously known gene families. It shows that CRISPR systems belong to different classes, with different repeat patterns, sets of genes, and species ranges. The number of Cas genes at a given CRISPR locus can vary between species.

The term CRISPR-associated ("Cas") endonuclease herein refers to a protein encoded by a Cas (CRISPR-associated) gene. A Cas endonuclease, when in complex with a suitable RNA component, is capable of cleaving all or part of a specific DNA target sequence in certain embodiments. For example, it is can be capable of introducing a single- or double-strand break in a specific DNA target sequence; it can alternatively be characterized as being able to cleave one or both strands of a specific DNA target sequence. A Cas endonuclease unwinds the DNA duplex at the target sequence and cleaves at least one DNA strand, as mediated by recognition of the target sequence by a crRNA or guide RNA that is in complex with the Cas. Such recognition and cutting of a target sequence by a Cas endonuclease typically occurs if the correct protospacer-adjacent motif (PAM) is located at or adjacent to the 3' end of the DNA target sequence. Alternatively, a Cas protein herein may lack DNA cleavage or nicking activity, but can still specifically bind to a DNA target sequence when complexed with a suitable RNA component. A preferred Cas protein herein is Cas9. (See also, US Patent Application Publication NumbersUS 2015-0082478 A1, published on Mar. 19, 2015 and US 2015-0059010 A1, published on Feb. 26, 2015, both are hereby incorporated in its entirety by reference).

"Cas9" (formerly referred to as Cas5, Csn1, or Csx12) herein refers to a Cas endonuclease of a type II CRISPR system that forms a complex with a crNucleotide and a tracrNucleotide, or with a single guide polynucleotide, for specifically recognizing and cleaving all or part of a DNA target sequence. Cas9 protein comprises an RuvC nuclease domain and an HNH (H—N—H) nuclease domain, each of which cleaves a single DNA strand at a target sequence (the concerted action of both domains leads to DNA double-strand cleavage, whereas activity of one domain leads to a nick). In general, the RuvC domain comprises subdomains I, II and III, where domain I is located near the N-terminus of Cas9 and subdomains II and III are located in the middle of the protein, flanking the HNH domain (Hsu, et al., Cell 157:1262-1278). "Apo-Cas9" refers to Cas9 that is not complexed with an RNA component. Apo-Cas9 can bind DNA, but does so in a non-specific manner, and cannot cleave DNA (Sternberg, et al., Nature 507:62-67). The terms "type II CRISPR system" and "type II CRISPR-Cas system" are used interchangeably herein and refer to a DNA cleavage system utilizing a Cas9 endonuclease in complex with at least one RNA component. For example, a Cas9 can be in complex with a CRISPR RNA (crRNA) and a trans-activating CRISPR RNA (tracrRNA). In another example, a Cas9 can be in complex with a single guide RNA. Thus, crRNA, tracrRNA, and single guide RNA are non-limiting examples of RNA components herein.

In one embodiment, the Cas endonuclease gene is a type II Cas9 endonuclease, such as but not limited to, Cas9 genes listed in SEQ ID NOS: 462, 474, 489, 494, 499, 505, and 518 of WO 2007/025097published Mar. 1, 2007, and incorporated herein by reference. In another embodiment, the Cas endonuclease gene is a plant, maize or soybean optimized Cas9 endonuclease gene. The Cas endonuclease gene can be operably linked to a SV40 nuclear targeting signal upstream of the Cas codon region and a bipartite VirD2 nuclear localization signal (Tinland, et al., (1992) Proc. Natl. Acad. Sci. USA 89:7442-6) downstream of the Cas codon region.

The terms "functional fragment", "fragment that is functionally equivalent" and "functionally equivalent fragment" are used interchangeably herein. These terms refer to a portion or subsequence of the Cas endonuclease sequence of the present disclosure in which the ability to create a single or double-strand break in the target site is retained.

The terms "functional variant", "Variant that is functionally equivalent" and "functionally equivalent variant" are used interchangeably herein. These terms refer to a variant of the Cas endonuclease of the present disclosure in which the ability create a single or double-strand break in the target site is retained. Fragments and variants can be obtained via methods such as site-directed mutagenesis and synthetic construction.

In one embodiment, the Cas endonuclease gene is a plant codon optimized *streptococcus pyogenes* Cas9 gene that can recognize any genomic sequence of the form N(12-30)NGG can in principle be targeted.

The Cas endonuclease can be introduced directly into a cell by any method known in the art, for example, but not limited to transient introduction methods, transfection and/or topical application.

The terms "guide polynucleotide/Cas endonuclease complex", "guide polynucleotide/Cas endonuclease system", "guide polynucleotide/Cas complex", "guide polynucleotide/Cas system" are used interchangeably herein and refer to a guide polynucleotide and Cas endonuclease that are capable of forming a complex, wherein said guide polynucleotide/Cas endonuclease complex can direct the Cas endonuclease to a genomic target site, enabling the Cas endonuclease to introduce a single or double strand break into the genomic target site As used herein, the term "guide polynucleotide", relates to a polynucleotide sequence that can form a complex with a Cas endonuclease and enables the Cas endonuclease to recognize and optionally cleave a DNA target site. The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA" or "gRNA" (See also US Patent Application Publication Numbers US 2015-0082478 A1, published on Mar. 19, 2015 and US 2015-0059010 A1, published on Feb. 26, 2015, both are hereby incorporated in its entirety by reference).

The guide polynucleotide can be a double molecule (also referred to as duplex guide polynucleotide) comprising a crNucleotide sequence and a tracrNucleotide sequence. The crNucleotide includes a first nucleotide sequence domain (referred to as Variable Targeting domain or VT domain) that can hybridize to a nucleotide sequence in a target DNA and a second nucleotide sequence (also referred to as a tracr mate sequence) that is part of a Cas endonuclease recognition (CER) domain. The tracr mate sequence can hybridized to a tracrNucleotide along a region of complementarity and together form the Cas endonuclease recognition domain or CER domain. The CER domain is capable of interacting with a Cas endonuclease polypeptide. The crNucleotide and the tracrNucleotide of the duplex guide polynucleotide can be RNA, DNA, and/or RNA-DNA-combination sequences. In some embodiments, the crNucleotide molecule of the duplex guide polynucleotide is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the cRNA naturally occurring in Bacteria and Archaea. The size of the fragment of the cRNA naturally occurring in Bacteria and Archaea that can be present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the tracrNucleotide is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides. In one embodiment, the RNA that guides the RNA/Cas9 endonuclease complex is a duplexed RNA comprising a duplex crRNA-tracrRNA.

The tracrRNA (trans-activating CRISPR RNA) contains, in the 5'-to-3' direction, (i) a sequence that anneals with the repeat region of CRISPR type II crRNA and (ii) a stem loop-containing portion (Deltcheva, et al., *Nature* 471:602-607). The duplex guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to introduce a single or double strand break into the genomic target site. (See also, US Patent Application Publication Numbers US 2015-0082478 A1, published on Mar. 19, 2015 and US 2015-0059010 A1, published on Feb. 26, 2015, both are hereby incorporated in its entirety by reference).

The guide polynucleotide can also be a single molecule (also referred to as single guide polynucleotide) comprising a crNucleotide sequence linked to a tracrNucleotide sequence. The single guide polynucleotide comprises a first nucleotide sequence domain (referred to as Variable Targeting domain or VT domain) that can hybridize to a nucleotide sequence in a target DNA and a Cas endonuclease recognition domain (CER domain), that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. The single guide polynucleotide being comprised of sequences from the crNucleotide and the tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). The single guide polynucleotide can form a complex with a Cas endonuclease, wherein said guide polynucleotide/Cas endonuclease complex (also referred to as a guide polynucleotide/Cas endonuclease system) can direct the Cas endonuclease to a genomic target site, enabling the Cas endonuclease to introduce a single or double strand break into the genomic target site. (See also US Patent Application Publication Numbers US 2015-0082478 A1, published on Mar. 19, 2015 and US 2015-0059010 A1, published on Feb. 26, 2015, both are hereby incorporated in its entirety by reference).

The term "variable targeting domain" or "VT domain" is used interchangeably herein and includes a nucleotide sequence that can hybridize (is complementary) to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence, that interacts with a Cas endonuclease polypeptide. A CER domain comprises a tracrNucleotide mate sequence followed by a tracrNucleotide sequence. The CER domain can be composed of a DNA sequence, a RNA sequence, a modified DNA sequence, a modified RNA sequence (see, for example, US Patent Application Publication Number US 2015-0059010 A1, published on Feb. 26, 2015, incorporated in its entirety by reference herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

As used herein, the terms "single guide RNA" and "sgRNA" are used interchangeably herein and relate to a synthetic fusion of two RNA molecules, a crRNA (CRISPR RNA) comprising a variable targeting domain (linked to a tracr mate sequence that hybridizes to a tracrRNA), fused to a tracrRNA (trans-activating CRISPR RNA). The single guide RNA can comprise a crRNA or crRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a genomic target site, enabling the Cas endonuclease to introduce a single or double strand break into the genomic target site.

The terms "guide RNA/Cas endonuclease complex", "guide RNA/Cas endonuclease system", "guide RNA/Cas complex", "guide RNA/Cas system", "gRNA/Cas complex", "gRNA/Cas system", "RNA-guided endonuclease", "RGEN" are used interchangeably herein and refer to at least one RNA component and at least one Cas endonuclease that are capable of forming a complex, wherein said guide RNA/Cas endonuclease complex can direct the Cas endonuclease to a genomic target site, enabling the Cas endonuclease to introduce a single or double strand break into the genomic target site. A guide RNA/Cas endonuclease complex herein can comprise Cas protein(s) and suitable RNA component(s) of any of the four known CRISPR systems (Horvath and Barrangou, Science 327:167-170) such as a type I, II, or III CRISPR system. A guide RNA/Cas endonuclease complex in preferred embodiments comprises a Cas9 endonuclease (CRISPR II system) and at least one RNA component (e.g., a crRNA and tracrRNA, or a gRNA).

The guide polynucleotide can be introduced into a cell directly using any method known in the art such as, but not limited to, particle bombardment or topical applications. The guide polynucleotide can also be introduced indirectly into a cell by introducing a recombinant DNA molecule (via methods such as, but not limited to, particle bombardment or *Agrobacterium* transformation) comprising a heterologous nucleic acid fragment encoding a guide polynucleotide, operably linked to a specific promoter that is capable of transcribing the guide RNA in said cell. The specific promoter can be, but is not limited to, a RNA polymerase III promoter, which allow for transcription of RNA with precisely defined, unmodified, 5'- and 3'-ends (DiCarlo, et al., *Nucleic Acids Res.* 41:4336-4343; Ma, et al., *Mol. Ther. Nucleic Acids* 3:e161).

The terms "target site", "target sequence", "target DNA", "target locus", "genomic target site", "genomic target sequence", and "genomic target locus" are used interchangeably herein and refer to a polynucleotide sequence in the genome (including choloroplastic, mitochondrial DNA, plasmid DNA) of a cell at which a single or double-strand break is induced in the cell genome by a Cas endonuclease. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeable herein to refer to a target sequence that is endogenous or native to the genome of a cell and is at the endogenous or native position of that target sequence in the genome of the cell. Cells include, but are not limited to, human, animal, bacterial, fungal, insect, and plant cells as well as plants and seeds produced by the methods described herein.

A "protospacer adjacent motif" (PAM) herein refers to a short sequence that is recognized by a guide polynucleotide/Cas system herein. The sequence and length of a PAM herein can differ depending on the Cas protein or Cas protein complex used, but are typically 2, 3, 4, 5, 6, 7 or 8 nucleotides long, for example.

The guide polynucleotide/Cas endonuclease system can be used in combination with a co-delivered polynucleotide modification template to allow for editing (modification) of a genomic nucleotide sequence of interest. (See also, US Patent Application Publication Number US 2015-0082478 A1, published on Mar. 19, 2015 and WO2015/026886 A1, published on Feb. 26, 2015, both are hereby incorporated in its entirety by reference).

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

In one embodiment, the disclosure describes a method for editing a nucleotide sequence in the genome of a cell, the method comprising providing a guide polynucleotide, a polynucleotide modification template, and at least one Cas endonuclease to a cell, wherein the Cas endonuclease is capable of introducing a single or double-strand break at a target sequence in the genome of said cell, wherein said polynucleotide modification template includes at least one nucleotide modification of said nucleotide sequence. Cells include, but are not limited to, human, animal, bacterial, fungal, insect, and plant cells as well as plants and seeds produced by the methods described herein. The nucleotide to be edited can be located within or outside a target site recognized and cleaved by a Cas endonuclease. In one embodiment, the at least one nucleotide modification is not a modification at a target site recognized and cleaved by a Cas endonuclease. In another embodiment, there are at least 1, 2, 3, 4, 5, 6, 7, 8, 9, 10, 11, 12, 13, 14, 15, 16, 17, 18, 19, 20, 21, 22, 23, 24, 25, 26, 27, 30, 40, 50, 100, 200, 300, 400, 500, 600, 700, 900 or 1000 nucleotides between the at least one nucleotide to be edited and the genomic target site.

In one embodiment, the disclosure describes a method for editing a nucleotide sequence in the genome of a plant cell, the method comprising providing a guide RNA, a polynucleotide modification template, and at least one plant optimized Cas9 endonuclease to a plant cell, wherein the plant optimized Cas9 endonuclease is capable of providing a double-strand break at a moCas9 target sequence in the plant genome, wherein said polynucleotide modification template includes at least one nucleotide modification of said nucleotide sequence.

Genome editing can be accomplished using any method of gene editing available. For example, gene editing can be accomplished through the introduction into a host cell of a polynucleotide modification template (sometimes also referred to as a gene repair oligonucleotide) containing a targeted modification to a gene within the genome of the host cell. The polynucleotide modification template for use in such methods can be either single-stranded or double-stranded. Examples of such methods are generally described, for example, in US Patent Application Publication Number US 2013-0019349.

In some embodiments, gene editing may be facilitated through the induction of a double-stranded break (DSB) in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), and the like. In some embodiments, the introduction of a DSB can be combined with the introduction of a polynucleotide modification template.

The process for editing a genomic sequence combining DSB and modification templates generally comprises: providing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB. Genome editing using DSB-inducing agents, such as Cas9-gRNA complexes, has been described, for example in US Patent Application Publication Number US 2015-0082478 A1, published on Mar. 19, 2015, WO2015/026886 A1 application published on Feb. 26, 2015, PCT/US15/38767 application filed on Jul. 1, 2015, 2014, and PCT/US15/41256 application filed on Jul. 21, 2015, all of which are incorporated by reference herein.

Further uses for guide RNA/Cas endonuclease systems have been described (see, US Patent Application Publication Number US 2015-0082478 A1, published on Mar. 19, 2015; WO2015/026886 A1, published on Feb. 26, 2015; US 2015-0059010 A1, published on Feb. 26, 2015; PCT/US15/38767 application filed on Jul. 1, 2015, and PCT/US15/41256 application filed on Jul. 21, 2015, all of which are incorporated by reference herein) and include but are not limited to modifying or replacing nucleotide sequences of interest (such as a regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest A "soybean U6 promoters", "GM-U6 promoters" or "U6 promoters" are used interchangeably herein, and refer to the promoter of a putative *Glycine max* gene, or a functional fragment thereof, with significant homology to eukaryotic glyceraldehyde-3-phosphate dehydrogenase genes identified in various plant species including soybean that are deposited in National Center for Biotechnology Information (NCBI) database. The term "soybean U6 promoters" includes both a native soybean promoter (or a functional fragment thereof) and an engineered sequence comprising at least a fragment of the native soybean promoter with a DNA linker attached to facilitate cloning. A DNA linker may comprise a restriction enzyme site.

"Promoter" refers to a nucleic acid fragment capable of controlling transcription of another nucleic acid fragment. A promoter is capable of controlling the expression of a coding sequence or functional RNA. Functional RNA includes, but is not limited to, crRNA, tracerRNA, guide RNA, transfer RNA (tRNA) and ribosomal RNA (rRNA). The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene or functional RNA in different tissues or cell types, or at different stages of development, or in response to different environmental conditions. New promoters of various types useful in plant cells are constantly being discovered; numerous examples may be found in the compilation by Okamuro and Goldberg (*Biochemistry of Plants* 15:1-82 (1989)). It is further recognized that since in most cases the exact boundaries of regulatory sequences have not been completely defined, DNA fragments of some variation of the promoter may also have promoter activity.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

"Constitutive promoter" refers to promoters active in all or most tissues or cell types of a plant at all or most developing stages. As with other promoters classified as "constitutive" (e.g., ubiquitin), some variation in absolute levels of expression can exist among different tissues or stages. The term "constitutive promoter" or "tissue-independent" are used interchangeably herein.

The promoter nucleotide sequences and methods disclosed herein are useful in regulating constitutive expression of any heterologous nucleotide sequences (such as but not limited to RNA sequences) in a host plant in order to alter the phenotype of a plant.

A "heterologous nucleotide sequence" refers to a sequence that is not naturally occurring with the plant promoter sequence of the disclosure. While this nucleotide sequence is heterologous to the promoter sequence, it may be homologous, or native, or heterologous, or foreign, to the plant host. However, it is recognized that the instant promoters may be used with their native coding sequences to increase or decrease expression resulting in a change in phenotype in the transformed seed. The terms "heterologous nucleotide sequence", "heterologous sequence", "heterologous nucleic acid fragment", and "heterologous nucleic acid sequence" are used interchangeably herein.

The present disclosure encompasses recombinant DNA constructs comprising functional fragments of the promoter sequences disclosed herein.

A "functional fragment" refer to a portion or subsequence of the promoter sequence of the present disclosure in which the ability to initiate transcription or drive gene expression (such as to produce a certain phenotype) or expression of a functional RNA is retained. Fragments can be obtained via methods such as site-directed mutagenesis and synthetic construction. As with the provided promoter sequences described herein, the functional fragments operate to promote the expression of an operably linked heterologous nucleotide sequence, forming a recombinant DNA construct (also, a chimeric gene). For example, the fragment can be used in the design of recombinant DNA constructs to produce guide RNAs capable of interacting with Cas enducleases and forming a guideRNA/Cas endonuclease complex. Recombinant DNA constructs can be designed for use in co-suppression or antisense by linking a promoter fragment in the appropriate orientation relative to a heterologous nucleotide sequence.

A nucleic acid fragment that is functionally equivalent to the promoter of the present disclosure is any nucleic acid fragment that is capable of controlling the expression of a coding sequence or functional RNA in a similar manner to the promoter of the present disclosure.

In an embodiment of the present disclosure, the promoters disclosed herein can be modified. Those skilled in the art can create promoters that have variations in the polynucleotide sequence. The polynucleotide sequence of the promoters of the present disclosure as shown in 1, 2, 3, 4, 6, 8, 10, 12, 14, 16, 18, 20, 22, 24, 26, 28, 30, 32, 34, 35, 38, 40, may be modified or altered to enhance their control characteristics. As one of ordinary skill in the art will appreciate, modification or alteration of the promoter sequence can also be made without substantially affecting the promoter function. The methods are well known to those of skill in the art. Sequences can be modified, for example by insertion, deletion, or replacement of template sequences in a PCR-based DNA modification approach.

A "variant promoter", as used herein, is the sequence of the promoter or the sequence of a functional fragment of a promoter containing changes in which one or more nucleotides of the original sequence is deleted, added, and/or substituted, while substantially maintaining promoter function. One or more base pairs can be inserted, deleted, or substituted internally to a promoter. In the case of a promoter fragment, variant promoters can include changes affecting the transcription of a minimal promoter to which it is operably linked. Variant promoters can be produced, for example, by standard DNA mutagenesis techniques or by chemically synthesizing the variant promoter or a portion thereof.

Methods for construction of chimeric and variant promoters of the present disclosure include, but are not limited to, combining control elements of different promoters or duplicating portions or regions of a promoter (see, for example, U.S. Pat. Nos. 4,990,607; 5,110,732; and 5,097,025). Those of skill in the art are familiar with the standard resource materials that describe specific conditions and procedures for the construction, manipulation, and isolation of macromolecules (e.g., polynucleotide molecules and plasmids), as well as the generation of recombinant organisms and the screening and isolation of polynucleotide molecules.

The terms "full complement" and "full-length complement" are used interchangeably herein, and refer to a complement of a given nucleotide sequence, wherein the complement and the nucleotide sequence consist of the same number of nucleotides and are 100% complementary.

The terms "substantially similar" and "corresponding substantially" as used herein refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences.

The isolated promoter sequence comprised in the recombinant DNA construct of the present disclosure can be modified to provide a range of constitutive expression levels of the heterologous nucleotide sequence. Thus, less than the entire promoter regions may be utilized and the ability to drive expression of the coding sequence retained. However, it is recognized that expression levels of the mRNA may be decreased with deletions of portions of the promoter sequences. Likewise, the tissue-independent, constitutive nature of expression may be changed.

Modifications of the isolated promoter sequences of the present disclosure can provide for a range of constitutive expression of the heterologous nucleotide sequence. Thus, they may be modified to be weak constitutive promoters or strong constitutive promoters. Generally, by "weak promoter" is intended a promoter that drives expression of a coding sequence at a low level. By "low level" is intended levels about 1/10,000 transcripts to about 1/100,000 transcripts to about 1/500,000 transcripts. Conversely, a strong promoter drives expression of a coding sequence at high level, or at about 1/10 transcripts to about 1/100 transcripts to about 1/1,000 transcripts.

Moreover, the skilled artisan recognizes that substantially similar nucleic acid sequences encompassed by this disclosure are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the disclosure. Estimates of such homology are provided by either DNA-DNA or DNA-RNA hybridization under conditions of stringency as is well understood by those skilled in the art (Hames and Higgins, Eds.; In Nucleic Acid Hybridization; IRL Press: Oxford, U K, 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS was increased to 60° C. Another set of highly stringent conditions uses two final washes in 0.1×SSC, 0.1% SDS at 65° C.

Preferred substantially similar nucleic acid sequences encompassed by this disclosure are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. It is well understood by one skilled in the art that many levels of sequence identity are useful in identifying related polynucleotide sequences. Useful examples of percent identities are those listed above, or also preferred is any integer percentage from 71% to 100%, such as 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%.

A "substantially homologous sequence" refers to variants of the disclosed sequences such as those that result from site-directed mutagenesis, as well as synthetically derived sequences. A substantially homologous sequence of the present disclosure also refers to those fragments of a particular promoter nucleotide sequence disclosed herein that operate to promote the constitutive expression of an operably linked heterologous nucleic acid fragment. These promoter fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. See particularly, Mullis, et al., (1987) *Methods Enzymol.* 155:335-350, and Higuchi, R. In PCR Technology: Principles and Applications for DNA Amplifications; Erlich, H. A., Ed.; Stockton Press Inc.: New York, 1989. Again, variants of these promoter fragments, such as those resulting from site-directed mutagenesis, are encompassed by the compositions of the present disclosure.

"Codon degeneracy" refers to divergence in the genetic code permitting variation of the nucleotide sequence without affecting the amino acid sequence of an encoded polypeptide. Accordingly, the instant disclosure relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) *CABIOS.* 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, (1989) *CABIOS.* 5:151-153; Higgins, et al., (1992) *Comput. Appl. Biosci.* 8:189-191) can be found in the MegAlign™ v6.1 program of the LASERGENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

In one embodiment the % sequence identity is determined over the entire length of the molecule (nucleotide or amino acid).

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, et al., (1993) *J. Mol. Biol.* 215:403-410) and Gapped Blast (Altschul, et al., (1997) *Nucleic Acids Res.* 25:3389-3402). BLASTN refers to a BLAST program that compares a nucleotide query sequence against a nucleotide sequence database.

"Gene" includes a nucleic acid fragment that expresses a functional molecule such as, but not limited to, a specific protein, including regulatory sequences preceding (5' non-coding sequences) and following (3' non-coding sequences) the coding sequence. "Native gene" refers to a gene as found in nature with its own regulatory sequences.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas endonuclease system as disclosed herein. A mutated plant is a plant comprising a mutated gene.

"Chimeric gene" or "recombinant expression construct", which are used interchangeably, includes any gene that is not a native gene, comprising regulatory and coding sequences that are not found together in nature. Accordingly, a chimeric gene may comprise regulatory sequences and coding sequences that are derived from different sources.

"Coding sequence" refers to a DNA sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster, (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, et al., (1989) *Plant Cell* 1:671-680.

"RNA transcript" refers to a product resulting from RNA polymerase-catalyzed transcription of a DNA sequence. When an RNA transcript is a perfect complimentary copy of a DNA sequence, it is referred to as a primary transcript or it may be a RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded by using the Klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcripts accumulation of a target gene (U.S. Pat. No. 5,107,065). The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The terms "initiate transcription", "initiate expression", "drive transcription", and "drive expression" are used interchangeably herein and all refer to the primary function of a promoter. As detailed throughout this disclosure, a promoter is a non-coding genomic DNA sequence, usually upstream (5') to the relevant coding sequence, and its primary function is to act as a binding site for RNA polymerase and initiate transcription by the RNA polymerase. Additionally, there is "expression" of RNA, including functional RNA, or the expression of polypeptide for operably linked encoding nucleotide sequences, as the transcribed RNA ultimately is translated into the corresponding polypeptide.

The term "expression", as used herein, refers to the production of a functional end-product e.g., an mRNA or a protein (precursor or mature).

The term "expression cassette" as used herein, refers to a discrete nucleic acid fragment into which a nucleic acid sequence or fragment can be moved.

Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at posttranscriptional level.

Co-suppression constructs in plants previously have been designed by focusing on overexpression of a nucleic acid sequence having homology to an endogenous mRNA, in the sense orientation, which results in the reduction of all RNA having homology to the overexpressed sequence (see, Vaucheret, et al., (1998) *Plant J.* 16:651-659 and Gura, (2000) *Nature* 404:804-808). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication Number WO 99/53050 published on Oct. 21, 1999; and PCT Publication Number WO 02/00904 published on Jan. 3, 2002). This increases the frequency of co-suppression in the recovered transgenic plants. Another variation describes the use of plant viral sequences to direct the suppression, or "silencing", of proximal mRNA encoding sequences (PCT Publication Number WO 98/36083 published on Aug. 20, 1998). Genetic and molecular evidences have been obtained suggesting that dsRNA mediated mRNA cleavage may have been the conserved mechanism underlying these gene silencing phenomena (Elmayan, et al., (1998) *Plant Cell* 10:1747-1757; Galun, (2005) *In Vitro Cell. Dev. Biol. Plant* 41 (2):113-123; Pickford, et al., (2003) *Cell. Mol. Life Sci.* 60(5):871-882).

As stated herein, "suppression" includes a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in a non-transgenic or wild type cell. The terms "non-transgenic" and "wild type" are used interchangeably herein.

"Altering expression" refers to the production of gene product(s) in transgenic organisms in amounts or proportions that differ significantly from the amount of the gene product(s) produced by the corresponding wild-type organisms (i.e., expression is increased or decreased).

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms.

"Transient transformation" refers to the introduction of a nucleic acid fragment into the nucleus, or DNA-containing organelle, of a host organism resulting in gene expression without genetically stable inheritance.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

The terms "monocot" and "monocotyledonous plant" are used interchangeably herein. A monocot of the current disclosure includes the Gramineae.

The terms "dicot" and "dicotyledonous plant" are used interchangeably herein. A dicot of the current disclosure includes the following families: Brassicaceae, Leguminosae, and Solanaceae.

"Progeny" comprises any subsequent generation of a plant.

A transgenic plant includes, for example, a plant which comprises within its genome a heterologous polynucleotide introduced by a transformation step. The heterologous polynucleotide can be stably integrated within the genome such that the polynucleotide is passed on to successive generations. The heterologous polynucleotide may be integrated into the genome alone or as part of a recombinant DNA construct. A transgenic plant can also comprise more than one heterologous polynucleotide within its genome. Each heterologous polynucleotide may confer a different trait to the transgenic plant. A heterologous polynucleotide can include a sequence that originates from a foreign species, or, if from the same species, can be substantially modified from its native form. Transgenic can include any cell, cell line, callus, tissue, plant part or plant, the genotype of which has been altered by the presence of heterologous nucleic acid including those transgenics initially so altered as well as those created by sexual crosses or asexual propagation from the initial transgenic. The alterations of the genome (chromosomal or extra-chromosomal) by conventional plant breeding methods, by genome editing procedures that do not result in an insertion of a foreign polynucleotide, or by naturally occurring events such as random cross-fertilization, non-recombinant viral infection, non-recombinant bacterial transformation, non-recombinant transposition, or spontaneous mutation are not intended to be regarded as transgenic.

In certain embodiments of the disclosure, a fertile plant is a plant that produces viable male and female gametes and is self-fertile. Such a self-fertile plant can produce a progeny plant without the contribution from any other plant of a gamete and the genetic material contained therein. Other embodiments of the disclosure can involve the use of a plant that is not self-fertile because the plant does not produce male gametes, or female gametes, or both, that are viable or otherwise capable of fertilization. As used herein, a "male sterile plant" is a plant that does not produce male gametes that are viable or otherwise capable of fertilization. As used herein, a "female sterile plant" is a plant that does not produce female gametes that are viable or otherwise capable of fertilization. It is recognized that male-sterile and female-sterile plants can be female-fertile and male-fertile, respectively. It is further recognized that a male fertile (but female sterile) plant can produce viable progeny when crossed with a female fertile plant and that a female fertile (but male sterile) plant can produce viable progeny when crossed with a male fertile plant.

"Transient expression" refers to the temporary expression of often reporter genes such as β-glucuronidase (GUS), fluorescent protein genes ZS-GREEN1, ZS-YELLOW1 N1, AM-CYAN1, DS-RED in selected certain cell types of the host organism in which the transgenic gene is introduced temporally by a transformation method. The transformed materials of the host organism are subsequently discarded after the transient gene expression assay.

Standard recombinant DNA and molecular cloning techniques used herein are well known in the art and are described more fully in Sambrook, et al., In Molecular Cloning: A Laboratory Manual; $2^{nd}$ ed.; Cold Spring Harbor Laboratory Press: Cold Spring Harbor, N.Y., 1989 (hereinafter "Sambrook, et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel, et al., 1990").

"PCR" or "Polymerase Chain Reaction" is a technique for the synthesis of large quantities of specific DNA segments, consisting of a series of repetitive cycles (Perkin Elmer Cetus Instruments, Norwalk, Conn.). Typically, the double stranded DNA is heat denatured; the two primers complementary to the 3' boundaries of the target segment are annealed at low temperature and then extended at an intermediate temperature. One set of these three consecutive steps comprises a cycle.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "recombinant DNA construct" or "recombinant expression construct" is used interchangeably and refers to a discrete polynucleotide into which a nucleic acid sequence or fragment can be moved. Preferably, it is a plasmid vector or a fragment thereof comprising the promoters of the present disclosure. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones, et al., (1985) EMBO J. 4:2411-2418; De Almeida, et al., (1989) Mol. Gen. Genetics 218:78-86), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

Various changes in phenotype are of interest including, but not limited to, modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic characteristics and traits such as yield and heterosis increase, the choice of genes for transformation will change accordingly. General categories of genes of interest include, but are not limited to, those genes involved in information, such as zinc fingers, those involved in communication, such as kinases, and those involved in housekeeping, such as heat shock proteins. More specific categories of transgenes, for example, include, but are not limited to, genes encoding important traits for agronomics, insect resistance, disease resistance, herbicide resistance, sterility, grain or seed characteristics, and commercial products. Genes of interest include, generally, those involved in oil, starch, carbohydrate, or nutrient metabolism as well as those affecting seed size, plant development, plant growth regulation, and yield improvement. Plant development and growth regulation also refer to the development and growth regulation of various parts of a plant, such as the flower, seed, root, leaf and shoot.

Other commercially desirable traits are genes and proteins conferring cold, heat, salt, and drought resistance.

Disease and/or insect resistance genes may encode resistance to pests that have great yield drag such as for example, anthracnose, soybean mosaic virus, soybean cyst nematode, root-knot nematode, brown leaf spot, Downy mildew, purple seed stain, seed decay and seedling diseases caused commonly by the fungi—*Pythium* sp., *Phytophthora* sp., *Rhizoctonia* sp., *Diaporthe* sp. Bacterial blight caused by the bacterium *Pseudomonas syringae* pv. Glycinea. Genes conferring insect resistance include, for example, *Bacillus thuringiensis* toxic protein genes (U.S. Pat. Nos. 5,366,892; 5,747,450; 5,737,514; 5,723,756; 5,593,881; and Geiser, et al., (1986) *Gene* 48:109); lectins (Van Damme, et al., (1994) *Plant Mol. Biol.* 24:825); and the like.

Herbicide resistance traits may include genes coding for resistance to herbicides that act to inhibit the action of acetolactate synthase (ALS), in particular the sulfonylurea-type herbicides (e.g., the acetolactate synthase ALS gene containing mutations leading to such resistance, in particular the S4 and/or HRA mutations). The ALS-gene mutants encode resistance to the herbicide chlorsulfuron. Glyphosate acetyl transferase (GAT) is an N-acetyltransferase from *Bacillus licheniformis* that was optimized by gene shuffling for acetylation of the broad spectrum herbicide, glyphosate, forming the basis of a novel mechanism of glyphosate tolerance in transgenic plants (Castle, et al., (2004) *Science* 304:1151-1154).

Antibiotic resistance genes include, for example, neomycin phosphotransferase (npt) and hygromycin phosphotransferase (hpt). Two neomycin phosphotransferase genes are used in selection of transformed organisms: the neomycin phosphotransferase I (nptI) gene and the neomycin phosphotransferase II (nptII) gene. The second one is more widely used. It was initially isolated from the transposon Tn5 that was present in the bacterium strain *Escherichia coli* K12. The gene codes for the aminoglycoside 3'-phosphotransferase (denoted aph(3')-II or NPTII) enzyme, which inactivates by phosphorylation a range of aminoglycoside antibiotics such as kanamycin, neomycin, geneticin and paroromycin. NPTII is widely used as a selectable marker for plant transformation. It is also used in gene expression and regulation studies in different organisms in part because N-terminal fusions can be constructed that retain enzyme activity. NPTII protein activity can be detected by enzymatic assay. In other detection methods, the modified substrates, the phosphorylated antibiotics, are detected by thin-layer chromatography, dot-blot analysis or polyacrylamide gel electrophoresis. Plants such as maize, cotton, tobacco, *Arabidopsis*, flax, soybean and many others have been successfully transformed with the nptII gene.

The hygromycin phosphotransferase (denoted hpt, hph or aphIV) gene was originally derived from *Escherichia coli*. The gene codes for hygromycin phosphotransferase (HPT), which detoxifies the aminocyclitol antibiotic hygromycin B. A large number of plants have been transformed with the hpt gene and hygromycin B has proved very effective in the selection of a wide range of plants, including monocotyledonous. Most plants exhibit higher sensitivity to hygromycin B than to kanamycin, for instance cereals. Likewise, the hpt gene is used widely in selection of transformed mammalian cells. The sequence of the hpt gene has been modified for its use in plant transformation. Deletions and substitutions of amino acid residues close to the carboxy (C)-terminus of the enzyme have increased the level of resistance in certain plants, such as tobacco. At the same time, the hydrophilic C-terminus of the enzyme has been maintained and may be essential for the strong activity of HPT. HPT activity can be checked using an enzymatic assay. A non-destructive callus induction test can be used to verify hygromycin resistance.

Genes involved in plant growth and development have been identified in plants. One such gene, which is involved in cytokinin biosynthesis, is isopentenyl transferase (IPT). Cytokinin plays a critical role in plant growth and development by stimulating cell division and cell differentiation (Sun, et al., (2003) *Plant Physiol.* 131:167-176).

Calcium-dependent protein kinases (CDPK), a family of serine-threonine kinase found primarily in the plant kingdom, are likely to function as sensor molecules in calcium-mediated signaling pathways. Calcium ions are important second messengers during plant growth and development (Harper, et al., (1993) *Science* 252:951-954; Roberts, et al., (1993) *Curr. Opin. Cell Biol.* 5:242-246; Roberts, et al., (1992) *Annu. Rev. Plant Mol. Biol.* 43:375-414).

Nematode responsive protein (NRP) is produced by soybean upon the infection of soybean cyst nematode. NRP has homology to a taste-modifying glycoprotein miraculin and the NF34 protein involved in tumor formation and hyper response induction. NRP is believed to function as a defense-inducer in response to nematode infection (Tenhaken, et al., (2005) *BMC Bioinformatics* 6:169).

The quality of seeds and grains is reflected in traits such as levels and types of fatty acids or oils, saturated and unsaturated, quality and quantity of essential amino acids, and levels of carbohydrates. Therefore, commercial traits can also be encoded on a gene or genes that could increase for example methionine and cysteine, two sulfur containing amino acids that are present in low amounts in soybeans. Cystathionine gamma synthase (CGS) and serine acetyl transferase (SAT) are proteins involved in the synthesis of methionine and cysteine, respectively.

Other commercial traits can encode genes to increase for example monounsaturated fatty acids, such as oleic acid, in oil seeds. Soybean oil for example contains high levels of polyunsaturated fatty acids and is more prone to oxidation than oils with higher levels of monounsaturated and saturated fatty acids. High oleic soybean seeds can be prepared by recombinant manipulation of the activity of oleoyl 12-desaturase (Fad2). High oleic soybean oil can be used in applications that require a high degree of oxidative stability, such as cooking for a long period of time at an elevated temperature.

Raffinose saccharides accumulate in significant quantities in the edible portion of many economically significant crop species, such as soybean (*Glycine max* L. Merrill), sugar beet (*Beta vulgaris*), cotton (*Gossypium hirsutum* L.), canola (*Brassica* sp.) and all of the major edible leguminous crops including beans (*Phaseolus* sp.), chick pea (*Cicer arietinum*), cowpea (*Vigna unguiculata*), mung bean (*Vigna radiata*), peas (*Pisum sativum*), lentil (*Lens culinaris*) and lupine (*Lupinus* sp.). Although abundant in many species, raffinose saccharides are an obstacle to the efficient utilization of some economically important crop species.

Down regulation of the expression of the enzymes involved in raffinose saccharide synthesis, such as galactinol synthase for example, would be a desirable trait.

In certain embodiments, the present disclosure contemplates the transformation of a recipient cell with more than one advantageous transgene. Two or more transgenes can be supplied in a single transformation event using either distinct transgene-encoding vectors, or a single vector incorporating two or more gene coding sequences. Any two or more transgenes of any description, such as those conferring herbicide, insect, disease (viral, bacterial, fungal, and nematode), or drought resistance, oil quantity and quality, or those increasing yield or nutritional quality may be employed as desired.

Small nuclear RNAs (snRNA) can combine with protein factors to form RNA-protein complex called small nuclear ribonucleoprotein (snRNP). The U1, U2, U4, U5, and U6 snRNAs are the components of major spliceosome involved in RNA intron processing. While the other above mentioned U snRNAs are transcribed by the same RNA polymerase II that transcribes mRNAs, plant U6 snRNA is transcribed by RNA polymerase III that requires a guanosine residue as the start and 4 or more thymidine residues as the terminator. RNA polymerase III is not sensitive to RNA polymerase II-specific inhibitor α-amanitin (Waibel and Filipowicz, (1990) NAR 18:3451-3458). The simple start and termination requirement of RNA polymerase III makes its promoter good tool to express small RNA molecules such as small hairpin RNA (shRNA) for gene expression regulation (Wang, et al., (2008) *RNA* 14:903-913; Kim and Nam, (2013) *Plant Mol. Biol. Rep.* 31:581-593), and guide RNA (gRNA) for genomic modification using the recently characterized bacteria CRISPR (Clustered Regularly Interspaced Short Palindromic Repeats) system (Barrangou, et al., (2007) Sci. 315:1709-1712; Jinek, et al., (2012) Sci. 337: 816-821; Mali, et al., (2013) Sci. 339:823-826; Cong, et al., (2013) Sci. 339:819-823).

This disclosure concerns a recombinant DNA construct comprising a U6 snRNA gene promoter. This disclosure also concerns a recombinant DNA construct comprising a promoter wherein said promoter consists essentially of the nucleotide sequence set forth in SEQ ID NOS: 1, 2, 3, 4, 6, 8, 10, 12, 14, 16, 18, 20, 22, 24, 26, 28, 30, 32, 34, 35, 38, or 40, or a functional fragment of SEQ ID NOS: 1, 2, 3, 4, 6, 8, 10, 12, 14, 16, 18, 20, 22, 24, 26, 28, 30, 32, 34, 35, 38, 40. This disclosure also concerns an isolated polynucleotide comprising a promoter wherein said promoter comprises the nucleotide sequence set forth in SEQ ID NOS: 1, 2, 3, 4, 6, 8, 10, 12, 14, 16, 18, 20, 22, 24, 26, 28, 30, 32, 34, 35, 38, 40, or a functional fragment of SEQ ID NOS: 1, 2, 3, 4, 6, 8, 10, 12, 14, 16, 18, 20, 22, 24, 26, 28, 30, 32, 34, 35, 38 or 40

It is clear from the disclosure set forth herein that one of ordinary skill in the art could perform the following procedure:

1) operably linking the nucleic acid fragment containing the U6 promoter sequence described herein to a nucleotide sequence encoding a suitable functional RNA such as but not limiting to a crRNA, a tracerRNA or a single guide RNA.
2) transforming a chimeric U6 promoter-reporter guide RNA expression cassette into an appropriate plant for expression of the promoter. There are a variety of appropriate plants which can be used as a host for transformation that are well known to those skilled in the art, including the dicots, *Arabidopsis*, tobacco, soybean, oilseed rape, peanut, sunflower, safflower, cotton, tomato, potato, cocoa and the monocots, corn, wheat, rice, barley and palm.
3) testing for expression of the U6 promoter in various cell types of transgenic plant tissues, e.g., leaves, roots, flowers, seeds, transformed with the chimeric U6 promoter-reporter gene expression cassette by assaying for expression of the reporter gene product.

In another embodiment, this disclosure concerns host cells comprising either the recombinant DNA constructs of the disclosure as described herein or isolated polynucleotides of the disclosure as described herein. Examples of host cells which can be used to practice the disclosure include, but are not limited to, yeast, bacteria, and plants.

Plasmid vectors comprising the instant recombinant DNA construct can be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene.

Methods for transforming dicots, primarily by use of *Agrobacterium tumefaciens*, and obtaining transgenic plants have been published, among others, for cotton (U.S. Pat. Nos. 5,004,863, 5,159,135); soybean (U.S. Pat. Nos. 5,569, 834, 5,416,011); Brassica (U.S. Pat. No. 5,463,174); peanut (Cheng, et al., (1996) *Plant Cell Rep.* 15:653-657; McKently, et al., (1995) *Plant Cell Rep.* 14:699-703); *papaya* (Ling, et al., (1991) *Bio/technology* 9:752-758); and pea (Grant, et al., (1995) *Plant Cell Rep.* 15:254-258). For a review of other commonly used methods of plant transformation see, Newell, (2000) *Mol. Biotechnol.* 16:53-65. One of these methods of transformation uses *Agrobacterium rhizogenes* (Tepfler and Casse-Delbart, (1987) *Microbiol. Sci.* 4:24-28). Transformation of soybeans using direct delivery of DNA has been published using PEG fusion (PCT Publication Number WO 92/17598), electroporation (Chowrira, et al., (1995) *Mol. Biotechnol.* 3:17-23; Christou, et al., (1987) *Proc. Natl. Acad. Sci. U.S.A.* 84:3962-3966), microinjection, or particle bombardment (McCabe, et al., (1988) *Biotechnology* 6:923-926; Christou, et al., (1988) *Plant Physiol.* 87:671-674).

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, Calif., 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present disclosure containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see, for example, Sambrook, et al., 1989; Maliga, et al., In Methods in Plant Molecular Biology; Cold Spring Harbor Press, 1995; Birren, et al., In Genome Analysis: Detecting Genes, 1; Cold Spring Harbor: New York, 1998; Birren, et al., In Genome Analysis: Analyzing DNA, 2; Cold Spring Harbor: New York, 1998; Clark, Ed., In Plant Molecular Biology: A Laboratory Manual; Springer: New York, 1997).

The skilled artisan will also recognize that different independent transformation events will result in different levels and patterns of expression of the chimeric genes (Jones, et al., (1985) *EMBO J.* 4:2411-2418; De Almeida, et al., (1989) *Mol. Gen. Genetics* 218:78-86). Thus, multiple events must be screened in order to obtain lines displaying the desired expression level and pattern. Such screening may be accomplished by Northern analysis of mRNA expression, Western analysis of protein expression, or phenotypic analysis. Also of interest are seeds obtained from transformed plants displaying the desired gene expression profile.

The level of activity of the U6 promoter is weaker than that of many known strong promoters, such as the CaMV 35S promoter (Atanassova, et al., (1998) *Plant Mol. Biol.* 37:275-285; Battraw and Hall, (1990) *Plant Mol. Biol.* 15:527-538; Holtorf, et al., (1995) *Plant Mol. Biol.* 29:637-646; Jefferson, et al., (1987) *EMBO J.* 6:3901-3907; Wilmink, et al., (1995) *Plant Mol. Biol.* 28:949-955), the *Arabidopsis* ubiquitin extension protein promoters (Callis, et al., (1990) *J. Biol. Chem.* 265(21):12486-12493), a tomato ubiquitin gene promoter (Rollfinke, et al., (1998) *Gene* 211:267-276), a soybean heat shock protein promoter, and a maize H3 histone gene promoter (Atanassova, et al., (1998) *Plant Mol. Biol.* 37:275-285).

Transformation and selection can be accomplished using methods well-known to those skilled in the art including, but not limited to, the methods described herein.

Non-limiting examples of methods and compositions disclosed herein are as follows:

1. A recombinant DNA construct comprising a nucleotide sequence comprising any one of the sequence set forth in SEQ ID NO: 1, SEQ ID NO: 2, SEQ ID NO: 3, SEQ ID NO: 4, SEQ ID NO: 6, SEQ ID NO: 8, SEQ ID NO: 10, SEQ ID NO: 12, SEQ ID NO: 14, SEQ ID NO:16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, or a functional fragment thereof, operably linked to at least one heterologous sequence, wherein said nucleotide sequence is a promoter.
2. The recombinant DNA construct of embodiment 1, wherein said nucleotide sequence has at least 95% identity, based on the Clustal V method of alignment with pairwise alignment default parameters (KTUPLE=2, GAP PENALTY=5, WINDOW=4 and DIAGONALS SAVED=4), when compared to any one of the sequence set forth in SEQ ID NO: 1, SEQ ID NO: 2, SEQ ID NO: 3, SEQ ID NO: 4, SEQ ID NO: 6, SEQ ID NO: 8, SEQ ID NO: 10, SEQ ID NO: 12, SEQ ID NO: 14, SEQ ID NO:16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38 or SEQ ID NO: 40.
3. A vector comprising the recombinant DNA construct of embodiment 1.
4. A cell comprising the recombinant DNA construct of embodiment 1.
5. The cell of embodiment 4, wherein the cell is a plant cell.
6. A transgenic plant having stably incorporated into its genome the recombinant DNA construct of embodiment 1.
7. The transgenic plant of embodiment 6 wherein said plant is a dicot plant.
8. The transgenic plant of embodiment 7 wherein the plant is soybean.
9. A transgenic seed produced by the transgenic plant of embodiment 7, wherein the transgenic seed comprises the recombinant DNA construct.
10. The recombinant DNA construct of embodiment 1 wherein the at least one heterologous sequence codes for a functional RNA molecule selected from the group consisting of crRNA, tracrRNA and guide-RNA.
11. The recombinant DNA construct of embodiment 1, wherein the at least one heterologous sequence encodes a single guide RNA that is capable of forming a guide RNA/Cas endonuclease complex, wherein said guide-RNA hybridizes to a DNA target site.
12. A method of expressing a functional RNA in a plant comprising:
    a) introducing the recombinant DNA construct of embodiment 1 into the plant, wherein the at least one heterologous sequence encodes a functional RNA;
    b) growing the plant of step a); and
    c) selecting a plant displaying expression of the functional RNA of the recombinant DNA construct.
13. The method of Embodiment 12 wherein the plant is a dicot plant.
14. The method of Embodiment 12 wherein the plant is a soybean plant.
15. A plant stably transformed with a recombinant DNA construct comprising a soybean U6 polymerase III promoter and a heterologous nucleic acid fragment operably linked to said U6 polymerase III promoter, wherein said U6 polymerase III promoter is a capable of controlling expression of said heterologous nucleic acid fragment in a plant cell, and further wherein said U6 polymerase III promoter comprises any of the sequences set forth in SEQ ID NO: 1, SEQ ID NO: 2, SEQ ID NO: 3, SEQ ID NO: 4, SEQ ID NO: 6, SEQ ID NO: 8, SEQ ID NO: 10, SEQ ID NO: 12, SEQ ID NO: 14, SEQ ID NO:16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40.
16. A recombinant DNA construct comprising a soybean U6 polymerase III promoter driving a heterologous nucleic acid fragment encoding a guide polynucleotide, a crRNA, or a tracrRNA, wherein said promoter comprises any of the sequences set forth in SEQ ID NO: 1, SEQ ID NO: 2, SEQ ID NO: 3, SEQ ID NO: 4, SEQ ID NO: 6, SEQ ID NO: 8, SEQ ID NO: 10, SEQ ID NO: 12, SEQ ID NO: 14, SEQ ID NO:16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, or a functional fragment thereof.
17. A method for modifying a target site in the genome of a plant cell, the method comprising introducing a guide RNA and a Cas endonuclease into said plant cell, wherein said guide RNA and Cas endonuclease are capable of forming a complex that enables the Cas endonuclease to introduce a double strand break at said target site, wherein said guide RNA is expressed by a recombinant DNA construct comprising a promoter comprising any of the sequences set forth in SEQ ID NO: SEQ ID NO: 1, SEQ ID NO: 2, SEQ ID NO: 3, SEQ ID NO: 4, SEQ ID NO: 6, SEQ ID NO: 8, SEQ ID NO: 10, SEQ ID NO: 12, SEQ ID NO: 14, SEQ ID NO:16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, or a functional fragment thereof.
18. A recombinant DNA construct comprising a soybean U6 polymerase III promoter driving a heterologous nucleic acid fragment encoding a guide polynucleotide comprising: (i) a first nucleotide sequence domain that is complementary to a nucleotide sequence in a target DNA; and, (ii) a second nucleotide sequence domain that interacts with a Cas endonuclease, wherein the first nucleotide sequence domain and the second nucleotide sequence domain are composed of deoxyribonucleic acids (DNA), ribonucleic acids (RNA), or a combination thereof, wherein the guide polynucleotide does not solely comprises ribonucleic acids.

EXAMPLES

The present disclosure is further defined in the following Examples, in which parts and percentages are by weight and degrees are Celsius, unless otherwise stated. Sequences of promoters, cDNA, adaptors, and primers listed in this disclosure all are in the 5' to 3' orientation unless described otherwise. Techniques in molecular biology were typically performed as described in Ausubel, et al., 1990 or Sambrook, et al., 1989. It should be understood that these Examples, while indicating preferred embodiments of the disclosure, are given by way of illustration only. From the above discussion and these Examples, one skilled in the art can ascertain the essential characteristics of this disclosure, and without departing from the spirit and scope thereof, can make various changes and modifications of the disclosure to adapt it to various usages and conditions. Thus, various modifications of the disclosure in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Identification of Soybean U6 Small Nuclear RNA Genes

Small nuclear RNAs (snRNA) such as U1, U2, U4, U5, and U6 are the components of major spliceosome involved in RNA intron processing. They are combined with protein factors to form RNA-protein complex called snRNPs (small nuclear ribonucleoprotein). While the other above mentioned U snRNAs are transcribed by RNA polymerase II that also transcribes protein-coding mRNAs, plant U6 snRNA is transcribed by RNA polymerase III that starts transcription with a guanosine residue and terminates transcription by 4 or more thymidine residues (Waibel and Filipowicz, (1990) *Nucleic Acids Res.* 18:3451-3458; Li, et al., (2007) *J. Integrate Plant Biol.* 49:222-229; Nielsen, et al., *Science* 340:1577-1580)). RNA polymerase III also synthesizes tRNAs, 5S rRNA, and other types cytoplasmic and nuclear small RNAs. The fact that RNA polymerase III is not sensitive to RNA polymerase II-specific inhibitor α-amanitin is conveniently used to determine if a promoter dependent on RNA polymerase III.

The simple initiation and termination requirements make RNA polymerase III promoters ideal for the precise expression of small RNA molecules such as small hairpin RNA (shRNA) for gene silencing by RNA interference (Wang, et al., (2008) *RNA* 14:903-913; Kim and Nam, (2013) *Plant Mol. Biol. Rep.* 31:581-593), and guide RNA (gRNA) for Cas9/gRNA mediated genome modification (Jinek, et al., (2016) *Science* 337:816-821; Mali, et al., (2013) *Science* 339:823-826; Cong, et al., (2013) *Science* 339:819-823).

U6 RNA is approximately 100 nucleotides long and highly conserved across species. The promoters of several *Arabidopsis* and *Medicago truncatula* U6 genes have been characterized (Li, et al., (2007) *J. Integrate Plant Biol.* 49:222-229; Kim and Nam, (2013) *Plant Mol. Biol. Rep.* 31:581-593). One *Arabidopsis* U6 gene AtU6-1 was used to BLAST search the genome sequence of soybean variety Williams82 (Schmutz, et al., (2010) *Nature* 463:178-183).

As described below, eighteen individual U6 snRNA homologues from soybean were identified located on 10 different chromosomes. Eleven of the U6 snRNA homologues were highly conserved with no more than 2 bp deviations in the 102 bp U6 coding sequence. To help easily identify the homologues, they are herein named according to the chromosomes they are located. For example GM-U6-9.1 indicates one *Glycine max* U6 gene on chromosome 9. The eighteen soybean U6 genes are thus named as GM-U6-1.1, GM-U6-4.1, GM-U6-4.2, GM-U6-6.1, GM-U6-6.1, GM-U6-9.1, GM-U6-12.1, GM-U6-13.1, GM-U6-14.1, GM-U6-15.1, GM-U6-15.2, GM-U6-16.1, GM-U6-16.2, GM-U6-19.1, GM-U6-19.2, GM-U6-19.3, GM-U6-19.4, GM-U6-19.5, and GM-U6-19.6. The transcript sequence of each of the U6 snRNA genes are listed as GM-U6-1.1 snRNA, SEQ ID NO: 5; GM-U6-4.1 snRNA, SEQ ID NO: 7; GM-U6-4.2 snRNA, SEQ ID NO: 9; GM-U6-6.1 snRNA, SEQ ID NO: 11; GM-U6-9.1 snRNA, SEQ ID NO: 13; GM-U6-12.1 snRNA, SEQ ID NO: 15; GM-U6-13.1 snRNA, SEQ ID NO: 17 GM-U6-14.1 snRNA, SEQ ID NO: 19; GM-U6-15.1 snRNA, SEQ ID NO: 21; GM-U6-15.2 snRNA, SEQ ID NO: 23; GM-U6-16.1 snRNA, SEQ ID NO: 25; GM-U6-16.2 snRNA, SEQ ID NO: 27; GM-U6-19.1 snRNA, SEQ ID NO: 29; GM-U6-19.2 snRNA, SEQ ID NO: 31; GM-U6-19.3 snRNA, SEQ ID NO: 33; GM-U6-19.4 snRNA, SEQ ID NO: 35; GM-U6-19.5 snRNA, SEQ ID NO: 37; GM-U6-19.6 snRNA, SEQ ID NO: 39, and the predicted promoter sequence of each of the U6 snRNA genes are listed as GM-U6-1.1 snRNA promoter, SEQ ID NO: 6; GM-U6-4.1 snRNA promoter, SEQ ID NO: 8; GM-U6-4.2 snRNA promoter, SEQ ID NO: 10; GM-U6-6.1 snRNA promoter, SEQ ID NO: 12; GM-U6-9.1 snRNA promoter, SEQ ID NO: 14; GM-U6-12.1 snRNA promoter, SEQ ID NO: 16; GM-U6-13.1 snRNA promoter, SEQ ID NO: 18 GM-U6-14.1 snRNA promoter, SEQ ID NO: 20; GM-U6-15.1 snRNA promoter, SEQ ID NO: 22; GM-U6-15.2 snRNA promoter, SEQ ID NO: 24; GM-U6-16.1 snRNA promoter, SEQ ID NO: 26; GM-U6-16.2 snRNA promoter, SEQ ID NO: 28; GM-U6-19.1 snRNA promoter, SEQ ID NO: 30; GM-U6-19.2 snRNA promoter, SEQ ID NO: 32; GM-U6-19.3 snRNA promoter, SEQ ID NO: 34; GM-U6-19.4 snRNA promoter, SEQ ID NO: 36; GM-U6-19.5 snRNA promoter, SEQ ID NO: 38; GM-U6-19.6 snRNA promoter, SEQ ID NO: 40).

The eighteen soybean U6 snRNA genes including their more diverse proximate promoter regions were compared by sequence alignment using Vector NTI AlignX (Invitrogen). They were grouped according to the phylogenetic tree based on their sequences similarities (FIG. 1). The alignment of the proximate promoter region sequences of the eighteen snRNA genes identified a conserved upstream sequence element (labeled as USE in FIG. 2) and a TATA box (labeled as USE in FIG. 2) in most of the U6 snRNA genes (FIG. 2). Both USE and TATA elements are needed for U6 snRNA transcription. Since U6 promoters also contain less conserved regulatory elements such as distal sequence element (DSE) and proximal sequence element (PSE) that are more upstream to the TATA box or USE element, sequence up to 500 bp upstream of the transcription start site may be necessary to maintain full U6 promoter functions. Furthermore, the proper positioning of the elements relative to each other or the transcription start can also play a role (Waibel and Filipowicz, (1990) *Nucleic Acids Res.* 18:3451-3458; Kim and Nam, (2013) *Plant Mol. Biol. Rep.* 31:581-593).

Example 2

Isolation of Soybean U6 snRNA Gene Promoters

Four U6 genes GM-U6-16.1, GM-U6-16.2, GM-U6-13.1 and GM-U6-9.1, were selected for promoter cloning and evaluation. An approximately 500 bp genomic fragment of the DNA sequence upstream of the U6 snRNA transcription start site GTCCCT was selected as the putative promoter fragment and a restriction site Xma1 CCCGGG was engineered at the 5' end for convenient cloning resulting in the promoter sequences of SEQ ID NOS: 1, 2, 3, 4. Both GM-U6-9.1 and GM-U6-13.1 promoters have a HindIII site at the 3' end while GM-U6-16.1 has an Mfel CAATTG and GM-U6-16.2 has an NdeI site CATATG near their 3' ends. These restriction sites are convenient for subsequent cloning the promoters to express different small RNAs such as different gRNAs for targeted genome modification using the CRISPR system.

One component of a guideRNA/Cas endonuclease complex is the guide RNA that can either consist of a single guide RNA molecule or can comprise a hybrid of a chimeric crRNA and tracrRNA. The guideRNA (gRNA) can form a functional complex with a Cas endonuclease, wherein the guide RNA guides the Cas endonuclease to a genomic target site.

Many soybean genomic targets sites including DD43-CR1 on chromosome 4 (SEQ ID NO:41) have been identified All the four selected U6 gene promoters GM-U6-9.1, GM-U6-13.1, GM-U6-16.1, and GM-U6-16.2 were used to express DD43-CR1 gRNA to test and compare their promoter activities. The small U6 promoter:gRNA expression cassettes were synthesized by GenScript (GenScript USA Inc., 860 Centennial Ave, Piscataway, N.J. 08854,USA) and linked to a plant transformation selection marker gene cassette 35S:HPT by restriction digestions and ligations.

Example 3

Small RNA Gene Expression Constructs and Soybean Transformation

Unique restriction sites Xma1 and NotI were engineered at the 5' end and 3' end respectively when GM-U6-13.1:DD43CR1, GM-U6-16.1:DD43CR1, GM-U6-9.1:DD43CR1 and GM-U6-16.2:DD43CR1 gRNA expression cassettes were synthesized. The above cassettes were cloned into the Xma1 and NotI sites of a 35S:HPT:PINII plant transformation selection marker gene vector to create DNA constructs QC795, QC796, QC797, and QC798 (Table 1). The sequence of linked expression cassettes GM-U6-13.1:DD43-CR1+CAMV-35S PRO:HPT:PINII TERM of QC795A (FIG. 3A) is listed as SEQ ID NO:57. The sequences of linked cassettes of QC796A, QC797A, and QC798A differ from QC795A only in the U6 promoters, i.e., GM-U6-16.1 in QC796A (SEQ ID NO: 3), GM-U6-9.1 in QC797A (SEQ ID NO: 1), and GM-U6-16.2 in QC798A (SEQ ID NO: 4).

soybean cultivar Jack by the method of particle gun bombardment (Klein, et al., (1987) Nature 327:70-73; U.S. Pat. No. 4,945,050) as described in detail below to study the U6 promoters in stably transformed soybean plants.

The same methodology as outlined above for the GM-U6-13.1:DD43-CR1 expression cassette construction and transformation can be used with other heterologous nucleic acid sequences including gRNA targeting different genomic sites, small hairpin RNA (shRNA) and artificial micro RNA (amiRNA) for gene expression regulation and silencing.

Soybean somatic embryos from the Jack cultivar were induced as follows. Cotyledons (~3 mm in length) were dissected from surface sterilized, immature seeds and were cultured for 6-10 weeks in the light at 26° C. on a Murashige and Skoog (MS) media containing 0.7% agar and supplemented with 10 mg/ml 2,4-D (2,4-Dichlorophenoxyacetic acid). Globular stage somatic embryos, which produced secondary embryos, were then excised and placed into flasks containing liquid MS medium supplemented with 2,4-D (10 mg/ml) and cultured in the light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, Calif.). To 50 µl of a 60 mg/ml 1.0 mm gold particle suspension were added (in order): 30 µl of 30 ng/l QC795A DNA fragment GM-U6-13.1:DD43-CR1+CAMV-35S PRO:HPT:PINII TERM or QC796, QC797A, QC798A DNA fragments, 20 µl of 0.1 M spermidine, and 25 µl of 5 M CaCl$_2$. The particle preparation was then agitated for 3 minutes, spun in a centrifuge for 10 seconds and the supernatant removed. The DNA-coated particles were then washed once in 400 µl 100% ethanol and resuspended in 45 1 of 100% ethanol. The DNA/particle suspension was sonicated three times for one second each. Then 5 µl of the DNA-coated gold particles was loaded on each macro carrier disk.

TABLE 1

Transformation of DD43-CR1 GRNA Controlled by Different U6 Small Nuclear RNA Gene Promoters.

| Project | DNA | Genes | Events |
|---|---|---|---|
| U6-13.1D43 | QC795A | GM-U6-13.1:DD43-CR1 + CAMV-35S PRO:HPT:PINII TERM | 26 |
| U6-16.1D43 | QC796A | GM-U6-16.1:DD43-CR1 + CAMV-35S PRO:HPT:PINII TERM | 30 |
| U6-9.1D43 | QC797A | GM-U6-9.1:DD43-CR1 + CAMV-35S PRO:HPT:PINII TERM | 28 |
| U6-16.2D43 | QC798A | GM-U6-16.2:DD43-CR1 + CAMV-35S PRO:HPT:PINII TERM | 26 |

The linked GM-U6-13.1:DD43-CR1+CAMV-35S PRO:HPT:PINII TERM cassette was released with AscI digestion from plasmid QC795 as a DNA fragment, separated from the vector backbone fragment by agarose gel electrophoresis, and purified from the gel with a DNA gel extraction kit (QIAGEN). Similarly, linked GM-U6-16.1:DD43-CR1+CAMV-35S PRO:HPT:PINII TERM, U6-9.1:DD43-CR1+CAMV-35S PRO:HPT:PINII TERM, and U6-16.2:DD43-CR1+CAMV-35S PRO:HPT:PINII TERM cassettes were purified from plasmids QC796, QC797, and QC798 respectively. The purified DNA fragments were transformed to Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 30 µg/ml hygromycin as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 30 µg/ml hygromycin selection agent to increase mass. The embryogenic suspension cultures were then transferred to agar solid MS media plates without 2,4-D supplement to allow somatic embryos to develop. A sample of each event was collected at this stage for quantitative PCR analysis. Numbers of transgenic events produced from the four transformation projects are listed in Table 1.

Cotyledon stage somatic embryos were dried-down (by transferring them into an empty small Petri dish that was seated on top of a 10 cm Petri dish containing some agar gel to allow slow dry down) to mimic the last stages of soybean seed development. Dried-down embryos were placed on germination solid media and transgenic soybean plantlets were regenerated. The transgenic plants were then transferred to soil and maintained in growth chambers for seed production.

Genomic DNA was extracted from somatic embryo samples using DNeasy 96 plant kit (QIAGEN) and analyzed by quantitative PCR using TaqMan universal PCR master mix with a 7500 real time PCR system (Applied Biosystems) with gene-specific primers and FAM-labeled fluorescence probes to check copy numbers of both the U6 promoter:DD43-CR1 gRNA (SEQ ID NOS: 42, 43, 44) and 35S:HPT (SEQ ID NOS:45, 46, 47) expression cassettes (FIG. 3A). The qPCR analysis was done in duplex reactions with a heat shock protein (HSP) gene as the endogenous control (SEQ ID NOS:48, 49, 50) and a transgenic DNA sample with a known single copy of 35S:HPT transgene as the calibrator. The endogenous control HSP probe was labeled with VIC and the target gene U6 promoter:DD43-CR1 gRNA or 35S:HPT probe was labeled with FAM for the simultaneous detection of both fluorescent probes (Applied Biosystems). After 2 minutes incubation at 50° C. to activate the Taq DNA polymerase and 10 min incubation at 95° C. to denature the DNA templates, 40 cycles of 15 seconds at 95° C. and 1 minute at 60° C. were performed. PCR reaction data were captured and analyzed using the sequence detection software provided with the 7500 real time PCR system and the gene copy numbers were calculated using the relative quantification methodology (Applied Biosystems). Transgene copy numbers of the QC795A, QC796A, QC797A, and QC798A transgenic events determined by gRNA qPCR assay are indicated by the numbers under each column representing the event (FIG. 4A-4D).

Controls in qRT-PCR Analysis.

Each column in FIG. 4A-4D represents an independent event with the qPCR determined copy number of transgenic DD43CR1 GRNA cassette indicated. A. GM-U6-13.1 promoter. B. GM-U6-16.1 promoter. C. GM-U6-9.1 promoter. D. GM-U6-16.2 promoter.

Example 4

Expression of DD43-CR1 gRNA with Different U6 Promoters

U6 promoter activities were reflected by the expression levels of DD43-CR1 gRNA in different transgenic events of the four projects (Table 1). The expression levels of DD43-CR1 gRNA were determined by quantitative reverse transcription PCR (qRT-PCR) using SuperScript® III One-Step RT-PCR System with Platinum® Taq DNA Polymerase (Invitrogen). Total RNA was extracted from embryogenic callus samples of the transgenic events using an RNeasy 96 universal tissue kit including a DNase I treatment step to remove any trace amount of DNA (QIAGEN). DNA construct QC819 containing a copy of GM-U6-9.1:DD43-CR1 gRNA and a copy of GM-U6-16.1 U6 snRNA gene (SEQ ID NO: 58) was made to be used as the calibrator for relative quantification of both gRNA and U6 snRNA expression by qRT-PCR (FIG. 3B). A series dilutions of QC819 plasmid DNA spiked with wild type soybean genomic DNA were tested in advance to select the appropriate dilution to be used as the qRT-PCR calibrator.

The expression of DD43-CR1 gRNA was checked by qRT-PCR with the same primers and FAM labeled probe used for gRNA qPCR (SEQ ID NOS:42, 43, 44). A constitutively expressed endogenous gene ATP sulfurylase (ATPS) was used as the endogenous control to normalize samples loading with primers and a VIC labeled probe (SEQ ID NOS: 54, 55, 56). Relative expression of DD43-CR1 gRNA in each sample was compared to the same arbitrary calibrator of QC819 spiked with wild type genomic DNA. The qRT-PCR analysis was done in singleplex reactions with three repeats to compensate for variations. After 30 minutes incubation at 5000 to synthesize the first strand cDNA and 10 min incubation at 95° C. to denature the DNA templates, 40 cycles of 15 seconds at 95° C. and 1 minute at 60° C. were performed. PCR analysis data were captured and calculated for relative quantification using software provided with the 7500 real time PCR (Applied Biosystems).

DD43-CR1 gRNA expression was detected by qRT-PCR in all transgenic events with a few exceptions but not in any non-transgenic events for all the four projects GM-U6-13.1D43 with QC795A (FIG. 4A), GM-U6-16.1D43 with QC796A (FIG. 4B), GM-U6-9.1D43 with QC797A (FIG. 4C), and GM-U6-16.2D43 with QC799A (FIG. 4D) indicating that all four promoters (GM-U6-16.1, GM-U6-16.2, GM-U6-13.1 and GM-U6-9.1) were functional and able to express the guide RNAs. Non-transgenic events are indicated by 0.0 or <0.3 copy of the transgene determined by gRNA-specific qPCR done previously. Large variations were observed among transgenic events of the same project even if the events were of good quality by containing 1 copy or 2 copies of the transgene. But variations among three repeats of the same event were reasonable small indicated by the relative short standard deviation line on top of each data column (FIG. 4A-4D). These results indicate that all four U6 promoters were functional. Since the tested promoters of the GM-U6-13.1 (SEQ ID NO:2, GM-U6-16.1 (SEQ ID NO:3), GM-U6-9.1 (SEQ ID NO:1), and GM-U6-16.2 (SEQ ID NO:4), comprised only a fragment of the native promoters detected in soybean, it is expected that the longer versions of the promoters GM-U6-13.1 (SEQ ID NO:18), GM-U6-16.1 (SEQ ID NO:26), GM-U6-9.1 (SEQ ID NO:14), and GM-U6-16.2 (SEQ ID NO:28) will have similar activities as the short version promoters (SEQ ID NOS: 1, 2, 3, 4). It is also expected that the promoters of other U6 snRNA genes GM-U6-1.1 (SEQ ID NO:12), GM-U6-12.1 (SEQ ID NO:16), GM-U6-14.1 (SEQ ID NO:20), GM-U6-15.1 (SEQ ID NO:22), GM-U6-15.2 (SEQ ID NO:24), GM-U6-19.1 (SEQ ID NO:30), GM-U6-19.2 (SEQ ID NO:32), GM-U6-19.3 (SEQ ID NO:34), GM-U6-19.4 (SEQ ID NO:36), GM-U6-19.5 (SEQ ID NO:38), and GM-U6-19.6 (SEQ ID NO:40) can also be possibly cloned to express transgenic small RNAs such a gRNA. Some of these U6 promoters such as GM-U6-4.2, GM-U6-12.1, GM-U6-19.3, and GM-U6-19.6 may not be as active as the others since they lack highly conserved USE or TATA box (FIG. 2).

Example 5

Cas9 and gRNA Constructs for Targeted Genomic Site Modification

The U6 promoter function was further evaluated by its ability to express functional DD43-CR1 gRNA that in combination with the simultaneous expression of the *Streptococcus pyogenes* CAS9 endonuclease resulted in targeted genomic sites modification. The same GM-U6-9.1:DD43-CR1 gRNA cassette of QC797A was linked to GM-EF1A2:CAS9 (SO) cassette to make DNA construct QC799 (SEQ ID NO:59, FIG. 5A). GM-EF1A2 promoter is a strong constitutive promoter isolated from a soybean elongation factor gene (U.S. Pat. No. 8,697,857). CAS9 (SO) is a codon optimized gene for expression in soybean encoding the *S. pyogenes* Cas9 endonuclease. A SV40 nuclear localization signal (NLS) also codon optimized for soybean expression was added to the Cas9 carboxyl end to help transport the protein to nucleus. Functional DD43-CR1 gRNA and Cas9 can form a gRNA-Cas9 riboprotein complex to recognize and cleave the DD43 target site (SEQ ID NO:41) in soybean genome to produce double stands DNA breaks that will be spontaneously repaired by non-homlogous end joining (NHEJ) or homologous recombination (HR). Mutations or foreign DNA can be introduced to the cleavage site during NHEJ or HR.

A donor DNA construct RTW831 containing a GM-SAMS PRO-FRT1:HPT-FRT87 cassette flanked by approximately 1 kb genomic sequences GM-DD43 FRAG1 and GM-DD43 FRAG2 on each side was built for transgenic events selection (SEQ ID NO:60, FIG. 5B). The GM-SAMS promoter was isolated from a soybean S-adenosyl-methionine synthase gene as a moderate constitutive promoter (U.S. Pat. No. 7,217,858). The FRT1 and FRT87 sites were incorporated in the construct so that the HPT gene once integrated in soybean genome can still be replaced with other transgenes through recombinase mediate cassette exchange (RMCE) (Li, et al., (2009) *Plant Physiol.* 151:1087-1095). The flanking DNA fragments GM-DD43 FRAG1 and GM-DD43 FRAG2, identical to the sequences bordering the DD43-CR1 site in soybean genome, are homologous sequences to facilitate DNA homologous recombination to integrate the donor cassette in the DD43-CR1 site.

QC799A and RTW831A DNA fragments (FIG. 5A-5B) were similarly prepared and used with an equal amount to co-transform a soybean cultivar 93B86 following the same process described in example 3. Young somatic embryo clusters of transgenic events were sampled for genomic DNA extraction using DNeasy 96 plant kit (QIAGEN) and qPCR analyses were done similarly as described in example 3. RTW831A transgene copy numbers were checked by qPCR with primers (SEQ ID NOS:61, 63) and FAM labeled probe (SEQ ID NO:62). QC799A transgene copy numbers were checked by qPCR with primers (SEQ ID NOs:64, 66) and FAM labeled probe (SEQ ID NO:65). The copy numbers of endogenous DD43-CR1 target site were checked by qPCR with primers (SEQ ID NOS:67, 69) and FAM labeled probe (SEQ ID NO:68). The same HSP endogenous control qPCR using primers (SEQ ID NOS:48, 50) and VIC labeled probe (SEQ ID NO:49) was included in duplex reaction for all the above qPCR assays.

Example 6

Genomic Site Modification Directed by gRNA Expressed with a U6 Promoter

Wild type soybean genomic DNA contains two copy of DD43-CR1 target site (SEQ ID NO:41) one on each of the two homologous chromosomes. Any transgenic events derived from QC799A+RTW831A transformation are likely modified at the DD43-CR1 site if the DD43-CR1 copy number, determined by qPCR as described in Example 5, is reduced. Modified DD43-CR1 sites would not be amplified by DD43-CR1 specific qPCR with primers (SEQ ID NOS: 67, 69) and FAM labeled probe (SEQ ID NO:68) since both the forward primer DD43-F (SEQ ID NO:67) and probe DD43-T (SEQ ID NO:68) sequences partially overlapped the DD43-CR1 sequence.

If both copies of DD43-CR1 target site were detected by the qPCR, the site was then not modified and remained as wild type (Wt-Homo). If only one copy or none of DD43-CR1 was detected, one copy (NHEJ-Hemi) or both copies (NHEJ-Null) of the site was then modified by NHEJ. As summarized in Table 2, a total of 263 transgenic events were produced of which 53 events (20.2%) retained the DD43-CR1 wild type sequence, 88 events (33.5%) had one copy of the DD43-CR1 sites modified, and 122 events (46.4%) had both copies of the DD43-CR1 sites modified. Combined up to 80% of the total events were modified at the DD43-CR1 site by NHEJ triggered by DNA double strand breaks cleaved by DD43-CR1 gRNA guided Cas9 endonuclease.

TABLE 2

Genomic Site Modification Mediated by DD43-CR1 gRNA expressed with GM-U6-9.1 Promoter.

| Project | Total event | Wt-Homo | NHEJ-Hemi | NHEJ-Null | HR |
|---|---|---|---|---|---|
| U6-9.1DD43CR1 | 263 | 53 | 88 | 122 | 10 |
| % | | 20.2% | 33.5% | 46.4% | 3.8% |

The genomic DD43-CR1 region was amplified by PCR from wild type and the transgenic events for sequence analysis to evaluate DD43-CR1 target site modifications. Primer DD43-LB is upstream of the GM-DD43 FRAG1 and DD43-RB is downstream of the GM-DD43 FRAG2 so PCR with DD43-LB and DD43-RB primers will not amplify anything from RTW831A transgene (FIG. 5B). PCR cycle conditions were 9400 for 4 minutes; 35 cycles of 9400 for 30 seconds, 6000 for 1 minute, and 6800 for 2 minutes; and a final 6800 for 5 minutes before holding at 4° C. using the Platinum high fidelity Taq DNA polymerase (Invitrogen). The PCR reaction was resolved using agarose gel electrophoresis to identify the right size PCR product representing the expected 2098 bp DD43-CR1 region (SEQ ID NO:74). The PCR fragment was cloned into pCR2.1-TOPO vector by TA cloning (Invitrogen) and multiple clones were sequenced.

DD43-CR1 site modifications happened mostly at the expected Cas9 cleavage site 3 bp upstream of the PAM sequence CGG (SEQ ID NOS:75-103, FIG. 6). Both small deletions of the DD43-CR1 site and short insertions in the cleavage site were observed. The results demonstrated that GM-U6-9.1 promoter was effective to express functional DD43-CR1 gRNA to guide sites-specific genome modification. Other GM-U6 promoters such as GM-U6-13.1, GM-U6-16.1, and GM-U6-16.2 were also successfully used to effectively express various gRNAs targeting different genomic sites. Since many other soybean U6 genes promoter regions contain similar regulatory elements, it is thus expected that other GM-U6 promoters though not yet similarly characterized can also be used to express transgenic small RNA genes.

What is claimed is:

1. A recombinant DNA construct comprising:
   (a) a nucleotide sequence comprising at least 250 contiguous nucleotides of the sequence set forth in SEQ ID NO: 28;or,
   (b) a nucleotide sequence having at least 95% sequence identity to the full length of SEQ ID NO: 28, based on the Clustal V method of alignment with pairwise alignment default parameters (KTUPLE=2, GAP PENALTY=5, WINDOW=4 and DIAGONALS SAVED=4);
   operably linked to at least one heterologous nucleotide sequence, wherein said nucleotide sequence is a promoter.

2. A vector comprising the recombinant DNA construct of claim 1.

3. A cell comprising the recombinant DNA construct of claim 1.

4. The cell of claim 3, wherein the cell is a plant cell.

5. A transgenic plant having stably incorporated into its genome the recombinant DNA construct of claim 1.

6. The transgenic plant of claim 5 wherein said plant is a dicot plant.

7. The transgenic plant of claim 6 wherein the plant is soybean.

8. A transgenic seed produced by the transgenic plant of claim 6, wherein the transgenic seed comprises the recombinant DNA construct.

9. The recombinant DNA construct of claim 1 wherein the at least one heterologous nucleotide sequence codes for a functional RNA molecule selected from the group consisting of crRNA, tracrRNA and guide-RNA.

10. The recombinant DNA construct of claim 1, wherein the at least one heterologous nucleotide sequence encodes a single guide RNA that is capable of forming a guide RNA/Cas endonuclease complex, wherein said guide-RNA hybridizes to a DNA target site.

11. A method of expressing a functional RNA in a plant comprising:
   a) introducing the recombinant DNA construct of claim 1 into the plant, wherein the at least one heterologous nucleotide sequence encodes a functional RNA;
   b) growing the plant of step a); and
   c) selecting a plant displaying expression of the functional RNA of the recombinant DNA construct.

12. The method of claim 11 wherein the plant is a dicot plant.

13. The method of claim 11 wherein the plant is a soybean plant.

14. A method for modifying a target site in the genome of a plant cell, the method comprising introducing a guide RNA and a Cas endonuclease into said plant cell, wherein said guide RNA and Cas endonuclease are capable of forming a complex that enables the Cas endonuclease to introduce a double strand break at said target site, wherein said guide RNA is expressed by a recombinant DNA construct comprising a promoter comprising at least 250 contiguous nucleotides of the sequence set forth in SEQ ID NO: 28.

15. A recombinant DNA construct comprising a soybean U6 polymerase III promoter comprising at least 250 contiguous nucleotides of the sequence set forth in SEQ ID NO:28 , driving a heterologous nucleotide sequence encoding a guide polynucleotide comprising: (i) a first nucleotide sequence domain that is complementary to a nucleotide sequence in a target DNA; and, (ii) a second nucleotide sequence domain that interacts with a Cas endonuclease, wherein the first nucleotide sequence domain and the second nucleotide sequence domain are composed of deoxyribonucleic acids (DNA), ribonucleic acids (RNA), or a combination thereof, wherein the guide polynucleotide does not solely comprises ribonucleic acids.

* * * * *

```
                        SEQUENCE LISTING

<160> NUMBER OF SEQ ID NOS: 103

<210> SEQ ID NO 1
<211> LENGTH: 472
<212> TYPE: DNA
<213> ORGANISM: Glycine max

<400> SEQUENCE: 1
cccgggttaa gagaattgta agtgtgcttt tatatattta aaattaatat attttgaaat      60
gttaaaatat aaaagaaaat tcaatgtaaa ttaaaaataa ataaatgttt aataaagata     120
aattttaaaa cataaaagaa aatgtctaac aagaggatta agatcctgtg ctcttaaatt     180
tttaggtgtt gaaatcttag ccatacaaaa tatattttat taaaaccaag catgaaaaaa     240
gtcactaaag agctatataa ctcatgcagc tagaaatgaa gtgaagggaa tccagtttgt     300
tctcagtcga aagagtgtct atctttgttc ttttctgcaa ccgagttaag caaaatggga     360
atgcgaggta tcttcctttc gttaggggag caccagatgc atagttagtc ccacattgat     420
gaatataaca agagcttcac agaatatata gcccaggcca cagtaaaagc tt            472

<210> SEQ ID NO 2
<211> LENGTH: 440
<212> TYPE: DNA
<213> ORGANISM: Glycine max

<400> SEQUENCE: 2
cccgggtgtg atttagtata aagtgaagta atggtcaaaa gaaaaagtgt aaaacgaagt      60
acctagtaat aagtaatatt gaacaaaata aatggtaaag tgtcagatat ataaaatagg     120
ctttaataaa aggaagaaaa aaaacaaaca aaaaatagg tgcaatgggg cagagcagag      180
tcatcatgaa gctagaaagg ctaccgatag ataaactata gttaattaaa tacattaaaa     240
aatacttgga tctttctctt accctgttta tattgagacc tgaaacttga gagagataca     300
ctaatcttgc cttgttgttt cattccctaa cttacaggac tcagcgcatg tcatgtggtc     360
tcgttcccca tttaagtccc acaccgtcta aacttattaa attattaatg tttataacta     420
gatgcacaac aacaaagctt                                                 440

<210> SEQ ID NO 3
<211> LENGTH: 421
<212> TYPE: DNA
<213> ORGANISM: Glycine max

<400> SEQUENCE: 3
cccgggtgcc agaagtattt cagtttattt tgaaaaatca gaaaaaaaat gtctggaata      60
aaatataata agcgatacta ataataatt gaacaagata aatggtaaaa tgtcaaatca     120
aaactaggct acagagtgca gagcagagtc atgatgaatg acagctagtt ctacttacta     180
caccgattct tgtgtacata aaatatttt aaaataattg aatctttctt tagccagctt     240
tgacaacaat gtacaccgtt cgtacttctt actggtaggc aatgcttctt gtttgctttc     300
ggtggaaggt gtatatactc aacattactt ctttttcagc gtgttttctt acgggagtcc     360
cacaccgccc aaaactaata cagtattctt gtttataaag aagtgcacca cttcaattgt     420
```

| t | 421 |

<210> SEQ ID NO 4
<211> LENGTH: 487
<212> TYPE: DNA
<213> ORGANISM: Glycine max

<400> SEQUENCE: 4

| cccgggtgca aatacaacag tttgaaaata aactgctaag ttgtgaatct caccactaaa | 60 |
| atctattaaa atataatttt aaaagataaa tttgttattc aataataggc ttttaaatat | 120 |
| aggaaaatgc ataatttaac taattaaaga aaataaaaat gcaagtgcgg tgacaagaca | 180 |
| agctagaata aagttgcaaa gaaatgacag ggctacaaaa ggctcaccta cttctggatt | 240 |
| taccaaactt ctgtttgtcc ccatactcca aaaacaaaac cattttttttt tatcttcgtt | 300 |
| tttgtttgct ttgactgtga gttgaggccc aactttctgc ttctgtccga ctctatttga | 360 |
| tgaattttgt ttgcctcctg tgatgtgaag gatgtatcat tgaaagggaa cgtgtctcaa | 420 |
| tgatcccaca tcggccaaat atgctcatta cattgcgttt atatagtccc aggaaaacat | 480 |
| atggatt | 487 |

<210> SEQ ID NO 5
<211> LENGTH: 89
<212> TYPE: DNA
<213> ORGANISM: Glycine max

<400> SEQUENCE: 5

| gtcccttcgg ggacatccga ggaaattgaa agcatggccc ttgcgcaagg atgacacgct | 60 |
| tttatcaaga aatggtccaa tttatttttt | 89 |

<210> SEQ ID NO 6
<211> LENGTH: 956
<212> TYPE: DNA
<213> ORGANISM: Glycine max

<400> SEQUENCE: 6

| aatacaaaga aacaaaacct aaggaatcct aaaggaggaa tttgagagag gttaagtcct | 60 |
| gtgtcttgag agaaaaataa tataatatgg aattatctca attctaagaa tacggtcttt | 120 |
| atctttaatt actagtagta tataggatgg aattttctat atgtaaaact aaatttggat | 180 |
| tcatttgaca ataatattat gcaggcacgg aattcttcaa ttttttaacta tgtggtcaca | 240 |
| cttactacaa taatgaccat tttacgacac acaaactacg acggttaaaa aaaaaacatc | 300 |
| gttgaaagat acacggtaac agtgtagtaa ttttaaagaa tgtatacaat gatggttatt | 360 |
| gaataaccat ttttaatagc gagtttaagg agtacaacga caggttgaca agaccgtcg | 420 |
| tagttgtatt ggtagtacaa agatagtttt ttccttttga ctgtctttga ataagcttac | 480 |
| ttattattcc caaaatcact aataattaag tagcttcctc tccgttgcgc tcgcgtaacc | 540 |
| ttcttctgtt cattgttgtc caacttctgg attccctcga ctgtttgaat tcaatgactc | 600 |
| cctcaaaacc acccgcactc tctgactcaa gctttgacta ggccctttgt ctcttgaatc | 660 |
| tctgcgaagt aacgccaaag cagttcatct gtgaagtctc cgtcaaaggt gtctatgtag | 720 |
| gtaagaaccc ctgtccgtca gttttttgtt ttccttcgat gtggttgaat ctagtttgtt | 780 |
| cttagtcgaa agggtgtcta tttgttgttt tctggaaccg agtgaagaga tcgagttaag | 840 |
| cttaatggga atgtgagata tcttcgtttc gttaaggtag cacctggttt gtagcaagtc | 900 |
| cacttcggtg aatctaatta acaaaaatat ataccccaag caacgataaa aaacat | 956 |

<210> SEQ ID NO 7
<211> LENGTH: 105
<212> TYPE: DNA
<213> ORGANISM: Glycine max

<400> SEQUENCE: 7

```
gtcccttcgg ggacatccga taaaattgga acgatacaga aagattagc atggcccctg    60 cgcaaggatg acacgcacaa atcgagaaat ggtccaaatt ttttt                  105
```

<210> SEQ ID NO 8
<211> LENGTH: 982
<212> TYPE: DNA
<213> ORGANISM: Glycine max

<400> SEQUENCE: 8

```
ttataaatga gataaaattt atagatcaat taatgttttt tttattgtgt accaattttt    60
ttattgatcg aaaaggtaaa atttaggaga gttaaatact cttttcattt ttattaatta   120
gttgtcgttt atggtatttt agtagggtga ctgctttgat aaataaataa caaaggaaaa   180
catatttatc ctaaattaga tgcggataca cattggagat tggctaggaa gaagtcagta   240
gttacaaagt taaatgatc tttaattaat ttttatgcaa caagagacaa gacctgagca    300
ttgttgaaga aacattttag actcataaat ggacatacaa agacaaggca taaaactcct   360
ctgtttaggt ggctggggct atgaccagga taatggagt tggtggtgaa ggatgcttga    420
ggaaggtgga gttgttccag atttagtttt cgacttagat gatgcatgga actggctagt   480
gacgtggatg gtggtaggtt actttcaggt catgatttt tgtttctaaa tgatactcac    540
actcccttcc agttttttt ttttaaactc agctcccttg cttcctccac cggttatcat    600
aatactgaac caaatcaaac attacagtca aggtactatg aatatgaaac ctgaaatcct   660
atgaatgtca taaattatt ttaaataata aatttattta gaataatatt ttttgggta    720 agagttataa aataaaatac aaaaaaaaaa cctaatatca attttcact gactccgttt    780 atattgagac ttgagaaaga tggttcccgt ttgctcccgg tggaggctcc gaggctgtgt   840
atatactcga cattacttta gcttgtttg ttgtttcttt ccctttccca caagactcag    900
gtctcgttcg caaacgagtc ccacaccgtc taaacttacc acaatattag cgtttataat   960
tagatgcact gcatcactta tt                                           982
```

<210> SEQ ID NO 9
<211> LENGTH: 105
<212> TYPE: DNA
<213> ORGANISM: Glycine max

<400> SEQUENCE: 9

```
gtcccttcgg ggacatccaa taaaattgga acgatacata aagattagc atggcccctg    60 tgcaaggatg acatgcacaa atcaagaaat ggtccaaatt ttttt                  105
```

<210> SEQ ID NO 10
<211> LENGTH: 949
<212> TYPE: DNA
<213> ORGANISM: Glycine max

<400> SEQUENCE: 10

```
caattggacc cctcctacct acaaatgctt taaatgcagg cttaagtgag gtcattttgt    60
atatacaaca tcctgaacaa ccaattttag agataacaaa tacacaatca actagataat   120
```

```
gaaaaaactt atcaagcaag attgcaaaaa taaccataat atatgagtac ttacccaaca      180
ctaccacaat aatggatata cgtggtgata gtgtagtaat tttaacgaat gtatatgatg      240
acgattattg aatatccatt ttcaatagtg agtttaacct ttgaacaagg agtacaacga      300
caggttgaca aaaaccgtca taattgtatt gctagtacaa agacgatttt tatataagac      360 cgtcttttgaa taatcttact tattattccc aaaatcacta attagcttcc tctcaatcgc     420
gtgtaacctt cttctttact tacgttcatc tttgtccaag ttgtggattc cctcgaaggt      480
ttgaattcaa tgactccctc aaacctcgct tagttttcta tttctgttcg actttctttg      540
accctcctag aatttctgct taaaagtgtg tttgcctttg tgtttacagt tgtgaccctc      600
gaacccactt gcactctctc actcaagctt tgactgggcc ctctctctct tgaagctttg      660
cgaagcaatg ctggagtagt tcatctgtca agtctccgtc aaaggtgtct gtgtaggtaa      720
gaacccttat ctttcaagtg ttcgttttcc ttcgatgtgg gtacaatggt tgaatccagt     780
ttgttctcag tctaaagggt gcttattttgt tctttctac aaccgagtga agagatcgag      840
ttaagcttaa tggaaatgtg aggtatcttc ctttcgttag ggcaacacct agtttgtagc     900
aagtccacat cggtgaatat aattaacccc aagcaacgat aaaaaacat                 949

<210> SEQ ID NO 11
<211> LENGTH: 89
<212> TYPE: DNA
<213> ORGANISM: Glycine max

<400> SEQUENCE: 11
gtcccttcgg ggacatccga ggaaattgaa agcatggccc ttgcgcaagg atgacacgct      60
tttatcaaga aatggtccaa tttattttt                                       89

<210> SEQ ID NO 12
<211> LENGTH: 956
<212> TYPE: DNA
<213> ORGANISM: Glycine max

<400> SEQUENCE: 12
aatacaaaga aacaaaaacct aaggaatcct aaaggaggaa tttgagagag gttaagtcct    60
gtgtcttgag agaaaaataa tataatatgg aattatctca attctaagaa tacggtcttt    120
atctttaatt actagtagta tataggatgg aattttctat atgtaaaact aaatttggat    180
tcatttgaca ataatattat gcaggcacgg aattcttcaa ttttttaacta tgtggtcaca   240 cttactacaa taatgaccat tttacgacac acaaactacg acggttaaaa aaaaaacatc    300
gttgaaagat acacggtaac agtgtagtaa ttttaaagaa tgtatacaat gatggttatt    360
gaataaccat ttttaatagc gagtttaagg agtacaacga caggttgaca agaccgtcg     420 tagttgtatt ggtagtacaa agatagtttt ttccttttga ctgtctttga ataagcttac    480
ttattattcc caaaatcact aataattaag tagcttcctc tccgttgcgc tcgcgtaacc    540
ttcttctgtt cattgttgtc caacttctgg attccctcga ctgtttgaat tcaatgactc    600
cctcaaaacc acccgcactc tctgactcaa gctttgacta ggccctttgt ctcttgaatc    660
tctgcgaagt aacgccaaag cagttcatct gtgaagtctc cgtcaaaggt gtctatgtag    720
gtaagaaccc ctgtccgtca agttttttgtt ttccttcgat gtggttgaat ctagtttgtt   780
cttagtcgaa agggtgtcta tttgttgttt tctggaaccg agtgaagaga tcgagttaag    840
cttaatggga atgtgagata tcttcgtttc gttaaggtag cacctggttt gtagcaagtc    900
cacttcggtg aatctaatta acaaaaatat ataccccaag caacgataaa aaacat        956
```

<210> SEQ ID NO 13
<211> LENGTH: 107
<212> TYPE: DNA
<213> ORGANISM: Glycine max

<400> SEQUENCE: 13

```
gtcccttcgg ggacatctga taaaattgga acgatacaga gaagattagc atggcccctg    60
cgcaaggatg acacgcacaa atcgagaaat ggtccaaatt ttttttt                 107
```

<210> SEQ ID NO 14
<211> LENGTH: 950
<212> TYPE: DNA
<213> ORGANISM: Glycine max

<400> SEQUENCE: 14

```
aaaaggagat gaaatatttt ttttaaatc tttcgttcta attatatttt tatccacatg     60
attcaaactt ataatcttat ttaagatgac taataatatt taaatcaacg atttattgta   120
aaaaaaaata tatttcttat ttgagaaaga gagaaattat acaagataa atccataaaa    180
taaataataa aaaattaatt tagttaaaga aatataatta attaatattc taatttatac   240
aatatacaat ataaatattt gtattctttg atgctgcgaa tgaattcggc tttgacgcag   300
tttgtaacaa agataaatatg tatttataca cattatagta ttttttaaaa taaaattagt  360
actaataaca ttataaaata ttattcataa attataaaaa aaattgaatt aatattctca   420
tatatttta ctaaaatgta ctagattggg gttaaaaaat tagcaaatga aaaaatataa    480
taccttaaga gaattgtaag tgtgcttta tatattaaa attaatatat tttgaaatgt     540
taaaatataa aagaaaattc aatgtaaatt aaaaatataat aaatgtttaa taagataaaa  600
ttttaaaaca taaagaaaa tgtctaacaa gaggattaag atcctgtgct cttaaatttt    660
taggtgttga aatcttagcc atacaaaata tattttatta aaaccaagca tgaaaaaagt   720
cactaaagag ctatataact catgcagcta gaaatgaagt gaagggaatc cagtttgttc   780
tcagtcgaaa gagtgtctat ctttgttctt ttctgcaacc gagttaagca aaatgggaat   840
gcgaggtatc ttcctttcgt tagggagca ccagatgcat agttagtccc acattgatga    900
atataacaag agcttcacag aatatatagc ccaggccaca gtaaaagctt              950
```

<210> SEQ ID NO 15
<211> LENGTH: 105
<212> TYPE: DNA
<213> ORGANISM: Glycine max

<400> SEQUENCE: 15

```
gtcccttggg gacatccaat aaaattagaa agatatagag aagattagta tggcccatgt    60
gcaaggatga cacgcacaaa tccagaagat ttagaatttg ttttt                   105
```

<210> SEQ ID NO 16
<211> LENGTH: 956
<212> TYPE: DNA
<213> ORGANISM: Glycine max

<400> SEQUENCE: 16

```
ttattctttc ttgtaactaa tgatttaatt tataactata accagaacat caacataaaa    60
ctataatatg ccataattaa gtagttgaac tttaggttaa ttgtaccaat aataataata   120
ataataatca ataaataaat aagaaactgt ttagaacact tgacctaaaa ttttcggtcc   180
```

```
agtttccacc agtgttaatt tcttgagtta tacatgtacc gaactcgata agcagatgta    240
gtgtggacca cttacttaca tgcattatgc atatgatcta gttgcaggaa tatagaatat    300
atgtcactca aaagtttaac atgcagggat atatacgtac ctccactcat ttacgttaga    360
ctacaaccac ttttgctaac cacctgaaca aacatctgaa ccaaataata ataataaat    420 gtttgtcaca ttgactaatc tctcttacgt acgccaattt tcgtgtattt ccacagcttt    480
atccaaaaag gtggccgaca ttcgaatga atgctcctca aaccccaccc cctccctttt    540
aatgcttttt tttcttctta ttagggtaaa acatatact tcatttagct ataggaatta    600
ggactctcgt atatgtatca aattaaaaag gaataaataa ataaataaat aaacaacgaa    660
caaaaattag tggctcaaac taaaatatta tctacacgtg ctgcggggat ttccaatcga    720
ataatatacg gaaatttcat tcaatttagg gttgttaggt gctaccttgc cgttgctacg    780
ttagtgaata aaatagctag ttgtccgggg caaaatctta caaaatcttg tgcaattatc    840
acttatatat ggttccattg acccaagaaa agacaatgtt atcaataaag atggatatac    900
ttaataagat ccaatccata tttcgcaata ttataagttt aaatcttgtt ttgatg        956
```

<210> SEQ ID NO 17  
<211> LENGTH: 107  
<212> TYPE: DNA  
<213> ORGANISM: Glycine max
<400> SEQUENCE: 17

```
gtcccttcgg ggacatccga taaaattgga acgatacaga gaagattagc atggcccctg     60
cgcaaggatg acacgcacaa atcgagaaat ggtccaaatc ttttttt                  107
```

<210> SEQ ID NO 18  
<211> LENGTH: 981  
<212> TYPE: DNA  
<213> ORGANISM: Glycine max
<400> SEQUENCE: 18

```
aaaaaagacc ttatatgcta ataaaaatat caaatatgtt aataaaaaaa gtctacacat     60
ttaaagtaaa aaaagaaag aaaagtttaa aaaaattgtt ttaaacatca cttattgttg    120
gaccgacttt tcactcaaga aagcagttga atcactattg agaggctggt ttcatttttg    180
tttggaaatt tgatgtacta agctattctc tattctcatg taagcctaac aaacatatag    240
gttaacattt gtctttattt tatttccttc aatattctga ttttcagaa acaaaaggcc    300 atgtttgatt agcagtttgt tagctcattc cctatattgc actctacttt attctttctt    360
ttatattttg gtcattttg tttccatcct ttaaacctaa aatacttatg ccacatacat    420 cagttttac ttactgagta ctgagtagta tgcagaattg cagatatgac gttgcactgg    480
gagctatact tgacacgtga tagtaaaaga gtgattgaga tttgtttttg gttgaacgtt    540
tgacatgtgt gatttagtat aaagtgaagt aatggtcaaa agaaaaagtg taaaacgaag    600
tacctagtaa taagtaatat tgaacaaaat aaatggtaaa gtgtcagata tataaaatag    660
gctttaataa aaggaagaaa aaaacaaac aaaaaatagg ttgcaatggg gcagagcaga    720
gtcatcatga agctagaaag gctaccgata gataaactat agttaattaa atacattaaa    780
aaatacttgg atctttctct taccctgttt atattgagac ctgaaacttg agagagatac    840
actaatcttg ccttgttgtt tcattcccta acttacagga ctcagcgcat gtcatgtggt    900
ctcgttcccc atttaagtcc cacaccgtct aaacttatta aattattaat gtttataact    960
agatgcacaa caacaaagct t                                              981
```

<210> SEQ ID NO 19
<211> LENGTH: 88
<212> TYPE: DNA
<213> ORGANISM: Glycine max

<400> SEQUENCE: 19 gtcccttttgg ggacatccga ggaaattgga agcatggccc ctgcgcaagg atgacacgct    60
tttatcaagc aatggtccaa tttttttt    88

<210> SEQ ID NO 20
<211> LENGTH: 956
<212> TYPE: DNA
<213> ORGANISM: Glycine max

<400> SEQUENCE: 20
ttcagacaac tagagatctg gttatcttcc ttaaaccact ttaatattca ttttctatct    60
tcttatcttt gattgtttat atctctataa ttgagtaaag caagttatta atcataagta   120
tcactactac aataatggtt atttacgaca cactaactac gacgattaag aagaaaatgt   180
cgttgaagga tacacggtgg cagtgtagta attttaatga atatatatac aatgacggtt   240
attgaataac catcttcaat agtgagttta aggagtacaa cgataggttg acaaagacta   300
tcgtagttgt attggtagta caaagatggt ttttcctttt tgactgtctt tgaataagct   360
tacttattat tcctggaatc actactaatt aagtagcttc ctctcagtcg cgcgcgcgta   420 accttttttct ctgcttcttc cattcatcgt tgtccaagtt gtcgattcct tcaaaggttt   480
gaattcaatg actccctcaa aaccccctta tgattttgtt tctcttcaac tttctctgac   540
cctcctagaa tttctactta aaagtgtgtt tgcctttgtg tttatagtga ccctcgaacc   600
catctgcact ctctcactaa agctttgact gggccctctg tctcttgaat ctctgcgaag   660
caacgctgga gcagttcatc tgtgaagtct ccgtcaaagg tgtctgtgta ggtaaaaacc   720
cctgtctgtc aagtgtttgt tttcctttga tgtgggtact atggttgaat ctagtttgtt   780
ctcaatcgaa agggtgtctg ttttttgttt tctgcaatcg agtgaagaga ccgagttaag   840
cttaatggga atgtgaggta tcttcatttc attagggcag cacctggttt gtagcaagtc   900
cacttcagtg aatataatta acaaaaatat atttcccaag caacgataaa aaactt   956

<210> SEQ ID NO 21
<211> LENGTH: 107
<212> TYPE: DNA
<213> ORGANISM: Glycine max

<400> SEQUENCE: 21
gtcccttcgg ggacatccga taaaattgga acgatacaga gaagattagc atggcccctg    60
cgcaaggatg acacgcacaa atcgagaaat ggtccaaatt tttttt   107

<210> SEQ ID NO 22
<211> LENGTH: 953
<212> TYPE: DNA
<213> ORGANISM: Glycine max

<400> SEQUENCE: 22
accagatagc atcacacact aagtttgtta gaaaaaactt aagtttaatt gtcacataat    60
tcatcattcg gtagagatga tgaactttaa atgtaaataa gattttaatc gaagattgat   120
cccataagat cataattgac tcaaaggatc aaatcttgta gaaatatctt ggaatttcat   180

| | | | | |
|---|---|---|---|---|
| tgaaaagtca | aagattttaa | ttaggatgat | taaaaaaatt | atttaatcct aaaaatcaat | 240 |
| cttacaagga | accactataa | aactagttga | acccatcgaa | aactaactac agttgacaaa | 300 |
| atctatttgg | ttggttgatt | ttttttaatt | aaaaacatcc | aatcttaatg atataattat | 360 |
| agcttaatat | tataagattt | ttataaaaat | tatatttatt | ttgtttctaa ttatgctaag | 420 |
| agatattatt | atttgttatt | taacttaaat | attatcacaa | acttgattga aacttatgtt | 480 |
| taatttaaaa | tattatatgt | catgagttat | gactccaata | atcacaatta taaagtgaag | 540 |
| tttaattttt | agtattacaa | atatttttt | gttgtttaat | tttaattact taatgtatta | 600 |
| tgttaataat | taaaaataca | aattatttat | tattaatgca | atcacagttt gtggatttga | 660 |
| caaaagaaat | agggatcta | aaattgtaga | taagccaaag | ttaaaacttg aattgactat | 720 |
| ttttgtctct | ttactctgca | ccaactttac | tattccttct | tttagtgtga gcttcatgca | 780 |
| tcttgttcac | cgcaattccg | ctcggtgaaa | gttgcacaat | tcactcacaa tctgtttctg | 840 |
| gtctgttagg | tttgttactt | ggagtgacac | gatgacgcaa | cagtacaagt cccacatcgt | 900 |
| ttgagtatac | agttttcaag | cagtttatat | tcccatagcc | ttagcaagag ctt | 953 |

<210> SEQ ID NO 23
<211> LENGTH: 108
<212> TYPE: DNA
<213> ORGANISM: Glycine max

<400> SEQUENCE: 23

| | | | | |
|---|---|---|---|---|
| gtcccttcgg | ggacatctga | taaaattgga | acgatacaga | gaagattagc atggcccctg | 60 |
| cgcaaggatg | acacgcacaa | atcgagaaat | ggtccaattt | tttttttt | 108 |

<210> SEQ ID NO 24
<211> LENGTH: 948
<212> TYPE: DNA
<213> ORGANISM: Glycine max

<400> SEQUENCE: 24

| | | | | |
|---|---|---|---|---|
| aatgcccgaa | gaatttgatt | gatcataatg | atgttttcc | tcttaattac attttctca | 60 |
| ttaaaaaact | taaattcaaa | atcttgtata | agagtataat | attatttta gattaacgat | 120 |
| ttattggtag | atagaatata | agaacttgtg | ttggaaagag | agaaattata aataaataag | 180 |
| agaaaaataa | ttttcctaaa | aaatataatt | aactagtatt | tgatttatac attatacaaa | 240 |
| ataattattt | gtgttctttg | atactgcgaa | tgaattgggc | ttaaaccgag tttgtaaaaa | 300 |
| agatactatg | tatttataca | aattatagta | ttttaaata | aaattagtac aaataacatt | 360 |
| aaaaaatatt | attaataaag | tataaaatat | tattttgac | taaaatgtag gagattaggg | 420 |
| ttaaaaata | gcaaataaaa | aaattataat | accttaagag | aattgtaagt gtgtttttat | 480 |
| atatttaaaa | ttaatatatt | ttgaaatctt | aaaaatgtaa | aaaaatcaa tggaaaataa | 540 |
| aaagaaataa | ataatattc | agtagataaa | ttttaaaata | taaagaaaa tgtccaacaa | 600 |
| gaggattaag | atcctgtgcc | cttacatttt | aggtgttgaa | atcttagcca tacaaaatat | 660 |
| attttcttta | aaacgaagca | tgaaaaagt | ctctataggc | cagcaccttt gaatctttag | 720 |
| ctataactca | tgcagctaga | aatgaggaga | agggaatcca | gtttgttctc agtcgaaagg | 780 |
| gtgtctcttt | gttctattct | gcaaccgagc | gaagagaccc | agttaagcta aatgggaatg | 840 |
| tgaggtatct | tcctttcgtt | agggcagcac | ctggtttgtt | gcaagtccac atcggtgaat | 900 |
| ataacaaaaa | cttaatagaa | tatatagccc | aagcaacgat | aaaagcat | 948 |

<210> SEQ ID NO 25
<211> LENGTH: 106
<212> TYPE: DNA
<213> ORGANISM: Glycine max

<400> SEQUENCE: 25

| | | | | | | |
|---|---|---|---|---|---|---|
| gtcccttcgg | ggacatccga | taaaattgga | acgatacaga | gaagattagc | atggcccctg | 60 |
| cgcaaggatg | acacgcacaa | atcgagaaat | ggtccaaatt | tttttt | | 106 |

<210> SEQ ID NO 26
<211> LENGTH: 982
<212> TYPE: DNA
<213> ORGANISM: Glycine max

<400> SEQUENCE: 26

| | | | | | | |
|---|---|---|---|---|---|---|
| tggagaattg | ggatcaagga | ttgaggagat | aatatccgtc | ctcgtccagc | ctcattgcca | 60 |
| tatctacact | gcctaaaaat | aaaatttta | ctattctttt | taaccaatga | tctatcataa | 120 |
| ttaaaggatg | tttcaccatt | aagtttaaat | ttgaattagt | ttttggaaag | ggattgtgta | 180 |
| gaatactgaa | tacgtagatt | acagattttt | ctaaattgat | catggtaaaa | ccattttgtg | 240 |
| aggattaagt | tgttttaga | aacaactgtt | gaacattttt | aatttctctt | gtagatggtt | 300 |
| gtatcttaat | caaaatgcta | aatgtatgca | agtatcaacc | atggctatga | aaatagactt | 360 |
| gaaacgatgt | gggagaagaa | tttgaagatt | atgaagaaat | gtagatatca | ttataaaacc | 420 |
| tattttatta | tacaaataca | cttgttttat | cttttctttt | ctacaaaaca | ttataaaaag | 480 |
| taaaatataa | ctactttgtt | ttttaataaa | aaaaattcaa | tgggagatac | tatggattca | 540 |
| attaccttac | tgattttatt | tcatatgtgc | cagaagtatt | tcagtttatt | ttgaaaaatc | 600 |
| agaaaaaaaa | tgtctggaat | aaaatataat | aagcgatact | aataaataat | tgaacaagat | 660 |
| aaatggtaaa | atgtcaaatc | aaaactaggc | tacagagtgc | agagcagagt | catgatgaat | 720 |
| gacagctagt | tctacttact | acaccgattc | ttgtgtacat | aaaaatattt | taaataatt | 780 |
| gaatctttct | ttagccagct | tgacaacaa | tgtacaccgt | tcgtacttct | tactggtagg | 840 |
| caatgcttct | tgtttgcttt | cggtggaagg | tgtatatact | caacattact | tcttttttcag | 900 |
| cgtgttttct | tacgggagtc | ccacaccgcc | caaaactaat | acagtattct | tgtttataaa | 960 |
| gaagtgcacc | acttcaattg | tt | | | | 982 |

<210> SEQ ID NO 27
<211> LENGTH: 105
<212> TYPE: DNA
<213> ORGANISM: Glycine max

<400> SEQUENCE: 27

| | | | | | | |
|---|---|---|---|---|---|---|
| gtcccttcgg | ggacatctga | taaaattgga | acgatacaga | gaagattagc | atggcccctg | 60 |
| cgcaaggatg | acacgcacaa | atcgagaaat | ggtccaaatt | ttttt | | 105 |

<210> SEQ ID NO 28
<211> LENGTH: 999
<212> TYPE: DNA
<213> ORGANISM: Glycine max

<400> SEQUENCE: 28

| | | | | | | |
|---|---|---|---|---|---|---|
| ttaaaaaaat | tatctttatc | aaaataatta | aatataagag | aaaaagtgca | ctaacaatat | 60 |
| aaaagtattt | tatgttgtct | tttacttata | aattaccatt | tatgataaat | tagttgattt | 120 |
| ttacaaaatt | gtcctaaaag | tcatacaaac | gataatttgt | gattgaatga | caatttaca | 180 |

```
ttgactggac atcactatta aactctaaat ttaaaatgtt tttaaactca aagatatata    240
taagtataca ctacataata atggaggtgt aagattaact tgtgatataa agaaaaagaa    300
agaagaaaaa aatcataaat ttaattcttt ctgccaataa aaaaattaat aattaatgtt    360
tgcccataaa agaaactata cagtactatt agagtgtttg taaataaaca tgaaatagaa    420
gtaaataaaa ataaaaatta tgaattaaaa taagatgtaa aaatatgaat tttatctcat    480
tttattgttt atttcatttc tttttaactc acctttggtg caaatacaac agtttgaaaa    540
taaactgcta agttgtgaat ctcaccacta aaatctatta aaatataatt ttaaaagata    600
aatttgttat tcaataatag cttttaaat ataggaaaat gcataattta actaattaaa    660
gaaaataaaa atgcaagtgc ggtgacaaga caagctagaa taaagttgca aagaaatgac    720
agggctacaa aaggctcacc tacttctgga tttaccaaac ttctgttttgt ccccatactc    780
caaaaacaaa accattttt tttatcttcg tttttgtttg ctttgactgt gagttgaggc    840
ccaactttct gcttctgtcc gactctattt gatgaatttt gtttgcctcc tgtgatgtga    900
aggatgtatc attgaaaggg aacgtgtctc aatgatccca catcggccaa atatgctcat    960
tacattgcgt ttatatagtc ccaggaaaac atatggatt                          999

<210> SEQ ID NO 29
<211> LENGTH: 107
<212> TYPE: DNA
<213> ORGANISM: Glycine max

<400> SEQUENCE: 29
gtccctttgg gggcatccta tacaaatgga atgatacaga gaagattagc atggccccg     60 tgcaaggatg acacgcacaa attgagaaat ggtccaaatt ttgttttt                107

<210> SEQ ID NO 30
<211> LENGTH: 995
<212> TYPE: DNA
<213> ORGANISM: Glycine max

<400> SEQUENCE: 30 gtaattttc cacagcagac agaagtagta ataaaaggca actataggaa taataggatt     60
attttctctg ccctgatacg tagtttcaag tttcgagctt tcctttgttt gatggtgagt    120
acttgtactg aacttataat tgattagcct ttgcatggta agcagaatta ttcttgctaa    180
cagaactctg atgcttggat ttgatgttgt tagtcattat acatgatgag cttatcgaga    240
aatcgttctc aaatctatag tcacaaatct acactacttt tttcttcttt tttatatcaa    300
ttgacctcat aaattataac agttaacttg tttgtggttg atttggttgc ttttttatt    360 cttcctctaa ccgcatccaa ttacaccact aattatactt tacagtgttt gaaagaaatt    420
tgaatgtaac taacaatatt gaatttaaa ttagggaaga agtattctta cgttgcaaac    480
gagtatgaca atgcaaagt atccttaatt tacactgcaa ggataacaac tttacataac    540
tcggaatttc atatctttga aatgaggaag caaggttttg tatttacaa aagtttatgc    600 aaatataatg aggtaattga actagttagt tgtgttatgt atcatacact attacatggc    660
actgtttgtc cgctcattac atgattcagc ttatagatga aagagtgaag gaacttgctc    720
ttaaattata ggacaagttg aactaatttg ttaggtgatt ggttggctgc atataaatga    780
taataataga atacattgaa atatctgtat ctttctgtgt atcattccat ctttcatctt    840
gcatgttgtt tgccaccaat gaagggctgt gcaggactca agcatttggc tccagctagt    900
gattgcaatg tgactgtgtc tgtctccaca gtcccatatc aaccaaatat gctccatgca    960
```

```
ctgtgtttat ataacaccag gggaatacat taatt                                995
```

<210> SEQ ID NO 31
<211> LENGTH: 106
<212> TYPE: DNA
<213> ORGANISM: Glycine max

<400> SEQUENCE: 31

```
gtcccttcgg ggacatccga taaaattgga acgatacaga gaagattagc atggcccctg      60
cgcaaggatg acacgcacaa atcgagaaat ggtccaaatt tttttt                    106
```

<210> SEQ ID NO 32
<211> LENGTH: 1059
<212> TYPE: DNA
<213> ORGANISM: Glycine max

<400> SEQUENCE: 32

```
atattaaaga gtatgttgct aaacactttt ttatttttaa taaaccatga tagttatctc      60
agcagaaacc atgtatccaa agcaaaaatt tcaacaagtt caatgctgat tcagaaacat     120
cttatttttc acaattttta acaaataatg aaatggcatg tttacaatat taatagtaat     180
agtattaaat taaataataa attatatcaa aagactaatt ttttaataca tatattactt     240
ataaaatatt attaataatg ttgataatta ttattgttga aaatattttt tttaagtatg     300
attacttaaa tcttattaaa aaaatgtcac aatgacacat gtccaacttc tgaacaatta     360
tatatatata tatatatata tatatatata tatatattaa aatatagtta ttatttaagt     420
tctgttaatg attattaatc tttatcaaag aaggatgatt attgataatg gaatttaatt     480
tgtttccaat tatattttt tatttgtaag acttaaatat gatacttaag aaagttgagt     540
tctatttcat ttgaccaatc acatattgat aaagttttag tgtttgaaaa aaaaagtata     600
gataaatata aaatgtttta taaaatataa acgataaaa atgttttaaa cgatatatat     660
tataaaaaaa aacgtttcaa aaataaatac aaaaatgttt ttaaatatat ataatttaac     720
tcattaaaga aaataaaaat gcaagtgcgg tgacaagaca agctaaaagt tgcaaaagaa     780
atggcagggc tataaggctc acctactcct ggatttacca aattttggtt cgtccctata     840
ctcgaaaaat aaaacaaaat aaatttcagt atcttcgttt ttgtatgctt tgactgtgag     900
gcgaggccaa ctttcttctt ctgtctgaga tgaattttgt ttgcctcctg tgaaggatgt     960
atcattcaaa gtgaatgttt tgcaactgcc agtagtccca catcgaccaa atattcttat    1020
tacagtgtgt ttatatagca cctggagaag gaatgggtt                           1059
```

<210> SEQ ID NO 33
<211> LENGTH: 117
<212> TYPE: DNA
<213> ORGANISM: Glycine max

<400> SEQUENCE: 33

```
gtcccttcga agaatgggga catatgataa aattggaacc atacagagaa gattagcgtt      60
gccctgtgca aggatgacac gcacaaatca agaaatgctc caatttttg tttttt         117
```

<210> SEQ ID NO 34
<211> LENGTH: 936
<212> TYPE: DNA
<213> ORGANISM: Glycine max

<400> SEQUENCE: 34

```
ccgatggaaa tatttagatt ttctacagaa attaatctat ggataaaatt ccatccgtaa    60
ttttaacttt ctgatggaaa aattgtccat cggtaaattc catcaataat tcaaaaattt   120
ctatacaaaa ttttcaaaat ttttgacgaa atttattctt ttgataaatt ctatcaacaa   180
tttaaatgtt tctgatgaaa tatttttcgt tggaaataat aattttttct gtagtgtttg   240
agttgttctt aggctacaac aatatgtgac gatgatgtga gacatattta ggttgcgaca   300
atgatgtgct caagctgtga tgaggtgcga caatgaaaga ttattattgt gattttgaaa   360
tcatgcagtg tgggatgagg agcggatggt tatgcctttt ccctctttat tttagttttt   420
gataaaaaga atttgttttc aattattaaa aaaaatatta ctcattaaaa tatatcacag   480
gcggatgtag tatggaggga tgttaataca gttcttattc tcaactgtga aaggggttgc   540
tgcagccaat cgaaccactt cattccatgc tggggaggtt gcaatgaaaa agatttagg    600
ccccgccaaa ccctcataac attcgtgcat ctaaagaata tattgcacct tggccatgta   660
tcatcatcag aacaccttgg ccgtataaaa ttttgaattt aactcaaaag ttacgcaaaa   720
ttaattctaa cacaaaaata attctgaatt tttctctcat gtgaaattaa acatctaaaa   780
atatattcaa aatcaatttc agacttagaa tcaatttttt aacaccaaat caaaccgaaa   840
cccaagatac tttctcaaat tgttaataaa ctgaatttga aaaatatag acaatttacg    900
tgtttatata acaaaagaca aacataggga tcgtct                             936

<210> SEQ ID NO 35
<211> LENGTH: 106
<212> TYPE: DNA
<213> ORGANISM: Glycine max

<400> SEQUENCE: 35
gtcccttcgg ggacatccga taaaattgga acgatacaga gaagattagc atggcccctg    60
cgcaaggatg acacgcacaa atcgagaaat ggtccaaatt ttttt                    106

<210> SEQ ID NO 36
<211> LENGTH: 982
<212> TYPE: DNA
<213> ORGANISM: Glycine max

<400> SEQUENCE: 36
ctagtggagc ctgcgattca actgctgctc ctgctgccac cttgctgcaa ccctgaaaaa    60
gctgagctgc aaccctgaaa tagctgagga gccctgctac ctgcaaatcg ccagtttgac   120
tggctagtcc catgccacgt gttgacgcca gcccaaaccc gccaataggg ctggcgattt   180
tcttcttcca tgcatgcact ctcgtacaaa acagcccctc attaaaaaat ctttacaaac   240
aacctcattt tagaaaatag tttgtaaaaa gatctccaat gggaaatttt gccttagttt   300
ataattaaaa cttatttata ctcaaatttt agtagcttct gacttatagt tgagtgttct   360
ttgaaatttc aacgtggcta aatggcatac gtaatcatgt caagcataaa atttaagaat   420
tattttattt atataatatt tttatatcat aatctatttt attgtacact ttttttttg    480
cttttgtttt ctacaaaaca ttataaaaag taagatataa caacttttttt tttaaaaaa    540
tcaataggaa atattatcgg ttcagttaat ttacagagag atatttattt catatgtgcc   600
agaagtattt cagttcctta tgaaaaatca gaaaaatgta tggaataaaa tataataatc   660
gatactaata atagaacaaa ataaatggta aaatgtcaaa tcaaaactag gctgcagtat   720
gcagagcaga gtcatgatga tactacttac tacaccgatt cttgtgtgca gaaaaatatg   780
ttaaaataat tgaatctttc tctagccaaa tttgacaaca atgtacaccg ttcatattga   840
```

```
gagacgatgc ttcttgtttg ctttcggtgg aagctgcata tactcaacat tactccttca    900
gcgagttttc caactgagtc ccacattgcc cagacctaac acggtattct tgtttataat    960
gaaatgtgcc accacatgga tt                                             982
```

<210> SEQ ID NO 37
<211> LENGTH: 106
<212> TYPE: DNA
<213> ORGANISM: Glycine max

<400> SEQUENCE: 37

```
gtcccttcgg ggacatccga taaaattgga acgatacaga gaagattagc atggcccctg     60
cgcaaggatg acacgcacaa atcgagaaat ggtccaaatt tttttt                   106
```

<210> SEQ ID NO 38
<211> LENGTH: 1021
<212> TYPE: DNA
<213> ORGANISM: Glycine max

<400> SEQUENCE: 38

```
tgaggaataa ataaagcaca tatttatttt ttatttattt taactaaatg acaaatttat     60
ttaattattt tttcaattac caaaatgaga aaaattaatg taaaaattta atattttta    120
attcacaaaa attccatgtc aacataacat atgtcaagtg agcataaaga ttagtgtgga    180
acatagatag gtgataattg tgtattcata tcaacatata acatagagat agacagaaag    240
aacgaaaatg tgtaacggaa taaaagatta atgatgttga tcaattaaaa atttgtttga    300
ggattaaaac tcaaaatttc aaaaaattta aatactaaaa acttagttaa cctaaaaatt    360
aaaggaaaga gaaaaaaaaa atctaacaga gagggtgaat catataaaca atgatatata    420
aaagtggttt attatagaat cacgtcatat gttttcctc ggtaaccttg tttctttat     480
tctaagttct tgttgccatg ttttttgcgct tctctatcca agtatccatt tatattcata    540
attttttttt tttgttttt tatacaagga cggctgattc aatcatcaca ccacacgtca    600
tattaaaaaa atatagtaga tttatttttaa aatagagaga atcgttaaga aaaaaataaa    660
tagtaaagta aatgaaaacc caaataatat cattattatg tcaataagtc ggagaggata    720
gtaatcaaat ggtctatgag gtggtggttc attcaacata tagcacctat tcattgttcc    780
taaaacataa tttaagaaca aaaacttaaa cttaaataat aataataaaa gagtacatcg    840
aagtatctgt gttctctatc cttctgacta acattcatgt tgtttgtatt cagcaaaggg    900
ccgtgcagga tttgtgcgtc gcgctccggt tagttattgc agtgaccgtc tctttagtcc    960
cacatcgagt aattatgctt catacagtct gtttatataa cagagatgga acaaactggt   1020
t                                                                   1021
```

<210> SEQ ID NO 39
<211> LENGTH: 110
<212> TYPE: DNA
<213> ORGANISM: Glycine max

<400> SEQUENCE: 39

```
gtccctgtgg gggtatctga caaaattgga actttcatag aatgattaac agcatgactc     60
ctctgcaagg atgatacgca cacaaatcga aaaatgattt aatttttttt                110
```

<210> SEQ ID NO 40
<211> LENGTH: 947
<212> TYPE: DNA

<213> ORGANISM: Glycine max

<400> SEQUENCE: 40

```
tatttttaa caaatattag ttatcgataa aataaatatt atggactaaa aatataatta      60
aaataataa taatgaagaa gtagaaataa ttaattaaaa ttaaactttc aaaaatttaa     120
gttaaactat ttaactaaaa tacattgatc taaataaaca atatcaaaat aaatatgcaa    180
aactttcaaa attctttatt gtttcttgt taagtaatgg agaaatttta tcattttcaa     240
aattttatt atttcaaaa tttttattat tttttattat tttcaacaat attatttaaa      300
aactatcctt atgaaaatat gtttctttta aacaaaaggt agtaattttt ttaatagaaa    360
aatatagtaa atgtttaaaa actattctca ttaaatttag ctactgattg ttttaaaaaa    420
ttatttatt tcctccacat acatattgtt tctcttcttc tttatttatt atattttct      480
actataaaac tcacagcacc aataaagccc aagacttaga attgggctat aagtccaaac    540
cataactgca cagattgatt ttggtggtaa tatcaaccta tttatgaaaa agagtaaaag    600
attaaacatt cacaatcttt caacctacaa gttcatagtc tatctataac atcagccaat    660
aatagaaaaa gagtaactgt atctaatatt ctaatttcat tgatgtttca tatgaatttc    720
ctaccgtcac ccatcatgta tttaaagcca ctatctcgtc attttcaggg aaagacaact    780
aaatgtgtaa aggcacgtgg aagaggtagg ttcattttca aggcagccaa cttaacatta    840
acaactaaat gtgtatctaa taagacttga cccttttcagc tagtaattgc attactaaat   900
ataactagtt ccctatcttt atatagcacc aggcgtaaca atgaata               947
```

<210> SEQ ID NO 41
<211> LENGTH: 20
<212> TYPE: DNA
<213> ORGANISM: Glycine max

<400> SEQUENCE: 41

```
gtcccttgta cttgtacgta                                                20
```

<210> SEQ ID NO 42
<211> LENGTH: 28
<212> TYPE: DNA
<213> ORGANISM: Artificial sequence
<220> FEATURE:
<223> OTHER INFORMATION: gRNA forward primer gRNA-F

<400> SEQUENCE: 42

```
cccttgtact tgtacgtagt tttagagc                                       28
```

<210> SEQ ID NO 43
<211> LENGTH: 23
<212> TYPE: DNA
<213> ORGANISM: Artificial sequence
<220> FEATURE:
<223> OTHER INFORMATION: AM labeled gRNA probe gRNA-T

<400> SEQUENCE: 43

```
caagttaaaa taaggctagt ccg                                            23
```

<210> SEQ ID NO 44
<211> LENGTH: 21
<212> TYPE: DNA
<213> ORGANISM: Artificial sequence
<220> FEATURE:
<223> OTHER INFORMATION: gRNA reverse primer gRNA-R

<400> SEQUENCE: 44

```
cggtgccact ttttcaagtt g                                               21

<210> SEQ ID NO 45
<211> LENGTH: 21
<212> TYPE: DNA
<213> ORGANISM: Artificial sequence
<220> FEATURE:
<223> OTHER INFORMATION: 35S promoter forward primer 35S-277F

<400> SEQUENCE: 45
gacagtggtc ccaaagatgg a                                               21

<210> SEQ ID NO 46
<211> LENGTH: 21
<212> TYPE: DNA
<213> ORGANISM: Artificial sequence
<220> FEATURE:
<223> OTHER INFORMATION: FAM labeled 35S promoter probe 35S-299T

<400> SEQUENCE: 46
ccccacccac gaggagcatc g                                               21

<210> SEQ ID NO 47
<211> LENGTH: 22
<212> TYPE: DNA
<213> ORGANISM: Artificial sequence
<220> FEATURE:
<223> OTHER INFORMATION: 35S promoter reverse primer 35S-345R

<400> SEQUENCE: 47
cgtggttgga acgtcttctt tt                                              22

<210> SEQ ID NO 48
<211> LENGTH: 24
<212> TYPE: DNA
<213> ORGANISM: Artificial sequence
<220> FEATURE:
<223> OTHER INFORMATION: HSP forward primer HSP-F1

<400> SEQUENCE: 48
caaacttgac aaagccacaa ctct                                            24

<210> SEQ ID NO 49
<211> LENGTH: 20
<212> TYPE: DNA
<213> ORGANISM: Artificial sequence
<220> FEATURE:
<223> OTHER INFORMATION: VIC labeled HSP probe HSP-T1

<400> SEQUENCE: 49
ctctcatctc atataaatac                                                 20

<210> SEQ ID NO 50
<211> LENGTH: 21
<212> TYPE: DNA
<213> ORGANISM: Artificial sequence
<220> FEATURE:
<223> OTHER INFORMATION: HSP reverse primer HSP-R1

<400> SEQUENCE: 50
ggagaaattg gtgtcgtgga a                                               21

<210> SEQ ID NO 51
<211> LENGTH: 25
<212> TYPE: DNA
```

<210> SEQ ID NO 51
<211> LENGTH: 25 (implied)
<213> ORGANISM: Artificial sequence
<220> FEATURE:
<223> OTHER INFORMATION: U6RNA forward primer U6RNA-F1

<400> SEQUENCE: 51
tggaacgata cagagaagat tagca                                  25

<210> SEQ ID NO 52
<211> LENGTH: 16
<212> TYPE: DNA
<213> ORGANISM: Artificial sequence
<220> FEATURE:
<223> OTHER INFORMATION: FAM labeled U6RNA probe U6RNA-T1

<400> SEQUENCE: 52
tcatccttgc gcaggg                                            16

<210> SEQ ID NO 53
<211> LENGTH: 22
<212> TYPE: DNA
<213> ORGANISM: Artificial sequence
<220> FEATURE:
<223> OTHER INFORMATION: U6RNA reverse primer U6RNA-R1

<400> SEQUENCE: 53
ttggaccatt tctcgatttg tg                                     22

<210> SEQ ID NO 54
<211> LENGTH: 24
<212> TYPE: DNA
<213> ORGANISM: Artificial sequence
<220> FEATURE:
<223> OTHER INFORMATION: ATPS forward primer ATPS-87F

<400> SEQUENCE: 54
catgattggg agaaaccta agct                                    24

<210> SEQ ID NO 55
<211> LENGTH: 20
<212> TYPE: DNA
<213> ORGANISM: Artificial sequence
<220> FEATURE:
<223> OTHER INFORMATION: VIC labeled ATPS probe ATPS-117T

<400> SEQUENCE: 55
ttctcctgct aagacatact                                        20

<210> SEQ ID NO 56
<211> LENGTH: 20
<212> TYPE: DNA
<213> ORGANISM: Artificial sequence
<220> FEATURE:
<223> OTHER INFORMATION: ATPS reverse primer ATPS-161R

<400> SEQUENCE: 56
agattgggcc agaggatcct                                        20

<210> SEQ ID NO 57
<211> LENGTH: 3365
<212> TYPE: DNA
<213> ORGANISM: Artificial sequence
<220> FEATURE:
<223> OTHER INFORMATION: Plasmid fragment, QC795A

<400> SEQUENCE: 57
cgcgccggta cccgggtgtg atttagtata aagtgaagta atggtcaaaa gaaaaagtgt    60

```
aaaacgaagt acctagtaat aagtaatatt gaacaaaata aatggtaaag tgtcagatat     120
ataaaatagg ctttaataaa aggaagaaaa aaaacaaaca aaaataggt tgcaatgggg      180 cagagcagag tcatcatgaa gctagaaagg ctaccgatag ataaactata gttaattaaa    240
tacattaaaa aatacttgga tctttctctt accctgttta tattgagacc tgaaacttga    300
gagagataca ctaatcttgc cttgttgttt cattccctaa cttacaggac tcagcgcatg    360
tcatgtggtc tcgttcccca tttaagtccc acaccgtcta aacttattaa attattaatg    420
tttataacta gatgcacaac aacaaagctt gtcccttgta cttgtacgta gttttagagc    480
tagaaatagc aagttaaaat aaggctagtc cgttatcaac ttgaaaaagt ggcaccgagt    540
cggtgctttt ttttgcggcc gcaattggat ccaattccaa tcccacaaaa atctgagctt    600
aacagcacag ttgctcctct cagagcagaa tcgggtattc aacaccctca tatcaactac    660
tacgttgtgt ataacggtcc acatgccggt atatacgatg actggggttg tacaaaggcg    720
gcaacaaacg gcgttcccgg agttgcacac aagaaatttg ccactattac agaggcaaga    780
gcagcagctg acgcgtacac aacaagtcag caaacagaca ggttgaactt catccccaaa    840
ggagaagctc aactcaagcc caagagcttt gctaaggccc taacaagccc accaaagcaa    900
aaagcccact ggctcacgct aggaaccaaa aggcccagca gtgatccagc cccaaaagag    960
atctcctttg ccccggagat tacaatggac gatttcctct atctttacga tctaggaagg   1020
aagttcgaag gtgaaggtga cgacactatg ttcaccactg ataatgagaa ggttagcctc   1080
ttcaatttca gaaagaatgc tgacccacag atggttagag aggcctacgc agcaggtctc   1140
atcaagacga tctacccgag taacaatctc caggagatca aataccttcc caagaaggtt   1200
aaagatgcag tcaaaagatt caggactaat tgcatcaaga acacagagaa agacatattt   1260
ctcaagatca gaagtactat tccagtatgg acgattcaag gcttgcttca taaaccaagg   1320
caagtaatag agattggagt ctctaaaaag gtagttccta ctgaatctaa ggccatgcat   1380
ggagtctaag attcaaatcg aggatctaac agaactcgcc gtgaagactg gcgaacagtt   1440
catacagagt cttttacgac tcaatgacaa gaagaaaatc ttcgtcaaca tggtggagca   1500
cgacactctg gtctactcca aaaatgtcaa agatacagtc tcagaagacc aaagggctat   1560
tgagactttt caacaaagga taatttcggg aaacctcctc ggattccatt gcccagctat   1620
ctgtcacttc atcgaaagga cagtagaaaa ggaaggtggc tcctacaaat gccatcattg   1680
cgataaagga aaggctatca ttcaagatgc ctctgccgac agtggtccca agatggacc    1740 cccacccacg aggagcatcg tggaaaaaga agacgttcca accacgtctt caaagcaagt   1800
ggattgatgt gacatctcca ctgacgtaag ggatgacgca caatcccact atccttcgca   1860
agacccttcc tctatataag gaagttcatt tcatttggag aggacacgct cgagctcatt   1920
tctctattac ttcagccata acaaaagaac tctttctct tcttattaaa ccatgaaaaa    1980
gcctgaactc accgcgacgt ctgtcgagaa gtttctgatc gaaaagttcg acagcgtctc   2040
cgacctgatg cagctctcgg agggcgaaga atctcgtgct ttcagcttcg atgtaggagg   2100
gcgtggatat gtcctgcggg taaatagctg cgccgatggt ttctacaaag atcgttatgt   2160
ttatcggcac tttgcatcgg ccgcgctccc gattccggaa gtgcttgaca ttggggaatt   2220
cagcgagagc ctgacctatt gcatctcccg ccgtgcacag ggtgtcacgt tgcaagacct   2280
gcctgaaacc gaactgcccg ctgttctgca gccggtcgcg gaggccatgg atgcgatcgc   2340
tgcggccgat cttagccaga cgagcgggtt cggcccattc ggaccgcaag gaatcggtca   2400
```

```
atacactaca tggcgtgatt tcatatgcgc gattgctgat ccccatgtgt atcactggca   2460
aactgtgatg gacgacaccg tcagtgcgtc cgtcgcgcag gctctcgatg agctgatgct   2520
ttgggccgag gactgccccg aagtccggca cctcgtgcac gcggatttcg gctccaacaa   2580
tgtcctgacg gacaatggcc gcataacagc ggtcattgac tggagcgagg cgatgttcgg   2640
ggattcccaa tacgaggtcg ccaacatctt cttctggagg ccgtggttgg cttgtatgga   2700
gcagcagacg cgctacttcg agcggaggca tccggagctt gcaggatcgc cgcggctccg   2760
ggcgtatatg ctccgcattg gtcttgacca actctatcag agcttggttg acggcaattt   2820
cgatgatgca gcttgggcgc agggtcgatg cgacgcaatc gtccgatccg gagccgggac   2880
tgtcgggcgt acacaaatcg cccgcagaag cgcggccgtc tggaccgatg gctgtgtaga   2940
agtactcgcc gatagtggaa accgacgccc cagcactcgt ccgagggcaa aggaatagtg   3000
agaacctaga cttgtccatc ttctggattg gccaacttaa ttaatgtatg aaataaaagg   3060
atgcacacat agtgacatgc taatcactat aatgtgggca tcaaagttgt gtgttatgtg   3120
taattactag ttatctgaat aaaagagaaa gagatcatcc atatttctta tcctaaatga   3180
atgtcacgtg tctttataat tctttgatga accagatgca tttcattaac caaatccata   3240
tacatataaa tattaatcat atataattaa tatcaattgg gttagcaaaa caaatctagt   3300
ctaggtgtgt tttgcgaatt cgatatcaag cttatcgata ccgtcgaggg ggggcccggt   3360
accgg                                                              3365

<210> SEQ ID NO 58
<211> LENGTH: 1131
<212> TYPE: DNA
<213> ORGANISM: Artificial sequence
<220> FEATURE:
<223> OTHER INFORMATION: Plasmid fragment, QC819A

<400> SEQUENCE: 58
cgcgccggta cccgggttaa gagaattgta agtgtgcttt tatatattta aaattaatat     60
attttgaaat gttaaaatat aaaagaaaat tcaatgtaaa ttaaaaataa ataaatgttt    120
aataaagata aattttaaaa cataaaagaa aatgtctaac aagaggatta agatcctgtg    180
ctcttaaatt tttaggtgtt gaaatcttag ccatacaaaa tatattttat taaaaccaag    240
catgaaaaaa gtcactaaag agctatataa ctcatgcagc tagaaatgaa gtgaagggaa    300
tccagtttgt tctcagtcga aagagtgtct atctttgttc ttttctgcaa ccgagttaag    360
caaaatggga atgcgaggta tcttcctttc gttaggggag caccagatgc atagttagtc    420
ccacattgat gaatataaca agagcttcac agaatatata gcccaggcca cagtaaaagc    480
ttgtcccttg tacttgtacg tagttttaga gctagaaata gcaagttaaa ataaggctag    540
tccgttatca acttgaaaaa gtggcaccga gtcggtgctt ttttttgcgg ccgctcgagt    600
gccagaagta tttcagttta ttttgaaaaa tcagaaaaaa aatgtctgga ataaaatata    660
ataagcgata ctaataaata attgaacaag ataaatggta aaatgtcaaa tcaaaactag    720
gctacagagt gcagagcaga gtcatgatga atgacagcta gttctactta ctacaccgat    780
tcttgtgtac ataaaaatat tttaaaataa ttgaatcttt cttagccag ctttgacaac    840 aatgtacacc gttcgtactt cttactggta ggcaatgctt cttgtttgct ttcggtggaa    900
ggtgtatata ctcaacatta cttcttttttc agcgtgtttt cttacgggag tcccacaccg    960
cccaaaacta atacagtatt cttgtttata aagaagtgca ccacttcaat tgttgtccct   1020
tcggggacat ccgataaaat tggaacgata cagagaagat tagcatggcc cctgcgcaag   1080
```
gatgacacgc acaaatcgag aaatggtcca aattttggg cccggtaccg g                1131

<210> SEQ ID NO 59
<211> LENGTH: 6611
<212> TYPE: DNA
<213> ORGANISM: Artificial sequence
<220> FEATURE:
<223> OTHER INFORMATION: Plasmid fragment, QC799A

<400> SEQUENCE: 59

| | | | | | |
|---|---|---|---|---|---|
| cgcgccggta | cccgggttaa | gagaattgta | agtgtgcttt | tatatattta | aaattaatat | 60 |
| attttgaaat | gttaaaatat | aaagaaaat | tcaatgtaaa | ttaaaaataa | ataaatgttt | 120 |
| aataaagata | aattttaaaa | cataaaagaa | aatgtctaac | aagaggatta | agatcctgtg | 180 |
| ctcttaaatt | tttaggtgtt | gaaatcttag | ccatacaaaa | tatattttat | aaaaccaag | 240 |
| catgaaaaaa | gtcactaaag | agctatataa | ctcatgcagc | tagaaatgaa | gtgaagggaa | 300 |
| tccagtttgt | tctcagtcga | aagagtgtct | atctttgttc | ttttctgcaa | ccgagttaag | 360 |
| caaaatggga | atgcgaggta | tcttcctttc | gttagggag | caccagatgc | atagttagtc | 420 |
| ccacattgat | gaatataaca | agagcttcac | agaatatata | gcccaggcca | cagtaaaagc | 480 |
| ttgtcccttg | tacttgtacg | tagttttaga | gctagaaata | gcaagttaaa | ataaggctag | 540 |
| tccgttatca | acttgaaaaa | gtggcaccga | gtcggtgctt | tttttgcgg | ccgcaattgg | 600 |
| atcgggttta | cttattttgt | gggtatctat | acttttatta | gattttaat | caggctcctg | 660 |
| attttctttt | atttcgattg | aattcctgaa | cttgtattat | tcagtagatc | gaataaatta | 720 |
| taaaagata | aaatcataaa | ataatattt | atcctatcaa | tcatattaaa | gcaatgaata | 780 |
| tgtaaaatta | atcttatctt | tatttaaaa | aatcatatag | gttagtatt | ttttaaaaa | 840 |
| taagatagg | attagttta | ctattcactg | cttattactt | ttaaaaaaat | cataaaggtt | 900 |
| tagtatttt | ttaaaataaa | tataggaata | gttttactat | tcactgcttt | aatagaaaaa | 960 |
| tagtttaaaa | tttaagatag | ttttaatccc | agcatttgcc | acgtttgaac | gtgagccgaa | 1020 |
| acgatgtcgt | tacattatct | taacctagct | gaaacgatgt | cgtcataata | tcgccaaatg | 1080 |
| ccaactggac | tacgtcgaac | ccacaaatcc | cacaaagcgc | gtgaaatcaa | atcgctcaaa | 1140 |
| ccacaaaaaa | gaacaacgcg | tttgttacac | gctcaatccc | acgcgagtag | agcacagtaa | 1200 |
| ccttcaaata | agcgaatggg | gcataatcag | aaatccgaaa | taaacctagg | ggcattatcg | 1260 |
| gaaatgaaaa | gtagctcact | caatataaaa | atctaggaac | cctagttttc | gttatcactc | 1320 |
| tgtgctccct | cgctctattt | tcagtctct | gtgtttgcgg | ctgaggattc | cgaacgagtg | 1380 |
| accttcttcg | tttctcgcaa | aggtaacagc | ctctgctctt | gtctcttcga | ttcgatctat | 1440 |
| gcctgtctct | tatttacgat | gatgtttctt | cggttatgtt | tttttattta | tgctttatgc | 1500 |
| tgttgatgtt | cggttgtttg | tttcgctttg | ttttttgtggt | tcagttttt | aggattcttt | 1560 |
| tggttttga | atcgattaat | cggaagagat | tttcgagtta | tttggtgtgt | tggaggtgaa | 1620 |
| tcttttttt | gaggtcatag | atctgttgta | tttgtgttat | aaacatgcga | ctttgtatga | 1680 |
| tttttttacga | ggttatgatg | ttctggttgt | tttattatga | atctgttgag | acagaaccat | 1740 |
| gattttgtt | gatgttcgtt | tacactatta | aaggtttgtt | ttaacaggat | taaaagtttt | 1800 |
| ttaagcatgt | tgaaggagtc | ttgtagatat | gtaaccgtcg | atagtttttt | tgtgggtttg | 1860 |
| ttcacatgtt | atcaagctta | atcttttact | atgtatgcga | ccatatctgg | atccagcaaa | 1920 |
| ggcgattttt | taattccttg | tgaaactttt | gtaatatgaa | gttgaaattt | tgttattggt | 1980 |

```
aaactataaa tgtgtgaagt tggagtatac ctttaccttc ttatttggct ttgtgatagt    2040
ttaatttata tgtattttga gttctgactt gtatttcttt gaattgattc tagtttaagt    2100
aatccatgga caaaaagtac tcaatagggc tcgacatagg gactaactcc gttggatggg    2160
ccgtcatcac cgacgagtac aaggtgccct ccaagaagtt caaggtgttg ggaaacaccg    2220
acaggcacag cataaagaag aatttgatcg gtgccctcct cttcgactcc ggagagaccg    2280
ctgaggctac caggctcaag aggaccgcta gaaggcgcta caccagaagg aagaacagaa    2340
tctgctacct gcaggagatc ttctccaacg agatggccaa ggtggacgac tccttcttcc    2400
accgccttga ggaatcattc ctggtggagg aggataaaaa gcacgagaga cacccaatct    2460
tcgggaacat cgtcgacgag gtggcctacc atgaaaagta ccctaccatc taccacctga    2520
ggaagaagct ggtcgactct accgacaagg ctgacttgcg cttgatttac ctggctctcg    2580
ctcacatgat aaagttccgc ggacacttcc tcattgaggg agacctgaac ccagacaact    2640
ccgacgtgga caagctcttc atccagctcg ttcagaccta caaccagctt ttcgaggaga    2700
acccaatcaa cgccagtgga gttgacgcca aggctatcct ctctgctcgt ctgtcaaagt    2760
ccaggaggct tgagaacttg attgcccagc tgcctggcga aaagaagaac ggactgttcg    2820
gaaacttgat cgctctctcc ctgggattga ctcccaactt caagtccaac ttcgacctcg    2880
ccgaggacgc taagttgcag ttgtctaaag acacctacga cgatgacctc gacaacttgc    2940
tggcccagat aggcgaccaa tacgccgatc tcttcctcgc cgctaagaac ttgtccgacg    3000
caatcctgct gtccgacatc ctgagagtca acactgagat taccaaagct cctctgtctg    3060
cttccatgat taagcgctac gacgagcacc accaagatct gaccctgctc aaggccctgg    3120
tgagacagca gctgcccgag aagtacaagg agatcttttt cgaccagtcc aagaacggct    3180
acgccggata cattgacgga ggcgcctccc aggaagagtc ctacaagttc atcaagccca    3240
tccttgagaa gatggacggt accgaggagc tgttggtgaa gttgaacaga gaggacctgt    3300
tgaggaagca gagaaccttc gacaacggaa gcatccctca ccaaatccac ctgggagagc    3360
tccacgccat cttgaggagg caggaggatt tctatccctt cctgaaggac aaccgcgaga    3420
agattgagaa gatcttgacc ttcagaattc cttactacgt cgggccactc gccagggaa    3480 actctaggtt cgcctggatg acccgcaaat ctgaagagac cattactccc tggaacttcg    3540
aggaagtcgt ggacaagggc gcttccgctc agtctttcat cgagaggatg accaacttcg    3600
ataaaaatct gcccaacgag aaggtgctgc ccaagcactc cctgttgtac gagtatttca    3660
cagtgtacaa cgagctcacc aaggtgaagt acgtcacaga gggaatgagg aagcctgcct    3720
tcttgtccgg agagcagaag aaggccatcg tcgacctgct cttcaagacc aacaggaagg    3780
tgactgtcaa gcagctgaag gaggactact tcaagaagat cgagtgcttc gactccgtcg    3840
agatctctgg tgtcgaggac aggttcaacg cctcccttgg gcttaccac gatctgctca    3900 agattattaa agacaaggac ttcctggaca cgaggagaa cgaggacatc cttgaggaca    3960
tcgtgctcac cctgaccttg ttcgaagaca gggaaatgat cgaagagagg ctcaagacct    4020
acgcccacct cttcgacgac aaggtgatga acagctgaa gagacgcaga tataccggct    4080
ggggaaggct ctcccgcaaa ttgatcaacg ggatcaggga caagcagtca gggaagacta    4140
tactcgactt cctgaagtcc gacggattcg ccaacaggaa cttcatgcag ctcattcacg    4200
acgactcctt gaccttcaag gaggacatcc agaaggctca ggtgtctgga cagggtgact    4260
ccttgcatga gcacattgct aacttggccg gctctcccgc tattaagaag gcatttttgc    4320
agaccgtgaa ggtcgttgac gagctcgtga aggtgatggg acgccacaag ccagagaaca    4380
```

```
tcgttattga gatggctcgc gagaaccaaa ctacccagaa agggcagaag aattcccgcg    4440
agaggatgaa gcgcattgag gagggcataa aagagcttgg ctctcagatc ctcaaggagc    4500
accccgtcga gaacactcag ctgcagaacg agaagctgta cctgtactac ctccaaaacg    4560
gaagggacat gtacgtggac caggagctgg acatcaacag gttgtccgac tacgacgtcg    4620
accacatcgt gcctcagtcc ttcctgaagg atgactccat cgacaataaa gtgctgacac    4680
gctccgataa aaatagaggc aagtccgaca acgtcccctc cgaggaggtc gtgaagaaga    4740
tgaaaaacta ctggagacag ctcttgaacg ccaagctcat cacccagcgt aagttcgaca    4800
acctgactaa ggctgagaga ggaggattgt ccgagctcga taaggccgga ttcatcaaga    4860
gacagctcgt cgaaacccgc caaattacca agcacgtggc ccaaattctg gattcccgca    4920
tgaacaccaa gtacgatgaa aatgacaagc tgatccgcga ggtcaaggtg atcaccttga    4980
agtccaagct ggtctccgac ttccgcaagg acttccagtt ctacaaggtg agggagatca    5040
acaactacca ccacgcacac gacgcctacc tcaacgctgt cgttggaacc gccctcatca    5100
aaaaatatcc taagctggag tctgagttcg tctacggcga ctacaaggtg tacgacgtga    5160
ggaagatgat cgctaagtct gagcaggaga tcggcaaggc caccgccaag tacttcttct    5220
actccaacat catgaacttc ttcaagaccg agatcactct cgccaacggt gagatcagga    5280
agcgcccact gatcgagacc aacggtgaga ctggagagat cgtgtgggac aaagggaggg    5340
atttcgctac tgtgaggaag gtgctctcca tgcctcaggt gaacatcgtc aagaagaccg    5400
aagttcagac cggaggattc tccaaggagt ccatcctccc caagagaaac tccgacaagc    5460
tgatcgctag aaagaaagac tgggacccta agaagtacgg aggcttcgat tctcctaccg    5520
tggcctactc tgtgctggtc gtggccaagg tggagaaggg caagtccaag aagctgaaat    5580
ccgtcaagga gctcctcggg attaccatca tggagaggag ttccttcgag aagaacccta    5640
tcgacttcct ggaggccaag ggatataaag aggtgaagaa ggacctcatc atcaagctgc    5700
ccaagtactc cctcttcgag ttggagaacg gaaggaagag gatgctggct tctgccggag    5760
agttgcagaa gggaaatgag ctcgcccttc cctccaagta cgtgaacttc ctgtacctcg    5820
cctctcacta tgaaaagttg aagggctctc ctgaggacaa cgagcagaag cagctcttcg    5880
tggagcagca caagcactac ctggacgaaa ttatcgagca gatctctgag ttctccaagc    5940
gcgtgatatt ggccgacgcc aacctcgaca aggtgctgtc cgcctacaac aagcacaggg    6000
ataagcccat tcgcgagcag gctgaaaaca ttatccacct gtttaccctc acaaacttgg    6060
gagcccctgc tgccttcaag tacttcgaca ccaccattga caggaagaga tacacctcca    6120
ccaaggaggt gctcgacgca acactcatcc accaatccat caccggcctc tatgaaacaa    6180
ggattgactt gtcccagctg ggaggcgact ctagagccga tcccaagaag aagagaaagg    6240
tgtaggttaa cctagacttg tccatcttct ggattggcca acttaattaa tgtatgaaat    6300
aaaaggatgc acacatagtg acatgctaat cactataatg tgggcatcaa agttgtgtgt    6360
tatgtgtaat tactagttat ctgaataaaa gagaaagaga tcatccatat ttcttatcct    6420 aaaatgaatgt cacgtgtctt tataattctt tgatgaacca gatgcatttc attaaccaaa    6480
tccatataca tataaatatt aatcatatat aattaatatc aattgggtta gcaaaacaaa    6540
tctagtctag gtgtgttttg cgaattcgat atcaagctta tcgataccgt cgaggggggg    6600
cccggtaccg g                                                        6611
```

<210> SEQ ID NO 60

<211> LENGTH: 5719
<212> TYPE: DNA
<213> ORGANISM: Artificial sequence
<220> FEATURE:
<223> OTHER INFORMATION: Plasmid fragment, RTW831A

<400> SEQUENCE: 60

| | |
|---|---|
| cgcgcctcta gttgaagaca cgttcatgtc ttcatcgtaa aagacactc agtagtcttc | 60 |
| ggccagaatg gccatctgga ttcagcaggc ctagaaggcc atttaaatcc tgaggatctg | 120 |
| gtcttcctaa ggacccggga tatcgctatc aactttgtat agaaaagttg ggccgaattc | 180 |
| gagctcggta cggccagaat ccggtaagtg actagggtca cgtgaccca gtcacttaaa | 240 |
| ttcggccaga atggccatct ggattcagca ggcctagaag gcccggaccg attaaacttt | 300 |
| aattcggtcc gggttacctc gagatcttgt tcccctcctt ggtttggcat aaattgattt | 360 |
| tcatggctct tctcggtcga aactggagct aattcaccct tagtctctct taaaattctg | 420 |
| gctgtaagaa acaccacaga acacataaat tataaactaa ttataatttg aagagtaaaa | 480 |
| tatgttttta ctcttatgat ttaattagtg tagttttaat tttctccttt ttttaaaaaa | 540 |
| ttttggtatt cataaatttc aattttttaa aaataattgt tgttacccgt taatgataac | 600 |
| gggatatgtt atgttaccac taaatcggac aaaaaaaatt caaaacttt ataaggatta | 660 |
| aaattaacaa aaatatttta aaaaaatcta acctcaataa agttaaattt ataagcacaa | 720 |
| aataatactt ttaagcctaa tttggcaaga cacaagcaag ctcacctgta gcattaatag | 780 |
| aaaggaagca aagcaagaga aaagcaacca gaaggaagcg tttgcttggt gacacagcca | 840 |
| tcttacttga atttatggta ttactgagaa accttgatct tgcttcaaaa tcttctagtt | 900 |
| accctctttt tataggcaga aagagaacta gctagttgcc aataggatat gaggacatgt | 960 |
| ggtgcaatgc actcactctt caaggacaag aaaacaatg gctacaattg tggttcaaat | 1020 |
| caatgtctcc tgctctgtcc tgcctgaaaa tgacacccctt ttgcttggaa agaggatca | 1080 |
| aagctaagaa caggagtggc ttcattccct tcatgtaacc aaaacactttc gcattctgtc | 1140 |
| attcgtgaat cagcaaaatc tgcaaccaaa atatatggt gcctaaataa aagaaataaa | 1200 |
| ataatttaga gttgcggact aaaataataa acaaaagaaa tatattataa tctagaatta | 1260 |
| atttaggact aaaagaagag gcagactcca attcctcttt tctagaatac cctccgtacg | 1320 |
| tacactagtg gtcacctaag tgactagggt cacgtgaccc tagtcactta ttcccaaaca | 1380 |
| ctagtaacgg ccgccagtgt gctggaattc gcccttccca agctttgctc tagatcaaac | 1440 |
| tcacatccaa acataacatg gatatcttcc ttaccaatca tactaattat tttgggttaa | 1500 |
| atattaatca ttatttttaa gatattaatt aagaaattaa aagattttt aaaaaaatgt | 1560 |
| ataaaattat attattcatg atttttcata catttgattt tgataataaa tatattttt | 1620 |
| ttaatttctt aaaaaatgtt gcaagacact tattagacat agtcttgttc tgtttacaaa | 1680 |
| agcattcatc atttaataca ttaaaaaata tttaatacta acagtagaat cttcttgtga | 1740 |
| gtggtgtggg agtaggcaac ctggcattga acgagagaa agagagtcag aaccagaaga | 1800 |
| caaataaaaa gtatgcaaca aacaaatcaa atcaaaggg caaggctgg ggttggctca | 1860 |
| attggttgct acattcaatt ttcaactcag tcaacggttg agattcactc tgacttcccc | 1920 |
| aatctaagcc gcggatgcaa acggttgaat ctaacccaca atccaatctc gttacttagg | 1980 |
| ggcttttccg tcattaactc acccctgcca cccggtttcc ctataaattg gaactcaatg | 2040 |
| ctcccctcta aactcgtatc gcttcagagt tgagaccaag acacactcgt tcatatatct | 2100 |
| ctctgctctt ctcttctctt ctacctctca aggtactttt cttctcccct taccaaatcc | 2160 |

```
tagattccgt ggttcaattt cggatcttgc acttctggtt tgctttgcct tgcttttcc    2220
tcaactgggt ccatctagga tccatgtgaa actctactct ttctttaata tctgcggaat    2280
acgcgtttga ctttcagatc tagtcgaaat catttcataa ttgcctttct ttcttttagc    2340
ttatgagaaa taaaatcact ttttttttat ttcaaaataa accttgggcc ttgtgctgac    2400
tgagatgggg tttggtgatt acagaatttt agcgaatttt gtaattgtac ttgtttgtct    2460
gtagttttgt tttgttttct tgtttctcat acattcctta ggcttcaatt ttattcgagt    2520
ataggtcaca ataggaattc aaactttgag caggggaatt aatcccttcc ttcaaatcca    2580
gtttgtttgt atatatgttt aaaaaatgaa acttttgctt taaattctat tataactttt    2640
tttatggctg aaattttgc atgtgtcttt gctctctgtt gtaaatttac tgtttaggta    2700
ctaactctag gcttgttgtg cagttttga agtataacaa cagaagttcc tattccgaag    2760
ttcctattct ctagaaagta taggaacttc cactagtcca tgaaaaagcc tgaactcacc    2820
gcgacgtctg tcgagaagtt tctgatcgaa aagttcgaca cgtctccga cctgatgcag    2880
ctctcggagg gcgaagaatc tcgtgctttc agcttcgatg taggagggcg tggatatgtc    2940
ctgcgggtaa atagctgcgc cgatggttc tacaaagatc gttatgttta tcggcactt    3000
gcatcggccg cgctcccgat tccggaagtg cttgacattg gggaattcag cgagagcctg    3060
acctattgca tctcccgccg tgcacagggt gtcacgttgc aagacctgcc tgaaaccgaa    3120
ctgcccgctg ttctgcagcc ggtcgcgag gccatggatg cgatcgctgc ggccgatctt    3180
agccagacga gcgggttcgg cccattcgga ccgcaaggaa tcggtcaata cactacatgg    3240
cgtgatttca tatgcgcgat tgctgatccc catgtgtatc actggcaaac tgtgatggac    3300
gacaccgtca gtgcgtccgt cgcgcaggct ctcgatgagc tgatgctttg gccgaggac    3360
tgccccgaag tccggcacct cgtgcacgcg gatttcggct ccaacaatgt cctgacggac    3420
aatggccgca taacagcggt cattgactgg agcgaggcga tgttcgggga ttcccaatac    3480
gaggtcgcca acatcttctt ctggaggccg tggttggctt gtatggagca gcagacgcgc    3540
tacttcgagc ggaggcatcc ggagcttgca ggatcgccgc ggctccgggc gtatatgctc    3600
cgcattggtc ttgaccaact ctatcagagc ttggttgacg gcaatttcga tgatgcagct    3660
tgggcgcagg tcgatgcga cgcaatcgtc cgatccggag ccgggactgt cgggcgtaca    3720
caaatcgccc gcagaagcgc ggccgtctgg accgatggct gtgtagaagt actcgccgat    3780
agtggaaacc gacgccccag cactcgtccg agggcaaagg aatagtgagg tacctaaaga    3840
aggagtgcgt cgaagcagat cgttcaaaca tttggcaata aagtttctta agattgaatc    3900
ctgttgccgg tcttgcgatg attatcatat aatttctgtt gaattacgtt aagcatgtaa    3960
taattaacat gtaatgcatg acgttattta tgagatgggg ttttatgatt agagtcccgc    4020
aattatacat ttaatacgcg atagaaaaca aaatatagcg cgcaaactag gataaattat    4080
cgcgcgcggt gtcatctatg ttactagatc gatgtcgacc cgggccctag gaggccggcc    4140
cagctgatga tcccggtgaa gttcctattc cgaagttcct attctccaga agtataggaa    4200
acttcactag agcttgcggc cgcgcatgct gacttaatca gctaacgcca ctcgacctgc    4260
aggcatgccc gcggatatcg atgggccccg gccgaagctt caagttttgta caaaaaagca    4320
ggctggcgcc ggaaccaatt cagtcgactg gatccggtac cgaattcgcg gccgcactcg    4380
agatatctag acccagcttt cttgtacaaa gtggccgtta acggatcggc cagaatccgg    4440
taagtgacta gggtcacgtg accctagtca cttaaattcg gccagaatgg ccatctggat    4500
```

```
tcagcaggcc tagaaggccc ggaccgatta aactttaatt cggtccgggt tacctctaga    4560
aagcttgtcg acctgcaggt acaagtacaa gggacttgtg agttgtaagg ctgtatttac    4620
aatagtgaaa agagaatcat ctgggtgatt gggttttag tccccagtga cgaattaaag     4680
gtttgaattc ttagtatgtt tgggaatcaa ttaggaattt cgttttggac tttccaaagc    4740
aattattcac ttttttcattc attaaatgtg actaaaaaat tgttatttct ccattggcca   4800
ggatgcatcg tttatataaa cataaccta gtgaaagcag tgttttcatg tgacagcggc     4860
agactatatc ttaaacaaaa ttacttgtaa agaaagatac cgttaggaaa aaaatgaaaa    4920
gaaaattgaa gctatcactt gtttactttc ctaatatctt tcaagaatac aatgtggtga    4980
atttcaattt tccctacata tgtataccgt cagcctgacg caacttatga aacttctctt    5040
tctttcattt gatgtatata taagacaca ttatatataa agaaactta tatatatctc      5100 catcatattt tagtacttgc tactatgtaa aattagctgt tggaagtatc tcaagaaaca    5160
tttaatttat tgaaccaagc attaaccatt catctacatt tgagttctaa aataaatctt    5220
aaatgatgtg gaggaaggga aattgttaat tatttccctc ttctcctaca tggatatacc    5280
tgaaacatgc aatggatgga ttagatttta acatttgcag cctgagaagt tcactgactt    5340
tcctccagct attttatgtg tgcccgccac catttatagc tcatgattgt agctgaactg    5400
caaaaactgc atcgattgca aactgaaatt gagaatctct tttcaacttt atatgctgat    5460
tgatgcatgc tgagcatgct atactagtac tcgaagttcc tatatgtaga ctttgttact    5520
gcctaatata ctttgtgttt gttctcaagt tcttatttta tttcatattt tttcctataa    5580
aaggttaatg gctctataaa ggttgagtga cggatccggt cacctaagtg actagggtca    5640 cgtgaccta gtcacttatt cccgggcaac tttattatac aaagttgata gatctcgaat     5700
tcattccgat taatcgtgg                                                  5719
```

<210> SEQ ID NO 61
<211> LENGTH: 22
<212> TYPE: DNA
<213> ORGANISM: Artificial sequence
<220> FEATURE:
<223> OTHER INFORMATION: SAMS:HPT forward primer Sams-76F

<400> SEQUENCE: 61
aggcttgttg tgcagttttt ga                                              22

<210> SEQ ID NO 62
<211> LENGTH: 22
<212> TYPE: DNA
<213> ORGANISM: Artificial sequence
<220> FEATURE:
<223> OTHER INFORMATION: FAM labeled SAMS:HPT probe FRT1I-63T

<400> SEQUENCE: 62
tggactagtg gaagttccta ta                                              22

<210> SEQ ID NO 63
<211> LENGTH: 21
<212> TYPE: DNA
<213> ORGANISM: Artificial sequence
<220> FEATURE:
<223> OTHER INFORMATION: SAMS:HPT reverse primer FRT1I-41F

<400> SEQUENCE: 63
gcggtgagtt caggcttttt c                                               21

```
<210> SEQ ID NO 64
<211> LENGTH: 19
<212> TYPE: DNA
<213> ORGANISM: Artificial sequence
<220> FEATURE:
<223> OTHER INFORMATION: Cas9 forward primer Cas9-F

<400> SEQUENCE: 64
ccttcttcca ccgccttga                                                 19

<210> SEQ ID NO 65
<211> LENGTH: 19
<212> TYPE: DNA
<213> ORGANISM: Artificial sequence
<220> FEATURE:
<223> OTHER INFORMATION: FAM labeled Cas9 probe Cas9-T

<400> SEQUENCE: 65
aatcattcct ggtggagga                                                 19

<210> SEQ ID NO 66
<211> LENGTH: 21
<212> TYPE: DNA
<213> ORGANISM: Artificial sequence
<220> FEATURE:
<223> OTHER INFORMATION: Cas9 reverse primer Cas9-R

<400> SEQUENCE: 66
tgggtgtctc tcgtgctttt t                                              21

<210> SEQ ID NO 67
<211> LENGTH: 26
<212> TYPE: DNA
<213> ORGANISM: Artificial sequence
<220> FEATURE:
<223> OTHER INFORMATION: DD43 forward primer DD43-F

<400> SEQUENCE: 67
ttctagaata ccctccgtac gtacaa                                         26

<210> SEQ ID NO 68
<211> LENGTH: 19
<212> TYPE: DNA
<213> ORGANISM: Artificial sequence
<220> FEATURE:
<223> OTHER INFORMATION: FAM labeled DD43 probe DD43-T

<400> SEQUENCE: 68
caagggactt gtgagttgt                                                 19

<210> SEQ ID NO 69
<211> LENGTH: 26
<212> TYPE: DNA
<213> ORGANISM: Artificial sequence
<220> FEATURE:
<223> OTHER INFORMATION: reverse primer DD43-R;

<400> SEQUENCE: 69
cccagatgat tctcttttca ctattg                                         26

<210> SEQ ID NO 70
<211> LENGTH: 26
<212> TYPE: DNA
<213> ORGANISM: Artificial sequence
<220> FEATURE:
<223> OTHER INFORMATION: forward primer DD43-LB
```

<400> SEQUENCE: 70
gtgtagtcca ttgtagccaa gtcacc    26

<210> SEQ ID NO 71
<211> LENGTH: 24
<212> TYPE: DNA
<213> ORGANISM: Artificial sequence
<220> FEATURE:
<223> OTHER INFORMATION: reverse primer DD43-RB

<400> SEQUENCE: 71
caaaccggag agagaggaag aacc    24

<210> SEQ ID NO 72
<211> LENGTH: 23
<212> TYPE: DNA
<213> ORGANISM: Artificial sequence
<220> FEATURE:
<223> OTHER INFORMATION: forward primer DD43LB-1

<400> SEQUENCE: 72
caatgtctcc tgctctgtcc tgc    23

<210> SEQ ID NO 73
<211> LENGTH: 24
<212> TYPE: DNA
<213> ORGANISM: Artificial sequence
<220> FEATURE:
<223> OTHER INFORMATION: reverse primer DD43RB-1

<400> SEQUENCE: 73
agtttcataa gttgcgtcag gctg    24

<210> SEQ ID NO 74
<211> LENGTH: 2098
<212> TYPE: DNA
<213> ORGANISM: Glycine max

<400> SEQUENCE: 74
gtgtagtcca ttgtagccaa gtcaccaata tcttgttccc ctccttggtt tggcataaat    60
tgattttcat ggctcttctc ggtcgaaact ggagctaatt cacccttagt ctctcttaaa    120
attctggctg taagaaacac cacagaacac ataaattata aactaattat aatttgaaga    180
gtaaaatatg ttttactct tatgatttaa ttagtgtagt tttaattttc tcctttttt    240
aaaaaatttt ggtattcata aatttcaatt ttttaaaaat aattgttgtt acccgttaat    300
gataacggga tatgttatgt taccactaaa tcggacaaaa aaaattcaaa actttttataa    360
ggattaaaat taacaaaaat attttaaaaa aatctaaccct caataaagtt aaatttataa    420
gcacaaaata atacttttaa gcctaatttg gcaagacaca agcaagctca cctgtagcat    480
taatagaaag gaagcaaagc aagagaaaag caaccagaag gaagcgtttg cttggtgaca    540
cagccatctt acttgaattt atggtattac tgagaaacct tgatcttgct tcaaaatctt    600
ctagttaccc tcttttttata ggcagaaaga gaactagcta gttgccaata ggatatgagg    660
acatgtggtg caatgcactc actcttcaag gacaagaaaa acaatggcta caattgtggt    720
tcaaatcaat gtctcctgct ctgtcctgcc tgaaaatgac acccttttgc ttggaaaaga    780
ggatcaaagc taagaacagg agtggcttca ttcccttcat gtaaccaaac actttcgcat    840
tctgtcattc gtgaatcagc aaaatctgca accaaaaata tatggtgcct aaataaaaga    900
aataaaataa tttagagttg cggactaaaa taataaacaa aagaaatata ttataatcta    960

-continued

```
gaattaattt aggactaaaa gaagaggcag actccaattc ctctttttcta gaatacccctc    1020 cgtacgtaca agtacaaggg acttgtgagt tgtaaggctg tatttacaat agtgaaaaga    1080
gaatcatctg ggtgattggg tttttagtcc ccagtgacga attaaaggtt tgaattctta    1140
gtatgtttgg gaatcaatta ggaatttcgt tttggacttt ccaaagcaat tattcacttt    1200
ttcattcatt aaatgtgact aaaaaattgt tatttctcca ttggccagga tgcatcgttt    1260
atataaacat aaccttagtg aaagcagtgt tttcatgtga cagcggcaga ctatatctta    1320
aacaaaatta cttgtaaaga aagataccgt taggaaaaaa atgaaaagaa aattgaagct    1380
atcacttgtt tactttccta atatctttca agaatacaat gtggtgaatt tcaattttcc    1440
ctacatatgt ataccgtcag cctgacgcaa cttatgaaac ttctctttct ttcatttgat    1500
gtatatataa agacacatta tatataaaga aactttatat atatctccat catatttttag   1560 tacttgctac tatgtaaaat tagctgttgg aagtatctca agaaacatttt aatttattga    1620 accaagcatt aaccattcat ctacatttga gttctaaaat aaatcttaaa tgatgtggag    1680
gaagggaaat tgttaattat ttccctcttc tcctacatgg atatacctga aacatgcaat    1740
ggatggatta gatttttaaca tttgcagcct gagaagttca ctgactttcc tccagctatt    1800
ttatgtgtgc ccgccaccat ttatagctca tgattgtagc tgaactgcaa aaactgcatc    1860
gattgcaaac tgaaattgag aatctctttt caactttata tgctgattga tgcatgctga    1920
gcatgctata ctagtactcg aagttcctat atgtagactt tgttactgcc taatatactt    1980 tgtgttttgtt ctcaagttct tatttttattt catattttttt cctataaaag gttaatggct   2040
ctataaaggt tgagtgacat atatatacta taaaggttct tcctctctct ccggtttg      2098
```

<210> SEQ ID NO 75
<211> LENGTH: 60
<212> TYPE: DNA
<213> ORGANISM: Glycine max

<400> SEQUENCE: 75

```
agccttacaa ctcacaagtc ccttgtactt gtacgtacgg agggtattct agaaaagagg     60
```

<210> SEQ ID NO 76
<211> LENGTH: 59
<212> TYPE: DNA
<213> ORGANISM: Artificial sequence
<220> FEATURE:
<223> OTHER INFORMATION: PCR fragment, 3475_12_1c

<400> SEQUENCE: 76

```
agccttacaa ctcacaagtc ccttgtactt gtactacgga gggtattcta gaaagagg      59
```

<210> SEQ ID NO 77
<211> LENGTH: 59
<212> TYPE: DNA
<213> ORGANISM: Artificial sequence
<220> FEATURE:
<223> OTHER INFORMATION: PCR fragment, 3475_5_6c

<400> SEQUENCE: 77

```
agccttacaa ctcacaagtc ccttgtactt gtagtacgga gggtattcta gaaagagg      59
```

<210> SEQ ID NO 78
<211> LENGTH: 58
<212> TYPE: DNA
<213> ORGANISM: Artificial sequence
<220> FEATURE:

<223> OTHER INFORMATION: PCR fragment, 3475_5_3a

<400> SEQUENCE: 78
agccttacaa ctcacaagtc ccttgtactt gtgtacggag ggtattctag aaaagagg      58

<210> SEQ ID NO 79
<211> LENGTH: 58
<212> TYPE: DNA
<213> ORGANISM: Artificial sequence
<220> FEATURE:
<223> OTHER INFORMATION: PCR fragment, 3475_12_4c

<400> SEQUENCE: 79
agccttacaa ctcacaagtc ccttgtactt gcgtacggag ggtattctag aaaagagg      58

<210> SEQ ID NO 80
<211> LENGTH: 57
<212> TYPE: DNA
<213> ORGANISM: Artificial sequence
<220> FEATURE:
<223> OTHER INFORMATION: PCR fragment, 3475_1_20b

<400> SEQUENCE: 80
agccttacaa ctcacaagtc ccttgtactt ggtacggagg gtattctaga aaagagg       57

<210> SEQ ID NO 81
<211> LENGTH: 57
<212> TYPE: DNA
<213> ORGANISM: Artificial sequence
<220> FEATURE:
<223> OTHER INFORMATION: PCR fragment, 3478_5_1a

<400> SEQUENCE: 81
agccttacaa ctcacaagtc ccttgtactt gttacggagg gtattctaga aaagagg       57

<210> SEQ ID NO 82
<211> LENGTH: 56
<212> TYPE: DNA
<213> ORGANISM: Artificial sequence
<220> FEATURE:
<223> OTHER INFORMATION: PCR fragment, 3475_5_1a

<400> SEQUENCE: 82
agccttacaa ctcacaagtc ccttgtactt gtacggaggg tattctagaa aagagg        56

<210> SEQ ID NO 83
<211> LENGTH: 55
<212> TYPE: DNA
<213> ORGANISM: Artificial sequence
<220> FEATURE:
<223> OTHER INFORMATION: PCR fragment, 3478_12_4b

<400> SEQUENCE: 83
agccttacaa ctcacaagtc ccttgtactt tacggagggt attctagaaa agagg         55

<210> SEQ ID NO 84
<211> LENGTH: 55
<212> TYPE: DNA
<213> ORGANISM: Artificial sequence
<220> FEATURE:
<223> OTHER INFORMATION: PCR fragment, 3475_5_11b

<400> SEQUENCE: 84
agccttacaa ctcacaagtc ccttgtactg tacggagggt attctagaaa agagg         55

```
<210> SEQ ID NO 85
<211> LENGTH: 54
<212> TYPE: DNA
<213> ORGANISM: Artificial sequence
<220> FEATURE:
<223> OTHER INFORMATION: PCR fragment, 3475_5_4a

<400> SEQUENCE: 85
agccttacaa ctcacaagcc ccttgtactt acggagggta ttctagaaaa gagg            54

<210> SEQ ID NO 86
<211> LENGTH: 52
<212> TYPE: DNA
<213> ORGANISM: Artificial sequence
<220> FEATURE:
<223> OTHER INFORMATION: PCR fragment, 33475_12_2a

<400> SEQUENCE: 86
agccttacaa ctcacaagtc ccttgtatac ggagggtatt ctagaaaaga gg              52

<210> SEQ ID NO 87
<211> LENGTH: 52
<212> TYPE: DNA
<213> ORGANISM: Artificial sequence
<220> FEATURE:
<223> OTHER INFORMATION: PCR fragment, 3475_5_14a

<400> SEQUENCE: 87
agccttacaa ctcacaagtc ccttgtgtac ggagggtatt ctagaaaaga gg              52

<210> SEQ ID NO 88
<211> LENGTH: 50
<212> TYPE: DNA
<213> ORGANISM: Artificial sequence
<220> FEATURE:
<223> OTHER INFORMATION: PCR fragment, 3475_1_17a

<400> SEQUENCE: 88
agccttacaa ctcacaagtc ccttgtacgg agggtattct agaaaagagg                 50

<210> SEQ ID NO 89
<211> LENGTH: 49
<212> TYPE: DNA
<213> ORGANISM: Artificial sequence
<220> FEATURE:
<223> OTHER INFORMATION: PCR fragment, 3475_5_16c

<400> SEQUENCE: 89
agccttacaa ctcacaagtc cctttacgga gggtattcta gaaaagagg                  49

<210> SEQ ID NO 90
<211> LENGTH: 48
<212> TYPE: DNA
<213> ORGANISM: Artificial sequence
<220> FEATURE:
<223> OTHER INFORMATION: PCR fragment, 3478_8_1a

<400> SEQUENCE: 90
agccttacaa ctcacaagtc ccttacggag ggtattctag aaaagagg                   48

<210> SEQ ID NO 91
<211> LENGTH: 47
<212> TYPE: DNA
<213> ORGANISM: Artificial sequence
<220> FEATURE:
<223> OTHER INFORMATION: PCR fragment, 3475_5_5c
```

```
<400> SEQUENCE: 91
agccttacaa ctcacaagtc cctacggagg gtattctaga aaagagg          47

<210> SEQ ID NO 92
<211> LENGTH: 43
<212> TYPE: DNA
<213> ORGANISM: Artificial sequence
<220> FEATURE:
<223> OTHER INFORMATION: PCR fragment, 3478_5_1b

<400> SEQUENCE: 92
agccttacaa ctcacaagtc ccttgtactt gtaagaaaag agg              43

<210> SEQ ID NO 93
<211> LENGTH: 49
<212> TYPE: DNA
<213> ORGANISM: Artificial sequence
<220> FEATURE:
<223> OTHER INFORMATION: PCR fragment, 3478_6_7c

<400> SEQUENCE: 93
agccttacaa ctcacaagtc ctaaattaaa ggttattcta gaaaagagg        49

<210> SEQ ID NO 94
<211> LENGTH: 227
<212> TYPE: DNA
<213> ORGANISM: Artificial sequence
<220> FEATURE:
<223> OTHER INFORMATION: PCR fragment, 3475_1_10a

<400> SEQUENCE: 94
agccttacaa ctcacaagtc ccttgtactt gtagaatcca gttcataaaa caagtgacac    60
acaacagata tgaactggac tacgtcgaac ccacaaatcc cacaaagcgc gtgaaatcaa   120
atcgctcaaa ccacaaaaaa gaacaacgcg tttgttacac gctaatacca aaattatacc   180
caaatcttaa gctatttatg cgtacggagg gtattctaga aaagagg                 227

<210> SEQ ID NO 95
<211> LENGTH: 97
<212> TYPE: DNA
<213> ORGANISM: Artificial sequence
<220> FEATURE:
<223> OTHER INFORMATION: PCR fragment, 3475_1_10c

<400> SEQUENCE: 95
agccttacaa ctcacaagtc ccttgtactt gtaatgctcc cctctaaact cgtatcgctt    60
cagagttgag agtacggagg gtattctaga aaagagg                            97

<210> SEQ ID NO 96
<211> LENGTH: 183
<212> TYPE: DNA
<213> ORGANISM: Artificial sequence
<220> FEATURE:
<223> OTHER INFORMATION: PCR fragment, 3475_5_16a

<400> SEQUENCE: 96
agccttacaa ctcacaagtc ccttgtatat agatacccac aaaataagta aacccgatcc    60
aaaatcttaa atgatgtgga ggaagggaaa ttgttaatta ttccctctct tcctacatg   120 gatatacctg aaacatgcaa tggatggatt agattttgta cggagggtat tctagaaaag   180
agg                                                                183
```

<210> SEQ ID NO 97
<211> LENGTH: 234
<212> TYPE: DNA
<213> ORGANISM: Artificial sequence
<220> FEATURE:
<223> OTHER INFORMATION: PCR fragment, 3475_5_3b

<400> SEQUENCE: 97

```
agccttacaa ctcacaagtc ccttgtactt gtaccagggg atgttttta tttacattca      60
cgtcttttgg aaagagccgc taaattaagt tctcagttag gcgaaggaag tatgactgct     120
ttaccaatag ttgaaactca atcgggagat gtttcagctt atattcctac taatgtaatt     180
tccattacag atggccaaat attcttacgt acggagggta ttctagaaaa gagg           234
```

<210> SEQ ID NO 98
<211> LENGTH: 280
<212> TYPE: DNA
<213> ORGANISM: Artificial sequence
<220> FEATURE:
<223> OTHER INFORMATION: PCR fragment, 3475_1_11a

<400> SEQUENCE: 98

```
agccttacaa ctcacaagtc ccttgtactt gtaccgaaaa tttcagccat aaaaaaagtt      60
ataatagaat ttaaagcaaa agtttcattt tttaaacata tatactgaca cgctccgata     120
aaaatagagg caagtccgac aacgtcccct ccgaggaggt cgtgaagaag atgaaaaact     180
actggagaca gctcttgaac gccaagctca tcacccagcg taagctcgac aacctgacta     240
aggctgagag aggtgtacgg agggtattct agaaaagagg                           280
```

<210> SEQ ID NO 99
<211> LENGTH: 250
<212> TYPE: DNA
<213> ORGANISM: Artificial sequence
<220> FEATURE:
<223> OTHER INFORMATION: PCR fragment, 3478_1_9b

<400> SEQUENCE: 99

```
agccttacaa ctcacaagtc ccttgtactt gtactggatt tggtgaggga tgcttccgtt      60
gtcgaaggtt ctctgcttcc tcaacaggtc ctctctgttc aacttcacca acagctcctc     120
ggtaccgtcc atcttctcaa ggatgaagat cgagtgcttc gactccgtcg agatctctgg     180
tgtcgaggac aggttcaacg cctcccttgg gacttgccac gatcgtacgg agggtattct     240
agaaaagagg                                                            250
```

<210> SEQ ID NO 100
<211> LENGTH: 161
<212> TYPE: DNA
<213> ORGANISM: Artificial sequence
<220> FEATURE:
<223> OTHER INFORMATION: PCR fragment, 3478_1_9a

<400> SEQUENCE: 100

```
agccttacaa ctcacaagtc ccttatgacc tcaaaaaaaa gattcacctc caacacacca      60
aataactcga aaatctcttt cctattctct agaaagtata ggaacttcca ctagtccatg     120
aaaaagcctg aactcgtacg gagggtattc tagaaaagag g                         161
```

<210> SEQ ID NO 101
<211> LENGTH: 185
<212> TYPE: DNA
<213> ORGANISM: Artificial sequence
<220> FEATURE:

```
<223> OTHER INFORMATION: PCR fragment, 3478_5_4b

<400> SEQUENCE: 101
agccttacaa ctcacaagtc ccttgtactt gtacacctgg ggcatggaga gcaccttcct    60
cacagtagcg aaatccctcc ctttgtccca cacgatctct ccagtctcac cgttggtctc   120
gatcagtggg cgcttcctga tctcaccgtt ggcgagagtg tacggagggt attctagaaa   180
agagg                                                               185

<210> SEQ ID NO 102
<211> LENGTH: 212
<212> TYPE: DNA
<213> ORGANISM: Artificial sequence
<220> FEATURE:
<223> OTHER INFORMATION: PCR fragment, 3478_9_1c

<400> SEQUENCE: 102
agccttacaa ctcacaagtc ccttgtactt gtgctaggtt agccgaaaga tggttatcgg    60
ttcaaggacg caaggtgccc ctgcttttc agggtaataa ggggtagaga aaatgcctcg    120
agccaaagtt cgagtaccag gcgctacagc gctgaagtaa tccatgccat actcccagga   180
aaagccgtac ggagggtatt ctagaaaaga gg                                 212

<210> SEQ ID NO 103
<211> LENGTH: 231
<212> TYPE: DNA
<213> ORGANISM: Artificial sequence
<220> FEATURE:
<223> OTHER INFORMATION: PCR fragment, 3478_9_1a

<400> SEQUENCE: 103
agccttacaa ctcacaagtc ccttgtactt gtactcaagt tcttatttta tttcatattt    60
tttcctataa aaggttaatg gctctataaa ggttgagtga cggatccggt cacctaagtg   120
actagggtca cgtgacccta gtcacttatt cccgggcaac tttattatac aaagttgata   180
gatctcgaat tcattccgat taatcgtggc gagggtattc tagaaaagag g            231
```